US009683047B2

(12) United States Patent
Smith et al.

(10) Patent No.: US 9,683,047 B2
(45) Date of Patent: Jun. 20, 2017

(54) METHODS FOR TREATING PROGRESSIVE MULTIPLE SCLEROSIS

(71) Applicant: Genentech, Inc., South San Francisco, CA (US)

(72) Inventors: Craig Smith, Seattle, WA (US); Peter S. Chin, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/201,300

(22) Filed: Jul. 1, 2016

(65) Prior Publication Data

US 2017/0029522 A1   Feb. 2, 2017

Related U.S. Application Data

(60) Continuation of application No. 14/702,583, filed on May 1, 2015, now abandoned, which is a continuation of application No. 14/049,130, filed on Oct. 8, 2013, now abandoned, which is a continuation of application No. 13/414,698, filed on Mar. 7, 2012, now abandoned, which is a division of application No. 12/561,131, filed on Sep. 16, 2009, now abandoned.

(60) Provisional application No. 61/097,464, filed on Sep. 16, 2008.

(51) Int. Cl.
| | |
|---|---|
| *C07K 16/28* | (2006.01) |
| *G01N 33/68* | (2006.01) |
| *A61K 39/00* | (2006.01) |
| *G06Q 99/00* | (2006.01) |
| *A61B 5/055* | (2006.01) |
| *A61K 39/395* | (2006.01) |
| *A61K 9/00* | (2006.01) |
| *A61K 45/06* | (2006.01) |

(52) U.S. Cl.
CPC .......... *C07K 16/2887* (2013.01); *A61B 5/055* (2013.01); *A61K 9/0019* (2013.01); *A61K 39/00* (2013.01); *A61K 39/3955* (2013.01); *A61K 45/06* (2013.01); *G01N 33/686* (2013.01); *G06Q 99/00* (2013.01); *A61K 2039/505* (2013.01); *A61K 2039/507* (2013.01); *A61K 2039/545* (2013.01); *A61K 2039/55* (2013.01); *C07K 2317/24* (2013.01); *C07K 2317/565* (2013.01); *C07K 2317/76* (2013.01); *G01N 2800/52* (2013.01); *G01N 2800/7095* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,120,649 A | 10/1978 | Schechter |
| 4,485,045 A | 11/1984 | Regen |
| 4,544,545 A | 10/1985 | Ryan et al. |
| 4,665,077 A | 5/1987 | Stringfellow et al. |
| 4,676,980 A | 6/1987 | Segal et al. |
| 4,816,567 A | 3/1989 | Cabilly et al. |
| 4,861,579 A | 8/1989 | Meyer, Jr. et al. |
| 4,892,538 A | 1/1990 | Aebischer et al. |
| 4,975,278 A | 12/1990 | Senter et al. |
| 5,013,556 A | 5/1991 | Woodle et al. |
| 5,114,721 A | 5/1992 | Cohen et al. |
| 5,208,020 A | 5/1993 | Chari et al. |
| 2,229,275 A | 7/1993 | Goroff |
| 5,283,187 A | 2/1994 | Aebischer et al. |
| 5,500,362 A | 3/1996 | Robinson et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,595,721 A | 1/1997 | Kaminski |
| 5,641,870 A | 6/1997 | Rinderknecht et al. |
| 5,648,267 A | 7/1997 | Reff |
| 5,677,180 A | 10/1997 | Robinson et al. |
| 5,693,780 A | 12/1997 | Newman et al. |
| 5,721,108 A | 2/1998 | Robinson et al. |
| 5,731,168 A | 3/1998 | Carter et al. |
| 5,733,779 A | 3/1998 | Reff |
| 5,736,137 A | 4/1998 | Anderson et al. |
| 5,739,277 A | 4/1998 | Presta |
| 5,776,456 A | 7/1998 | Anderson et al. |
| 5,821,337 A | 10/1998 | Carter et al. |

(Continued)

FOREIGN PATENT DOCUMENTS

| | | |
|---|---|---|
| CA | 2019559 C | 12/1990 |
| CN | 1420129 A | 5/2003 |

(Continued)

OTHER PUBLICATIONS

Montalban et al., Ocrelizumab versus Placebo in Primary Progressive Multiple Sclerosis,Jan. 19, 2017, The New England Journal of Medicine 376(3):209-220.*

Albert, D.A. et al. (Dec. 2003). "A Phase I Trial of Rituximab (Anti-CD20) for Treatment of Systemic Lupus Erythematosus," Abstract LB9, *Arthritis and Rheumatism* 48(12): 3659.

Anderson, D.W. et al. (Mar. 1992). "Revised Estimate of the Prevalence of Multiple Sclerosis in the United States," *Ann Neurology* 31(3):333-336.

Anderson, K.C. et al.(1984). "Expression of Human B Cell-Associated Antigens on Leukemias and Lymphomas: A Model of Human B Cell Differentiation," *Blood* 63(6):1424-1433.

(Continued)

*Primary Examiner* — John Ulm

(74) *Attorney, Agent, or Firm* — Morrison & Foerster LLP

(57) ABSTRACT

The present invention concerns methods for treating progressive multiple sclerosis (MS) in a patient, and an article of manufacture with instructions for such use.

29 Claims, 18 Drawing Sheets

(56) References Cited

U.S. PATENT DOCUMENTS

| | | |
|---|---|---|
| 5,843,398 A | 12/1998 | Kaminski et al. |
| 5,843,439 A | 12/1998 | Anderson et al. |
| 5,849,898 A | 12/1998 | Seed et al. |
| 6,015,542 A | 1/2000 | Kaminski et al. |
| 6,017,733 A | 1/2000 | Reff |
| 6,090,365 A | 7/2000 | Kaminski et al. |
| 6,120,767 A | 9/2000 | Robinson et al. |
| 6,159,730 A | 12/2000 | Reff |
| 6,171,586 B1 | 1/2001 | Lam et al. |
| 6,183,744 B1 | 2/2001 | Goldenberg |
| 6,194,551 B1 | 2/2001 | Idusogie et al. |
| 6,224,866 B1 | 5/2001 | Barbera-Guillem |
| 6,242,195 B1 | 6/2001 | Idusogie et al. |
| 6,267,958 B1 | 7/2001 | Andya et al. |
| 6,287,537 B1 | 9/2001 | Kaminski et al. |
| 6,306,393 B1 | 10/2001 | Goldenberg |
| 6,348,463 B1 | 2/2002 | Head et al. |
| 6,368,596 B1 | 4/2002 | Ghetie et al. |
| 6,369,229 B1 | 4/2002 | Head et al. |
| 6,399,061 B1 | 6/2002 | Anderson et al. |
| 6,410,391 B1 | 6/2002 | Zelsacher |
| 6,455,043 B1 | 9/2002 | Grillo-Lopez |
| 6,528,624 B1 | 3/2003 | Idusogie et al. |
| 6,538,124 B1 | 3/2003 | Idusogie et al. |
| 6,565,827 B1 | 5/2003 | Kaminski et al. |
| 6,602,684 B1 | 8/2003 | Umana et al. |
| 6,652,852 B1 | 11/2003 | Robinson et al. |
| 6,677,339 B2 | 1/2004 | Head et al. |
| 6,682,734 B1 | 1/2004 | Anderson et al. |
| 6,737,056 B1 | 5/2004 | Presta |
| 6,846,476 B2 | 1/2005 | White |
| 6,893,625 B1 | 5/2005 | Robinson et al. |
| 6,896,885 B2 | 5/2005 | Hanna |
| 6,897,044 B1 | 5/2005 | Braslawsky et al. |
| 6,991,790 B1 | 1/2006 | Lam et al. |
| 7,074,403 B1 | 7/2006 | Goldenberg et al. |
| 7,122,637 B2 | 10/2006 | Presta |
| 7,151,164 B2 | 12/2006 | Hansen et al. |
| 7,799,900 B2 | 9/2010 | Adams et al. |
| 2001/0018041 A1 | 8/2001 | Hanna et al. |
| 2001/0056066 A1 | 12/2001 | Bugelski et al. |
| 2002/0004587 A1 | 1/2002 | Miller et al. |
| 2002/0006404 A1 | 1/2002 | Hanna et al. |
| 2002/0009427 A1 | 1/2002 | Wolin et al. |
| 2002/0009444 A1 | 1/2002 | Grillo-Lopez |
| 2002/0012665 A1 | 1/2002 | Hanna |
| 2002/0028178 A1 | 3/2002 | Hanna et al. |
| 2002/0039557 A1 | 4/2002 | White |
| 2002/0041847 A1 | 4/2002 | Goldberg |
| 2002/0042368 A1 | 4/2002 | Fanslow, III et al. |
| 2002/0058029 A1 | 5/2002 | Hanna |
| 2002/0128448 A1 | 9/2002 | Reff |
| 2002/0128488 A1 | 9/2002 | Yamakawa et al. |
| 2002/0136719 A1 | 9/2002 | Shenoy et al. |
| 2002/0164328 A1 | 11/2002 | Shinkawa et al. |
| 2002/0197255 A1 | 12/2002 | Anderson et al. |
| 2002/0197256 A1 | 12/2002 | Grewal |
| 2003/0021781 A1 | 1/2003 | Anderson et al. |
| 2003/0026801 A1 | 2/2003 | Weiner et al. |
| 2003/0026804 A1 | 2/2003 | Grillo-Lopez |
| 2003/0068664 A1 | 4/2003 | Albitar et al. |
| 2003/0082172 A1 | 5/2003 | Anderson et al. |
| 2003/0095963 A1 | 5/2003 | Anderson et al. |
| 2003/0103971 A1 | 6/2003 | Hariharan et al. |
| 2003/0115614 A1 | 6/2003 | Kanda et al. |
| 2003/0118592 A1 | 6/2003 | Ledbetter et al. |
| 2003/0133930 A1 | 7/2003 | Goldenberg et al. |
| 2003/0133939 A1 | 7/2003 | Ledbetter et al. |
| 2003/0147885 A1 | 8/2003 | Anderson et al. |
| 2003/0157108 A1 | 8/2003 | Presta |
| 2003/0175844 A1 | 9/2003 | Nadler et al. |
| 2003/0175884 A1 | 9/2003 | Umana et al. |
| 2003/0180292 A1 | 9/2003 | Hanna et al. |
| 2003/0185796 A1 | 10/2003 | Wolin et al. |
| 2003/0206903 A1 | 11/2003 | Grillo-Lopez |
| 2003/0219433 A1 | 11/2003 | Hansen et al. |
| 2003/0219818 A1 | 11/2003 | Bohen et al. |
| 2003/0220268 A1 | 11/2003 | Makino et al. |
| 2004/0072290 A1 | 4/2004 | Umana et al. |
| 2004/0072749 A1 | 4/2004 | Zochoer et al. |
| 2004/0093621 A1 | 5/2004 | Shitara et al. |
| 2004/0109865 A1 | 6/2004 | Niwa et al. |
| 2004/0110282 A1 | 6/2004 | Kanada et al. |
| 2004/0110704 A1 | 6/2004 | Yamane et al. |
| 2004/0132140 A1 | 7/2004 | Satoh et al. |
| 2004/0167319 A1 | 8/2004 | Teeling et al. |
| 2004/0191256 A1 | 9/2004 | Raju |
| 2004/0202658 A1 | 10/2004 | Benyunes |
| 2004/0213784 A1 | 10/2004 | Grillo-Lopez et al. |
| 2004/0228856 A1 | 11/2004 | Presta |
| 2004/0235848 A1 | 11/2004 | Okuzumi et al. |
| 2004/0259150 A1 | 12/2004 | Nakamura et al. |
| 2005/0018206 A1 | 1/2005 | Hill |
| 2005/0025764 A1 | 2/2005 | Watkins et al. |
| 2005/0031613 A1 | 2/2005 | Nakamura et al. |
| 2005/0032130 A1 | 2/2005 | Beresini et al. |
| 2005/0053602 A1 | 3/2005 | Brunetta |
| 2005/0069545 A1 | 3/2005 | Carr et al. |
| 2005/0079174 A1 | 4/2005 | Barbera-Guillem et al. |
| 2005/0095243 A1 | 5/2005 | Chan et al. |
| 2005/0106108 A1 | 5/2005 | Leung et al. |
| 2005/0112060 A1 | 5/2005 | White |
| 2005/0118174 A1 | 6/2005 | Presta |
| 2005/0123540 A1 | 6/2005 | Hanna et al. |
| 2005/0123546 A1 | 6/2005 | Umana et al. |
| 2005/0136049 A1 | 6/2005 | Ledbetter et al. |
| 2005/0160108 A1 | 7/2005 | Charlet et al. |
| 2005/0163775 A1 | 7/2005 | Chan et al. |
| 2005/0175614 A1 | 8/2005 | Ledbetter et al. |
| 2005/0180970 A1 | 8/2005 | Ledbetter et al. |
| 2005/0180972 A1 | 8/2005 | Wahl et al. |
| 2005/0180975 A1 | 8/2005 | Hanna |
| 2005/0186205 A1 | 8/2005 | Anderson et al. |
| 2005/0186216 A1 | 8/2005 | Ledbetter et al. |
| 2005/0191297 A1 | 9/2005 | Brunetta |
| 2005/0191300 A1 | 9/2005 | Goldenberg et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0233382 A1 | 10/2005 | Presta |
| 2005/0255527 A1 | 11/2005 | Yang et al. |
| 2005/0271658 A1 | 12/2005 | Brunetta et al. |
| 2005/0272916 A1 | 12/2005 | Hanai et al. |
| 2005/0276803 A1 | 12/2005 | Chan et al. |
| 2005/0276805 A1 | 12/2005 | Hanai et al. |
| 2006/0002930 A1 | 1/2006 | Brunetta et al. |
| 2006/0008523 A1 | 1/2006 | Chen et al. |
| 2006/0018900 A1 | 1/2006 | McCormick et al. |
| 2006/0024295 A1 | 2/2006 | Brunetta |
| 2006/0024300 A1 | 2/2006 | Adams et al. |
| 2006/0024800 A1 | 2/2006 | Hanai et al. |
| 2006/0025576 A1 | 2/2006 | Miller et al. |
| 2006/0029543 A1 | 2/2006 | Krause et al. |
| 2006/0034835 A1 | 2/2006 | Adams et al. |
| 2006/0034855 A1 | 2/2006 | Solomon |
| 2006/0051345 A1 | 3/2006 | Frohna |
| 2006/0051349 A1 | 3/2006 | Goldenberg et al. |
| 2006/0062787 A1 | 3/2006 | Hitraya |
| 2006/0067930 A1 | 3/2006 | Adams et al. |
| 2006/0099662 A1 | 5/2006 | Chuntharapai et al. |
| 2006/0110387 A1 | 5/2006 | Brunetta |
| 2006/0121032 A1 | 6/2006 | Dahiyat et al. |
| 2006/0134111 A1 | 6/2006 | Agarwal |
| 2006/0135430 A1 | 6/2006 | Chan et al. |
| 2006/0153838 A1 | 7/2006 | Watkins et al. |
| 2006/0179501 A1 | 8/2006 | Chan et al. |
| 2006/0188495 A1 | 8/2006 | Barron et al. |
| 2006/0194290 A1 | 8/2006 | Presta |
| 2006/0194291 A1 | 8/2006 | Presta |
| 2006/0194957 A1 | 8/2006 | Presta |
| 2006/0251652 A1 | 11/2006 | Watkins et al. |
| 2006/0275284 A1 | 12/2006 | Hanna |
| 2007/0014720 A1 | 1/2007 | Gazit-Bornstein et al. |

(56) References Cited

U.S. PATENT DOCUMENTS

| | | |
|---|---|---|
| 2007/0014785 A1 | 1/2007 | Golay et al. |
| 2007/0014797 A1 | 1/2007 | Hitraya |
| 2007/0020259 A1 | 1/2007 | Hansen et al. |
| 2007/0020265 A1 | 1/2007 | Goldenberg et al. |
| 2007/0134759 A1 | 6/2007 | Nishiya et al. |
| 2007/0224189 A1 | 9/2007 | Lazar et al. |
| 2008/0241884 A1 | 10/2008 | Shitara et al. |
| 2009/0053233 A1 | 2/2009 | De Romeui et al. |
| 2009/0155257 A1 | 6/2009 | Adams et al. |
| 2009/0197330 A1 | 8/2009 | Numazaki et al. |
| 2009/0203078 A1 | 8/2009 | Ogawa et al. |
| 2009/0311255 A1 | 12/2009 | Brunetta et al. |
| 2010/0092997 A1 | 4/2010 | Nakamura et al. |
| 2010/0158903 A1 | 6/2010 | Smith et al. |
| 2010/0233121 A1 | 9/2010 | Frohna |
| 2011/0008250 A1 | 1/2011 | Curd et al. |
| 2011/0008336 A1 | 1/2011 | Curd et al. |
| 2011/0008337 A1 | 1/2011 | Curd et al. |
| 2011/0008338 A1 | 1/2011 | Curd et al. |
| 2011/0052488 A1 | 3/2011 | Dennis, Jr. et al. |
| 2012/0199516 A1 | 8/2012 | Frohna |
| 2012/0225070 A1 | 9/2012 | Smith et al. |

FOREIGN PATENT DOCUMENTS

| | | |
|---|---|---|
| CN | 1718587 A | 1/2006 |
| EP | 0 930 894 B1 | 7/1989 |
| EP | 0 330 191 A2 | 8/1989 |
| EP | 0 330 191 A3 | 8/1989 |
| EP | 0 332 865 A2 | 9/1989 |
| EP | 0 332 865 A3 | 9/1989 |
| EP | 0 340 109 A2 | 11/1989 |
| EP | 0 340 109 B1 | 11/1989 |
| EP | 0 404 097 A2 | 12/1990 |
| EP | 0 633 945 B1 | 1/1995 |
| EP | 1 288 205 B1 | 3/2003 |
| EP | 1 477 482 B1 | 11/2004 |
| JP | 2008-501712 A | 1/2008 |
| WO | WO-81/01145 A1 | 4/1981 |
| WO | WO-88/04936 A1 | 7/1988 |
| WO | WO-88/07378 A1 | 10/1988 |
| WO | WO-90/08187 A1 | 7/1990 |
| WO | WO-90/11294 A1 | 10/1990 |
| WO | WO-91/00360 A1 | 1/1991 |
| WO | WO-91/01133 A1 | 2/1991 |
| WO | WO-92/20373 A1 | 11/1992 |
| WO | WO-93/11161 A1 | 6/1993 |
| WO | WO-93/16185 A2 | 8/1993 |
| WO | WO-93/16185 A3 | 8/1993 |
| WO | WO-93/21232 A1 | 10/1993 |
| WO | WO-93/25673 A1 | 12/1993 |
| WO | WO-94/04690 A1 | 3/1994 |
| WO | WO-94/11026 A2 | 5/1994 |
| WO | WO-94/11026 A3 | 5/1994 |
| WO | WO-94/11026 C1 | 5/1994 |
| WO | WO-94/11523 A2 | 5/1994 |
| WO | WO-94/11523 A3 | 5/1994 |
| WO | WO-95/03770 A1 | 2/1995 |
| WO | WO-96/07321 A1 | 3/1996 |
| WO | WO-97/04801 A1 | 2/1997 |
| WO | WO-97/30087 A1 | 8/1997 |
| WO | WO-97/38731 A1 | 10/1997 |
| WO | WO-98/23645 A1 | 6/1998 |
| WO | WO-98/56418 A1 | 12/1998 |
| WO | WO-98/58964 A1 | 12/1998 |
| WO | WO-99/22764 A1 | 5/1999 |
| WO | WO-99/51642 A1 | 10/1999 |
| WO | WO-99/57134 A1 | 11/1999 |
| WO | WO-00/09160 A1 | 2/2000 |
| WO | WO-00/20864 A1 | 4/2000 |
| WO | WO-00/27428 A1 | 5/2000 |
| WO | WO-00/27433 A1 | 5/2000 |
| WO | WO-00/32575 A1 | 6/2000 |
| WO | WO-00/37444 A1 | 6/2000 |
| WO | WO-00/42072 A2 | 7/2000 |
| WO | WO-00/42072 A3 | 7/2000 |
| WO | WO-00/44788 A1 | 8/2000 |
| WO | WO-00/61739 A1 | 10/2000 |
| WO | WO-00/67795 A1 | 11/2000 |
| WO | WO-00/67796 A1 | 11/2000 |
| WO | WO-00/74718 A1 | 12/2000 |
| WO | WO-00/76542 A1 | 12/2000 |
| WO | WO-01/03734 A1 | 1/2001 |
| WO | WO-01/10460 A1 | 2/2001 |
| WO | WO-01/10461 A1 | 2/2001 |
| WO | WO-01/10462 A1 | 2/2001 |
| WO | WO-01/13945 A1 | 3/2001 |
| WO | WO-01/29246 A1 | 4/2001 |
| WO | WO-01/34194 A1 | 5/2001 |
| WO | WO-01/72333 A1 | 10/2001 |
| WO | WO-01/74388 A1 | 10/2001 |
| WO | WO-01/77342 A1 | 10/2001 |
| WO | WO-01/79173 A1 | 10/2001 |
| WO | WO-01/80884 A1 | 11/2001 |
| WO | WO-01/97858 A2 | 12/2001 |
| WO | WO-01/97858 A3 | 12/2001 |
| WO | WO-02/02556 A2 | 1/2002 |
| WO | WO-02/02556 A3 | 1/2002 |
| WO | WO-02/04021 A1 | 1/2002 |
| WO | WO-02/16329 A1 | 2/2002 |
| WO | WO-02/22212 A2 | 3/2002 |
| WO | WO-02/22212 A3 | 3/2002 |
| WO | WO-02/22212 C1 | 3/2002 |
| WO | WO-02/28830 A1 | 4/2002 |
| WO | WO-02/34790 A1 | 5/2002 |
| WO | WO-02/056910 A1 | 7/2002 |
| WO | WO-02/060955 A2 | 8/2002 |
| WO | WO-02/060955 A3 | 8/2002 |
| WO | WO-02/078766 A2 | 10/2002 |
| WO | WO-02/078766 A3 | 10/2002 |
| WO | WO-02/079255 A1 | 10/2002 |
| WO | WO-02/096948 A2 | 12/2002 |
| WO | WO-02/096948 A3 | 12/2002 |
| WO | WO-02/096948 C1 | 12/2002 |
| WO | WO-02/102312 A2 | 12/2002 |
| WO | WO-02/102312 A3 | 12/2002 |
| WO | WO-03/002607 A1 | 1/2003 |
| WO | WO-03/011878 A2 | 2/2003 |
| WO | WO-03/011878 A3 | 2/2003 |
| WO | WO-03/035835 A2 | 5/2003 |
| WO | WO-03/035835 A3 | 5/2003 |
| WO | WO-03/049694 A2 | 6/2003 |
| WO | WO-03/049694 A3 | 6/2003 |
| WO | WO-03/053926 A1 | 7/2003 |
| WO | WO-03/061694 A1 | 7/2003 |
| WO | WO-03/068821 A2 | 8/2003 |
| WO | WO-03/068821 A3 | 8/2003 |
| WO | WO-03/070709 A1 | 8/2003 |
| WO | WO-03/084570 A1 | 10/2003 |
| WO | WO-03/085119 A1 | 10/2003 |
| WO | WO-03/089410 A1 | 10/2003 |
| WO | WO-2004/103404 A1 | 2/2004 |
| WO | WO-2004/032828 A2 | 4/2004 |
| WO | WO-2004/032828 A3 | 4/2004 |
| WO | WO-2004/035607 A2 | 4/2004 |
| WO | WO-2004/035607 A3 | 4/2004 |
| WO | WO-2004/035607 C1 | 4/2004 |
| WO | WO-2004/056312 A2 | 7/2004 |
| WO | WO-2004/056312 A3 | 7/2004 |
| WO | WO-2004/058298 A1 | 7/2004 |
| WO | WO-2004/060052 A2 | 7/2004 |
| WO | WO-2004/060052 A3 | 7/2004 |
| WO | WO-2004/060053 A2 | 7/2004 |
| WO | WO-2004/060053 A3 | 7/2004 |
| WO | WO-2004/091557 A2 | 10/2004 |
| WO | WO-2004/091557 A3 | 10/2004 |
| WO | WO-2004/091657 A2 | 10/2004 |
| WO | WO-2004/091657 A3 | 10/2004 |
| WO | WO-2005/000351 A2 | 1/2005 |
| WO | WO-2005/000351 A3 | 1/2005 |
| WO | WO-2005/000901 A2 | 1/2005 |
| WO | WO-2005/000901 A3 | 1/2005 |
| WO | WO-2005/005462 A2 | 1/2005 |
| WO | WO-2005/005462 A3 | 1/2005 |

(56) References Cited

FOREIGN PATENT DOCUMENTS

| | | |
|---|---|---|
| WO | WO-2005/014618 A2 | 2/2005 |
| WO | WO-2005/014618 A3 | 2/2005 |
| WO | WO-2005/016969 A2 | 2/2005 |
| WO | WO-2005/016969 A3 | 2/2005 |
| WO | WO-2005/017148 A1 | 2/2005 |
| WO | WO-2005/017529 A1 | 2/2005 |
| WO | WO-2005/023302 A2 | 3/2005 |
| WO | WO-2005/023302 A3 | 3/2005 |
| WO | WO-2005/035586 A1 | 4/2005 |
| WO | WO-2005/035778 A1 | 4/2005 |
| WO | WO-2005/037989 A2 | 4/2005 |
| WO | WO-2005/037989 A3 | 4/2005 |
| WO | WO-2005/044859 A2 | 5/2005 |
| WO | WO-2005/044859 A3 | 5/2005 |
| WO | WO-2005/060999 A2 | 7/2005 |
| WO | WO-2005/060999 A3 | 7/2005 |
| WO | WO-2005/060999 C1 | 7/2005 |
| WO | WO-2005/061542 A2 | 7/2005 |
| WO | WO-2005/061542 A3 | 7/2005 |
| WO | WO-2005/070963 A1 | 8/2005 |
| WO | WO-2005/103081 A2 | 11/2005 |
| WO | WO-2005/103081 A3 | 11/2005 |
| WO | WO-2005/108989 A2 | 11/2005 |
| WO | WO-2005/108989 A3 | 11/2005 |
| WO | WO-2005/113003 A2 | 12/2005 |
| WO | WO-2005/113003 A3 | 12/2005 |
| WO | WO-2005/114218 A2 | 12/2005 |
| WO | WO-2005/114218 A3 | 12/2005 |
| WO | WO-2005/115453 A2 | 12/2005 |
| WO | WO-2005/115453 A3 | 12/2005 |
| WO | WO-2005/117972 A2 | 12/2005 |
| WO | WO-2005/117972 A3 | 12/2005 |
| WO | WO-2005/117978 A2 | 12/2005 |
| WO | WO-2005/117978 A3 | 12/2005 |
| WO | WO-2005/120437 A2 | 12/2005 |
| WO | WO-2005/120437 A3 | 12/2005 |
| WO | WO-2006/005477 A1 | 1/2006 |
| WO | WO-2006/012508 A2 | 2/2006 |
| WO | WO-2006/012508 A3 | 2/2006 |
| WO | WO-2006/029224 A2 | 3/2006 |
| WO | WO-2006/029224 A3 | 3/2006 |
| WO | WO-2006/029275 A2 | 3/2006 |
| WO | WO-2006/029275 A3 | 3/2006 |
| WO | WO-2006/031370 A2 | 3/2006 |
| WO | WO-2006/031370 A3 | 3/2006 |
| WO | WO-2006/041680 A2 | 4/2006 |
| WO | WO-2006/041680 A3 | 4/2006 |
| WO | WO-2006/042240 A2 | 4/2006 |
| WO | WO-2006/042240 A3 | 4/2006 |
| WO | WO-2006/064121 A2 | 6/2006 |
| WO | WO-2006/064121 A3 | 6/2006 |
| WO | WO-2006/066086 A1 | 6/2006 |
| WO | WO-2006/068867 A1 | 6/2006 |
| WO | WO-2006/068867 C1 | 6/2006 |
| WO | WO-2006/069403 A2 | 6/2006 |
| WO | WO-2006/069403 A3 | 6/2006 |
| WO | WO-2006/076651 A2 | 7/2006 |
| WO | WO-2006/076651 A3 | 7/2006 |
| WO | WO-2006/084264 A2 | 8/2006 |
| WO | WO-2006/084264 A3 | 8/2006 |
| WO | WO-2006/093923 A2 | 9/2006 |
| WO | WO-2006/093923 A3 | 9/2006 |
| WO | WO-2006/093923 C1 | 9/2006 |
| WO | WO-2006/093923 C2 | 9/2006 |
| WO | WO-2006/106959 A1 | 10/2006 |
| WO | WO-2006/113308 A1 | 10/2006 |
| WO | WO-2006/113308 C1 | 10/2006 |
| WO | WO-2006/116369 A2 | 11/2006 |
| WO | WO-2006/116369 A3 | 11/2006 |
| WO | WO-2006/125140 A2 | 11/2006 |
| WO | WO-2006/125140 A3 | 11/2006 |
| WO | WO-2006/125140 C1 | 11/2006 |
| WO | WO-2006/126069 A2 | 11/2006 |
| WO | WO-2006/126069 A3 | 11/2006 |
| WO | WO-2006/127517 A2 | 11/2006 |
| WO | WO-2006/127517 A3 | 11/2006 |
| WO | WO-2006/130458 A2 | 12/2006 |
| WO | WO-2006/130458 A3 | 12/2006 |
| WO | WO-2006/133148 A2 | 12/2006 |
| WO | WO-2006/133148 A3 | 12/2006 |
| WO | WO-2007/014238 A2 | 2/2007 |
| WO | WO-2007/014238 A3 | 2/2007 |
| WO | WO-2007/014238 C1 | 2/2007 |
| WO | WO-2007/059188 A1 | 5/2007 |
| WO | WO-2007/062090 A2 | 5/2007 |
| WO | WO-2007/062090 A3 | 5/2007 |
| WO | WO-2007/062090 C1 | 5/2007 |
| WO | WO-2007/064911 A1 | 6/2007 |
| WO | WO-2007/140371 A2 | 12/2007 |
| WO | WO-2007/140371 A3 | 12/2007 |
| WO | WO-2007/140371 C1 | 12/2007 |
| WO | WO-2008/003319 A1 | 1/2008 |
| WO | WO-2008/030368 A1 | 3/2008 |
| WO | WO-2008/122007 A1 | 10/2008 |
| WO | WO-2008/157282 A1 | 12/2008 |
| WO | WO-2009/009523 A2 | 1/2009 |
| WO | WO-2009/009523 A3 | 1/2009 |
| WO | WO-2009/030368 A1 | 3/2009 |
| WO | WO-2009/040268 A1 | 4/2009 |
| WO | WO-2009/049841 A1 | 4/2009 |
| WO | WO-2009/053038 A2 | 4/2009 |
| WO | WO-2009/053038 A3 | 4/2009 |
| WO | WO-2009/058812 A1 | 5/2009 |
| WO | WO-2009/080541 A1 | 7/2009 |
| WO | WO-2009/085765 A1 | 7/2009 |
| WO | WO-2009/086072 A2 | 7/2009 |
| WO | WO-2009/086072 A3 | 7/2009 |
| WO | WO-2009/118142 A1 | 10/2009 |
| WO | WO-2009/134738 A1 | 11/2009 |
| WO | WO-2010/033587 A2 | 3/2010 |
| WO | WO-2010/033587 A3 | 3/2010 |
| WO | WO-2010/057107 A1 | 5/2010 |
| WO | WO-2010/057109 A1 | 5/2010 |

OTHER PUBLICATIONS

Anderson, W.F. (May 8, 1992). "Human Gene Therapy," *Science* 256:808-813.

Andersson, M. et al.(2002). "Multiple MAG Peptides are Recognized by Circulating T and B Lymphocytes in Polyneuropathy and Multiple Sclerosis," *Eur J Neurol* 9:243-251.

Anolik, J.H. et al. (Oct. 27, 2002). "B Lymphocyte Depletion in the Treatment of Systemic Lupus (SLE): Phase III Trial of Rituximab (RITUXAN®) in SLE," presented in ACR/ARHP Poster Session B, Oct. 27, 2002, Abstract No. 717, *Arthritis and Rheumatism* 46(9): S289.

Barclay, A.N. et al. ed. (1997). *The Leukocyte Antigen Facts Book*, 2nd Edition, ed. Academic Press, Harcourt Brace & Co.: New York, New York, pp. v-vi. (Table of Contents Only.)

Bar-Or, A. et al. (Mar. 2008). "Rituximab in Relapsing-Remitting Multiple Sclerosis: A 72-Week, Open Label Phase I Trial," *Ann Neurol* 63(3):395-400.

Berger, T et al. (Jul. 10,2003). "Antimyelin Antibodies by as a Predictor of Clinically Definite Multiple Sclerosis After a First Demyelinating Event," *N Engl J Med* 349(2):139-145.

Bielekova, B. et al. (Oct. 2000). "Encephalitogenic Potential of the Myelin Basic Protein Peptides (Amino Acids 83-99) in Multiple Sclerosis: Results of a Phase II Clinical Trial With an Altered Peptides Ligand," *Nat Med* 6(10):1167-1175.

Brennan, M. et al. (Jul. 5, 1985). "Preparation of Bispecific Antibodies by Chemical Recombination of Monoclonal Immunglobulin $G_1$ Fragments," *Science* 229:81-83.

Brodeur, B.R. et al. (1987). "Mouse-Human Myeloma Partners for the Production of Heterohybridomas," Chapter 4 in *Monoclonal Antibody Production Techniques and Applications*, Schook, L.B. ed., Marcel Dekker, Inc., New York, New York, pp. 51-63.

Brüggermann, M. et al. (1993). "Designer Mice: The Production of Human Antibody Repertoires in Transgenic Animals," *Year in Immuno.* 7:33-40.

Capel, P.J.A. et al. (1994). "Heterogeneity of Human IgG Fc Receptors," *Immunomethods* 4:25-34.

(56) References Cited

OTHER PUBLICATIONS

Caron, P.C. et al. (Oct. 1992). "Engineered Humanized Dimeric Forms of IgG Are More Effective Antibodies," *J. Exp Med.* 176:1191-1195.

Carter, P. et al. (May 1992). "Humanization of an Anti-p185HER2 Antibody for Human Cancer Therapy," *Proc. Natl. Acad. Sci. USA* 89:4285-4289.

Carter, P. et al. (Feb. 1992). "High Level *Escherichia coli* Expression and Production of a Bivalent Humanized Antibody Fragment," *Bio-Technology* 10:163-167.

Cepok, S. et al. (2001). "Patterns of Cerebrospinal Fluid Pathology Correlate With Disease Progression in Multiple Sclerosis," *Brain* 124(Pt 11):2169-2176.

Chari, R.V.J. et al. (Jan. 1, 1992). "Immunoconjugates Containing Novel Maytansinoids: Promising Anticancer Drugs," *Cancer Research* 52:127-131.

Chothia, C. et al. (1987). "Canonical Structures for the Hypervariable Regions of Immunoglobulins," *J. Mol. Biol.* 196:901-917.

Clark, E.A. et al. (Mar. 1985). "Role of the Bp35 Cell Surface Polypeptide in Human B-Cell Activation," *Proc. Natl. Acad. Sci. USA* 82:1766-1770.

Clackson, T. et al. (Aug. 15, 1991). "Making Antibody Fragments Using Phage Display Libraries," *Nature* 352:624-628.

Clynes, R. et al. (Jan. 1998). "Fc Receptors are Required in Passive and Active Immunity to Melanoma," *Proc. Natl. Acad. Sci. USA* 95:652-656.

Confavreux, C. et al. (Nov. 16, 2000). "Relapses and Progression of Disability in Multiple Sclerosis," *N. Engl. J. Med.* 343(20):1430-1438.

Cragg, M.S. et al. (Feb. 1, 2003). "Complement-Mediated Lysis by Anti-CD20 mAb Correlates with Segregation Into Lipids Rafts," *Blood* 101(3):1045-1052.

Cree, B. et al. (Apr. 29, 2004). "Tolerability and Effects of Rituximab "Anti-CD20 Antibody" in Neuromyelitis Optica and Rapidly Worsening Multiple Sclerosis" Meeting of the Am. Acad. Neurol., San Francisco, CA, Apr. 29, 2004, one page.

Cree, B.A.C. et al. (Apr. 2005). "An Open Label Study of the Effects of Rituximab in Neuromyelitis Optica," *Neurology* 64(7):1270-1272.

Cross, A.H. et al. (Oct. 2003). "Preliminary Results from a Phase II Trial of Rituximab in MS," (abstract) Eighth Annual Meeting of the Americas Committees for Research and Treatment in Multiple Sclerosis ACTRIMS, San Francisco, CA, Oct. 19, 2003, pp. 20-21.

Cross, A.H. et al. (2006). "Rituximab Reduces B Cells and T Cells in Cerebrospinal Fluid of Multiple Sclerosis Patients," *J. Neuroimmunol.* 180(1-2):63-70.

Cunningham, B.C. et al. (Mar. 10, 1989). "Receptor and Antibody Epitopes in Human Growth Hormone Identified by Homolog-Scanning Mutagenesis," *Science* 243:1330-1336.

Daeron, M. (1997). "Fc Receptor Biology," *Annu. Rev. Immunol.* 15:203-234.

D'Arena, G. et al. (2003). "Late and Long-Lasting Response in an Adult Chronic Idiopathic Thrombocytopenic Purpura After Extend Course of Rituximab," *Leuk. Lymphoma* 44(3):561-562.

De Haas, M. et al. (Oct. 1995). "Fcγ Receptors of Phagocytes," *J. Lab. Clin. Med.* 126(4):330-341.

De Vita, S. et al. (Aug. 2002). "Efficacy of Selective B Cell Blockade in the Treatment of Rheumatoid Arthritis. Evidence for a Pathogenetic Role of B Cells," *Arthritis & Rheum.* 46(8):2029-2033.

Demidem, A. et al. (1997). "Chimeric Anti-CD20 (IDEC-C2B8) Monoclonal Antibody Sensitizes a B Cell Lymphoma Cell Line to Cell Killing by Cytotoxic Drugs," *Cancer Chemotherapy & Radiopharmaceuticals* 12(3):177-186.

Doran, M.F. et al. (2002). "Frequency of Infection in Patients With Rheumatoid Arthritis Compared With Controls," *Arthritis Rheum.* 46(9):2287-2293.

Edwards, J.C.W. et al. (2001). "Sustained Improvement in Rheumatoid Arthritis Following a Protocol Designed to Deplete B Lymphocytes," *Rheumatology* 40:205-211.

Edwards, J.C.W. et al. (2002). "B-Lymphocyte Depletion Therapy in Rheumatoid Arthritis and Other Autoimmune Disorders," *Biochem. Soc. Trans.* 30(Part 4):824-828.

Edwards, J.C.W. et al. (Oct. 26, 2002). "Efficacy and Safety of Rituximab, a B-Cell Targeted Chimeric Monoclonal Antibody: A Randomized, Placebo-Controlled Trial in Patients With Rheumatoid Arthritis," *Arthritis and Rheumatism* 46(9):S197, Abstract No. 446.

Egg, R. et al. (2001). "Anti-MOG and Anti-MBP Antibody Subclasses in Multiple Sclerosis," *Mult. Scler.* 7(5):285-289.

Einfeld, D.A. et al. (1988). "Molecular Cloning of the Human B Cell CD20 Receptor Predicts a Hydrophobic Protein with Multiple Transmembrane Domains," *EMBO J.* 7(3):711-717.

Eisenberg, R. (Apr. 15, 2003). "Rituximab in Lupus," *Arthritis Res. Ther.* 5(4):157-159.

Emery, P. et al. (Oct. 26, 2003). "Sustained Efficacy at 48 Weeks After Single Treatment Course of Rituximab in Patients with Rheumatoid Arthritis," *Arthritis Rheum.* 48(9):S439.

Eppstein, D.A. et al. (Jun. 1985). "Biological Activity of Liposome-Encapsulated Murine Interferon γ is Mediated by a Cell Membrane Receptor," *Proc. Natl. Acad. Sci. USA* 82:3688-3692.

Esiri, M. M. (1980). "Multiple Sclerosis: A Quantitative and Qualitative Study of Immunoglobulin-Containing Cells in the Central Nervous System," *Neuropathol. Appl. Neurobiol.* 6:9-21.

Filippini, G. et al. (Feb. 15, 2003). "Interferons in Relapsing Remitting Multiple Sclerosis: A Systematic Review," *Lancet* 361:545-552.

Gabizon, A. et al. (Oct. 4, 1989). "Pharmacokinetics and Tissue Distribution of Doxorubicin Encapsulated in Stable Liposomes With Long Circulation Times," *J. National Cancer Inst.* 81(19)1484-1488.

Gazzano-Santoro, H. et al. (1996). "A Non-Radioactive Complement-Dependent Cytotoxicity Assay for Anti-CD20 Monoclonal Antibody," *J. Immunol. Methods* 202:163-171.

Genain, C.P. et al. (Feb. 1999). "Identification of Autoantibodies Associated with Myelin Damage in Multiple Sclerosis," *Nat. Med.* 5(2):170-175.

Glennie, M.J. et al. (Jun. 2003). "Renaissance of Cancer Therapeutic Antibodies," *Drug Discovery Today* 8(11):503-510.

Goding, J.W. (1986). "Production of Monoclonal Antibodies," Chapter 3 in *Monoclonal Antibodies: Principles and Practice*, Academic Press, pp. 59-103.

Griffiths, A.D. et al. (1993). "Human Anti-Self Antibodies with High Specificity From Phage Display Libraries," *EMBO J.* 12(2):725-734.

Grouin, J-M. et al. (2005). "Subgroup Analyses in Randomized Clinical Trials: Statistical and Regulatory Issues," *Journal of Biopharmaceutical Statistics* 15(5):869-882.

Gruber, M. et al. (1994). "Efficient Tumor Cell Lysis Mediated by a Specific Single Chain Antibody Expressed in *Escherichia coli*," *J. Immunol.* 152:5368-5374.

Guyer, R.L. et al. (Aug. 1976). "Immunoglobulin Binding by Mouse Intestinal Epithelial Cell Receptors," *J. Immunol.* 117(3):587-593.

Hainsworth, J.D. et al. (Oct. 15, 2002). "Rituximab as a First-Line and Maintenance Therapy for Patients With Indolent Non-Hodgkin's Lymphoma," *J. Clin. Oncol.* 20(20):4261-4267.

Hainsworth, J.D. et al. (May 1, 2003). "Single-Agent Rituximab as First-Line and Maintenance Treatment for Patients With Chronic Lymphocytic Leukemia or Small Lymphocytic Lymphoma: A Phase II Trial of the Minnie Pearl Cancer Research Network," *J Clin. Oncol.* 21(9):1746-1751.

Hartung, H-P. et al. (Oct. 2009). "Bleak Prospects for Primary Progressive Multiple Sclerosis Therapy: Downs and Downs, but a Glimmer of Hope," *Annals of Neurology* 66(4):429-432.

Hauser, S.L. et al. (Feb. 14, 2008). "B-cell Depletion With Rituximab in Relapsing-Remitting Multiple Sclerosis," *New England Journal of Medicine* 358(7):676-688.

Hawker, K. (Apr. 1, 2008). "B-cell Targeted Treatment for Multiple Sclerosis Mechanism of Action and Clinical Data," *Current Opinion in Neurology* 21(Suppl. 1):S19-S25.

Hawker, K. et al. (2008). "Efficacy and Safety of Rituximab in Patients With Primary Progressive Multiple Sclerosis: Results of a Randomized, Double-Blind, Placebo-Controlled, Multicenter Trial," Abstract No. 78, *Multiple Sclerosis* 14:S299-S301.

(56) References Cited

OTHER PUBLICATIONS

Hawker, K. et al. (Sep. 9, 2009). "Rituximab in Patients with Primary Progressive Multiple Sclerosis Results of a Randomized Double-Blind Placebo-Controlled Multicenter Trial," *Annals of Neurology* 66(4):460-471.

Higashida, J. et al. (2002). "Treatment of DMARD-Refractory Rheumatoid Arthritis with Rituximab," Presented at the Annual Scientific Meeting of the American College of Rheumatology; Oct. 24-29; New Orleans, LA 2002, one page.

Hinman, L.M. et al. (Jul. 15, 1993). "Preparation and Characterization of Monoclonal Antibody Conjugates of the Calicheamicins: A Novel and Potent Family Antitumor and Antibiotics," *Cancer Research* 53: 3336-3342.

Holliger, P. et al. (Jul. 1993). "Diabodies: Small Bivalent and Bispecific Antibody Fragments," *Proc. Natl. Acad. Sci. USA* 90:6444-6448.

Hwang, K.J. et al. (Jul. 1980). "Hepatic Uptake and Degradation of Unilamellar Sphingomyelin-Cholesterol Liposomes: A Kinetic Study," *Proc. Natl. Acad. Sci. USA* 77(7):4030-4034.

International Search Report mailed on Jul. 1, 2010, for PCT Application No. PCT/US2009/057151, filed on Sep. 16, 2009, seven pages.

Ingle, G.T. et al. (2003, e-pub. Aug. 5, 2003). "Primary Progressive Multiple Sclerosis: A 5 Year Clinical and MR Study," *Brain* 126(Pt 11):2528-2536.

Ingle, G.T. et al. (2005). "Is Inflammation Important in Early PPMS? A Longitudinal MRI Study," *J. Neurol. Neurosurg. Psychiatry* 76(9):1255-1258.

Izquierdo, G. et al. (2002). "Intrathecal IgG Synthesis: Marker of Progression in Multiple Sclerosis Patients," *Acta Neurol. Scand.* 105:158-163.

Jakobovits, A. et al. (Mar. 1993). "Analysis of Homozygous Mutant Chimeric Mice : Deletion of the Immunoglobulin Heavy-Chain Joining Region Blocks B-Cell Development and Antibody Production," *Proc. Natl. Acad. Sci. USA* 90:2551-2555.

Jakobovits, A. et al. (Mar. 18, 1993). "Germ-Line Transmission and Expression of Human-Derived Yeast Artificial Chromosome," *Nature* 362:255-258.

Janeway, C.A. (Oct. 12, 1989). "Immunotherapy by Peptides," *Nature* 341:482-483.

Johnson, K.S. et al. (1993). "Human Antibody Engineering," *Current Opinion in Structural Biology* 3:564-571.

Jones, P.T. et al. (May 29, 1986). "Replacing the Complementarity-Determining Regions in a Human Antibody With Those From a Mouse," *Nature* 321:522-525.

Kabat, E.A. et al. (1991). *Sequences of Immunological Interest*, 5th Ed. Public Health Service, National Institute of Health, Bethesda, MD, NIH Publication No. 91-3242, pp. xii-xcvi.

Kim, J-K. et al. (1994). "Localization of the Site of the Murine IgG1 Molecule That is Involved in Binding to the Murine Intestinal Fc Receptor," *Eur. J. Immunol.* 24:2429-2432.

Köhler, G. et al. (Aug. 7, 1975). "Continuous Cultures of Fused Cells Secreting Antibodies of Predefined Specificity," *Nature* 256:495-497.

Kostelny, S.A. et al. (Mar. 1, 1992). "Formation of Bispecific Antibody by the Use of Leucine Zippers," *J. Immunol.* 148(5):1547-1553.

Kozbor, D. et al. (Dec. 1984). "A Human Hybrid for Production of Human Monoclonal Antibodies," *J. Immunol.* 133(6):3001-3005.

Kremenchutzky, M. et al. (Mar. 2006, e-pub. Jan. 9, 2006). "The Natural History of Multiple Sclerosis: a Geographically Based Study 9: Observations on the Progressive Phase of the Disease," *Brain* 129(Pt 3):584-594.

Kremenchutzky, M. et al. (1999). "The Natural History of Multiple Sclerosis: A Geographically Based Study. 7. Progressive Relapsing and Relapsing-Progressive Multiple Sclerosis. A Reevaluation," *Brain* 122 (Pt 10):1941-1950.

Kurtzke, J.F. (Nov. 1983). "Rating Neurologic Impairment in Multiple Sclerosis: An Expanded Disability Scale (EDSS)," *J. Neurology* 33(11):1444-1452.

Leandro, M.J. et al. (2001). "Lymphocyte Depletion in Rheumatoid Arthritis: Early Evidence for Safety, Efficacy and Dose Response," *Arthritis and Rheumatism* 44(9):S370.

Leandro, M.J. et al. (2002). "Clinical Outcome in 22 Patients With Rheumatoid Arthritis Treated With B Lymphocyte Depletion" *Ann. Rheum. Dis.* 61:883-888.

Leandro, M.J. et al. (Oct. 2002). "An Open Study of B Lymphocyte Depletion in Systemic Lupus Erythematosus," *Arthritis & Rheumatism* 46(10):2673-2677.

Lehninger. (1975). *Biochemistry*, second ed., pp. 73-75, Worth Publishers, New York, New York.

Levine, T.D. et al. (May 1999). "IgM Antibody-Related Polyneuropathies: B-Cell Depletion Chemotherapy Using Rituximab," *Neurology* 52:1701-1704.

Lode, H.N. et al. (Jul. 15, 1998). "Targeted Therapy With a Novel Enediyne Antibiotic Calicheamicin $\ominus^1$ Effectively Suppresses Growth and Dissemination of Liver Metastases in a Syngeneic Model of Murine Neuroblastoma," *Cancer Research* 58:2925-2928.

Lucchinetti, C. et al. (Feb. 22, 2000). "Heterogeneity of Multiple Sclerosis Lesions: Implications for the Pathogenesis of Demyelination," *Ann. Neurol.* 47:707-717.

Maloney, D.G. et al. (1996). "The Anti-Tumor Effect of Monoclonal Anti-CD20 Antibody (mAb) Therapy Includes Direct Anti-Proliferative Activity and Induction of Apoptosis in CD20 Positive Non-Hodgkin's Lymphoma (NHL) Cell Lines," *Blood* 88(10):637a.

Marks, J.M. et al. (1991). "By-Passing Immunization. Human Antibodies from V-Gene Libraries Displayed on Phage," *J. Mol. Biol.* 222:581-597.

Marks, J.M. et al. (Jul. 1992). "By_-Passing Immunization: Building High Affinity Human Antibodies by Chain Shuffling," *Bio-Technology* 10:779-783.

Martin, F.J. et al. (Jan. 10, 1982). "Irreversible Coupling of Immunoglobulin Fragments to Preformed Vesicles. An Improved Method for Liposome Targeting," *J. Biol. Chem.* 257:286-288.

Martin, F. et al. (May 2004). "Pathogenic Roles of B Cells in Human Autoimmunity: Insights From the Clinic" *Immunity* 20:517-527.

Massey, R.J. (Jul. 20, 1987). "Catalytic Antibodies Catching On," *Nature* 328:457-458.

Matá, S. et al. (1999). "Multiple Sclerosis is Associated With Enhanced B Cell Responses to the Ganglioside GD I a," *Mult. Scler.* 5:379-388.

Matthews, R. (Apr. 7, 2001). "Medical Heretics," *New Scientist* pp. 34-37.

McCafferty, J. et al. (Dec. 6, 1990). "Phage Antibodies: Filamentous Phage Displaying Antibody Variable Domains," *Nature* 348:552-554.

McDonald, W.I. et al. (2001). "Recommended Diagnostic Criteria for Multiple Sclerosis: Guidelines From the International Panel on the Diagnosis of Multiple Sclerosis," *Ann. Neurol.* 50:121-127.

Millstein, C. et al. (Oct. 6, 1983). "Hybrid Hybridomas and Their Use in Immunohistochemistry," *Nature* 305:537-539.

Monson, N.L. et al. (Feb. 1, 2005). "Effect of Rituximab on the Peripheral Blood and Cerebrospinal Fluid B Cells in Patients with Primary Progressive Multiple Sclerosis," *Archives of Neurology* 62(2):258-264.

Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.

Morrison, S.L. et al. (Nov. 1984). "Chimeric Human Antibody Molecules: Mouse Antigen-Binding Domains With Human Constant Region Domains," *Proc. Natl. Acad. Sci. USA* 81:6851-6855.

Munson, P.J. et al. (1980). "LIGAND: A Versatile Computerized Approach for Characterization of Ligand-Binding Systems," *Anal. Biochem.* 107:220-239.

Neuberger, M.S. et al. (Dec. 13, 1984). "Recombinant Antibodies Possessing Novel Effector Functions," *Nature* 312:604-608.

Neurology. (Aug. 1, 1999). "TNF Neutralization in MS: Results of a Randomized Placebo Controlled Multicenter Study," *Neurology* 53:457-465.

Nicolaou, K.C. et al. (1994). "Calicheamicin $\ominus 1$ : A Rationally Designed Molecule with Extremely Potent and Selective DNA

(56) References Cited

OTHER PUBLICATIONS

Cleaving Properties and Apoptosis Inducing Activity," *Angew. Chem. Intl. Ed. Engl.* 33(2):183-186.
Noonan, C.W. et al.(2002). "Prevalence Estimates for MS in the United States and Evidence of an Increasing Trend for Women," *Neurology* 58:136-138.
O'Connor, P. et al. (Sep. 2002). "Key Issues in the Diagnosis and Treatment of Multiple Sclerosis," *Neurology* 59:S1-S33.
Offner, H. et al. (Jan. 25, 1991). "T Cell Receptor Peptide Therapy Triggers Autoregulation of Experimental Encephalomyelitis," *Science* 251:430-432.
Okazaki, A. et al. (Mar. 2004). "Fucose Depletion From Human IgG1 Oligosaccharide Enhances Binding Enthalpy and Association Rate Between IgG1 and FcγRIIIa," *J. Mol. Biol.* 336(5):1239-1249.
Pennica, D. et al. (Dec. 20-27, 1984). "Human Tumour Necrosis Factor: Precursor Structure, Expression and Homology to Lymphotoxin," *Nature* 312(5995):724-729.
Perotta, A. et al. (1998). "Response of Chronic Relapsing ITP of 10 Years duration to Rituximab," *Blood* 10(1)(part 1-2):p. 88B, Abstract No. 3360.
Pestronk, A. et al. (2003). "Treatment of IgM Antibody Associated Polyneuropathies Using Rituximab," *J Neurol Neurosurg Psychiatry* 74:485-489.
Petereit, H-F. et al. (Oct. 1, 2006). "Effective Suppression of Cerebrospinal Fluid B Cells by Rituximab and Cyclophosphamide in Progressive Multiple Sclerosis," *Archives of Neurology* 62(10):1641-1642.
Plückthun, A. (1992). "Mono- and Bivalent Antibody Fragments Produced in *Escherichia coli*: Engineering, Folding and Antigen Binding," *Immunol. Revs.* 130:151-188.
Plückthun, A. (1994). "Antibodies From *Escherichia coli*," Chapter 11 in *The Pharmacology of Monoclonal Antibodies*, vol. 113, Rosenburg and Moore eds., Springer-Verlag, New York, NY, pp. 269-315.
Pranzatelli, M.R. et al. (Mar. 2003). "CSF B-Cell Over-Expansion in Paraneoplastic Opsoclonus-Myoclonus: Effect of Rituximab, an Anti-B-Cell Monoclonal Antibody," *Neurology* 60(Suppl 1) PO5.128:A395.
Press, O.W. et al. (Feb. 1987). "Monoclonal Antibody 1F5 (Anti-CD20) Serotherapy of Human B Cell Lymphomas," *Blood* 69(2):584-591.
Presta, L. G. (1992). "Antibody Engineering," *Curr. Op. Struct. Biol.* 2:593-596.
Presta, L.G. et al. (Sep. 1, 1993). "Humanization of an Antibody Directed Against Ag," *J. Immunol.* 151(5):2623-2632.
Prineas, J.W. et al. (1978). "Macrophages, Lymphocytes, and Plasma Cells in the Perivascular Compartment in Chronic Multiple Sclerosis," *Lab Invest* 3(4)8:409-421.
Ravetch, J.V. et al. (1991). "Fc Receptors," *Annu. Rev. Immunol* 9:457-492.
Reff, ME. et al. (Jan. 15, 1994). "Depletion of B Cell in Vivo by a Chimeric Mouse Human Monoclonal Antibody to CD20," *Blood* 83(2):435-445.
Reindl, M. et al. (1999). "Antibodies Against the Myelin Oligodendrocyte Glycoprotein and the Myelin Basic Proteins in Multiple Sclerosis and Other Neurological Diseases: A Comparative Study," *Brain* 122:2047-2056.
Remington. (1980). *Remington's Pharmaceutical Sciences*, 16th edition, Osol, A. ed., table of contents, p. xiii.
Riechmann, L. et al. (Mar. 24, 1988). "Reshaping Human Antibodies for Therapy," *Nature* 332:323-327.
Ripka, J. et al. (Sep. 1986). "Two Chinese Hamster Ovary Glycosylation Mutants Affected in the Conversion of GDP-Mannose to GDP-Fucose," *Arch. Biochem. Biophys.* 249(2):533-545.
Roxburgh, R.H.S.R. et al. (1995). "Multiple Sclerosis Severity Score. Using Disability and Disease Duration to Rate Disease Severity," *Neurology* 64: 1144-1151.
Rudick, R.A. et al. (1995). "Multiple Sclerosis Progression in a Natural History Study: Predictive Value of Cerebrospinal Fluid Free Kappa Light Chains," *Mult. Scler.* 1:150-155.

Sadatipour, B.T. et al. (1998). "Increased Circulating Antiganglioside Antibodies in Primary and Secondary Progressive Multiple Sclerosis," *Ann. Neurol.* 44:980-983.
Sastre-Garriga, J. et al. (2005). "Long-Term Clinical Outcome of Primary Progressive MS: Predictive Value of Clinical and MRI Data," *Neurology* 65(4):633-635.
Shopes, B. (May 1, 1992). "A Genetically Engineered Human IgG Mutant With Enhanced Cytolytic Activity," *J. Immunol.* 148(9):2918-2922.
Siden, Å. (1979). "Isoelectric Focusing and Crossed Immunoelectrofocusing of CSF Immunoglobulins in MS," *J. Neurol.* 221:39-51.
Sims, M.J. et al. (Aug. 15, 1993). "A Humanized CD18 Antibody Can Block Function Without Cell Destruction," *J. Immunol.* 151(4):2296-2308.
Skerra, A. (1993). "Bacterial Expression of Immunoglobulin Fragments," *Curr. Opinion in Immunol.* 5:256-262.
Specks, U. et al. (Dec. 2001). "Response of Wegener's Granulomatosis to Anti-CD20 Chimeric Monoclonal Antibody Therapy" *Arthritis & Rheumatism* 44(12):2836-2840.
Stasi, R. et al. (Aug. 15, 2001). "Rituximab Chimeric Anti-CD20 Monoclonal Antibody Treatment for Adults With Chronic Idiopathic Thrombocytopenic Purpura," *Blood* 98(4):952-957.
Stevenson, G.T. et al. (1989). "A Chimeric Antibody With Dual Fc Regions (bisFabFc) Prepared by Manipulations at the IgG Hinge," *Anti-Cancer Drug Design* 3:219-230.
Stüve, O. et al. (Sep. 2002). "Approved and Future Pharmacotherapy for Multiple Sclerosis," *Neurologist* 8(5):290-301.
Suresh, M.R. et al. (1986). "Bispecific Monoclonal Antibodies From Hybrid Hybridomas," Chapter 17 in *Methods in Enzymology*, Academic Press, 121:210-228.
Szczepanski, L. et al. (2003). "Safety Data From 48 Weeks Follow-Up of a Randomised Controlled Trail of Rituximab in Patents with Rheumatoid Arthritis," *Arthritis Rheum.* 48(9):S121.
Tedder, T.F. et al. (Aug. 1985). "The B Cell Surface Molecule B1 is Functionally Linked With B Cell Activation and Differentiation," *J. Immunol.* 135(2):973-979.
Tedder, T.F. et al. (1990). "The CD20 Surface Molecule of B Lymphocytes Functions as a Calcium Channel," *J. Cell. Biochem.* 14D:195, Abstract M023.
Traunecker, A. et al. (1991). "Bispecific Single Chain Molecules (Janusins) Target Cytotoxic Lymphocytes on HIV Infected Cells," *EMBO J.* 10(12):3655-3659.
Tremlett, H. et al. (Dec. 27, 2005). "The Natural History of Primary Progression in British Columbia, Canada," *Neurology* 65(12):1919-1923.
Tremlett, H. et al. (2008). "Natural History of Secondary-Progressive Multiple Sclerosis," *Mult. Scler.* 14(3):314-324.
Tuscano, J.M. "Successful Treatment of Infliximab-Refractory Rheumatoid Arthritis With Rituximab" Presented at the Annual Scientific Meeting of the American College of Rheumatology, Oct. 24-29, 2002, New Orleans, LA, one page.
Tutt, A. et al. (Jul. 1, 1991). "Trispecific F(ab')₃ Derivatives That Use Cooperative Signaling Via the TCR/CD3 Complex and CD2 to Activate and Redirect Resting Cytotoxic T Cells," *Immunol.* 147(1):60-69.
Valentine, M.A. et al. (1987). "Structures and Function of the B-Cell Specific 35-37 kDa CD20 Protein," Chapter B3.9 in *Leukocyte Typing III*, McMichael ed., Oxford University Press, pp. 440-443.
Valentine, M.A. et al. (Jul. 5, 1989). "Phosphorylation of the CD20 Phosphoprotein in Resting B Lymphocytes," *J. Biol. Chem.* 264(19):11282-11287.
Verhoeyen, M. et al.(Mar. 25, 1988). "Reshaping Human Antibodies: Grafting an Antilysozyme Activity," *Science* 239:1534-1536.
Villar, L.M. et al. (Feb. 2003). "Intrathecal IgM Synthesis Is a Prognostic Factor in Multiple Sclerosis," *Ann. Neurol.* 53(2):222-226.
Vitetta, E.S. et al. (Nov. 20, 1987). "Redesigning Nature's Poisons to Create Anti-Tumor Reagents," *Science* 238:1098-1104.
Wagner, E. et al. (May 1990). "Transferrin-Polycation Conjugates as Carriers for DNA Uptake Into Cells," *Proc. Natl. Acad. Sci. USA* 87:3410-3414.

(56) References Cited

OTHER PUBLICATIONS

Wang, R. et al. (Nov. 22, 2007). "Statistics in Medicine—Reporting of Subgroup Analyses in Clinical Trials," *New England Journal of Medicine* 357(21):2189-2194.

Waterhouse, P. et al. (1993). "Combinatorial Infection and in vivo Recombination: A Strategy for Making Large Phage Antibody Repertoires," *Nuc. Acids. Res.* 21(9):2265-2266.

Weinshenker, B.G. et al. (1989). "The Natural History of Multiple Sclerosis: A Geographically Based Study," *Brain* 112(Pt 1):133-146.

Wingerchuk, D.M. et al. (2001). "Multiple Sclerosis: Current Pathophysiological Concepts," *Lab. Invest.* 81(3):263-281.

Wolff, E.A. et al. (Jun. 1, 1993). "Monoclonal Antibody Homodimers: Enhanced Antitumor Activity in Nude Mice," *Cancer Research* 53:2560-2565.

Wolinsky J.S. et al. (2003). "The Diagnosis of Primary Progressive Multiple Sclerosis," *J. Neurol. Sci.* 206:145-152.

Wolinsky, J.S. et al. (Jan. 2007). "Glatiramer Acetate in Primary Progressive Multiple Sclerosis: Results of a Multinational, Multicenter, Double-Blind, Placebo-Controlled Trial," *Annals of Neurology* 61(1):14-24.

Written Opinion mailed on Jul. 1, 2010, for PCT Application No. PCT/US2009/057151, filed on Sep. 16, 2009, eleven pages.

Wu, G.Y. et al. (Apr. 5, 1987). "Receptor-Mediated in Vitro Gene Transformation by a Soluble DNA Carrier System," *J. Biol. Chem.* 262(10):4429-4432.

Yamane-Ohnuki, N. et al. (Sep. 5, 2004, e-pub. Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotech. Bioeng.* 87(5):614-622.

Zaja, F. et al. (Feb. 2002). "B-Cell Depletion With Rituximab as Treatment for Immune Hemolytic Anemia and Chronic Thrombocytopenia," *Haematologica* 87:189-195.

Zeman, D. et al. (Jan.-Feb. 2001). "Cerebrospinal Fluid Cytologic Findings in Multiple Sclerosis," *Acta Cytol.* 45(1):51-59.

\* cited by examiner

Sequence Alignment of Variable Light-Chain Domain

```
              |————— FR1 —————|      CDR1       |——
                10        20          30          40
2H7       QIVLSQSPAILSASPGEKVTMTC [RASSSVS-YMH] WYQQKP
           * ***   **      * **  *
hu2H7.v16 DIQMTQSPSSLSASVGDRVTITC [RASSSVS-YMH] WYQQKP
                                   *  *  *  **
hum κI    DIQMTQSPSSLSASVGDRVTITC [RASQSISNYLA] WYQQKP FR2 ———|     CDR2    |————— FR3 —————
                50            60          70         80
2H7       GSSPKPWIY [APSNLAS] GVPARFSGSGSGTSYSLTISRVEA
           **   *                 *         ***    ****
hu2H7.v16 GKAPKPLIY [APSNLAS] GVPSRFSGSGSGTDFTLTISSLQP
              *      * * *
hum κI    GKAPKLLIY [AASSLES] GVPSRFSGSGSGTDFTLTISSLQP —————————|  CDR3    |—— FR4 ——|
                      90         100
2H7       EDAATYYC [QQWSFNPPT] FGAGTKLELKR
            *                    *   * *
hu2H7.v16 EDFATYYC [QQWSFNPPT] FGQGTKVEIKR
                    **** *
hum κI    EDFATYYC [QQYNSLPWT] FGQGTKVEIKR
```

*FIG. 1A*

Sequence Alignment of Variable Heavy-Chain Domain

```
                 |———— FR1 ————|         CDR1        |——
                 10          20         30            40
2H7         QAYLQQSGAELVRPGASVKMSCKAS [GYTFTSYNMH] WVKQT
            *** **  **  *   * ***  *                 * *
hu2H7.v16   EVQLVESGGGLVQPGGSLRLSCAAS [GYTFTSYNMH] WVRQA
                                        *   *  * *
hum III     EVQLVESGGGLVQPGGSLRLSCAAS [GFTFSSYAMS] WVRQA ——FR2—|          CDR2          |———— FR3 ————
                 50    a      60             70          80
2H7         PRQGLEWIG [AIYPGNGDTSYNQKFKG] KATLTVDKSSSTAYM
              **     *                      ** **    ** * *
hu2H7.v16   PGKGLEWVG [AIYPGNGDTSYNQKFKG] RFTISVDKSKNTLYL
              *   *  **** * * ****            * *
hum III     PGKGLEWVA [VISGDGGSTYYADSVKG] RFTISRDNSKNTLTL ——————————————|      CDR3       |—— FR4 ——|
               abc           90      100abcde             110
2H7         QLSSLTSEDSAVYFCAR [VVYYSNSYWYFDV] WGTGTTVTVSS
             **   **   *  *                      *   *
hu2H7.v16   QMNSLRAEDTAVYYCAR [VVYYSNSYWYFDV] WGQGTLVTVSS
                                ******* *** *
hum III     QMNSLRAEDTAVYYCAR [GRVGYSLY---DY] WGQGTLVTVSS
```

*FIG. 1B*

Humanized 2H7.v16 Light Chain

DIQMTQSPSSLSASVGDRVTITCRASSSVSYMHWYQQKPGKAPKPLIYAPSNLASGVPSRFSG
SGSGTDFTLTISSLQPEDFATYYCQQWSFNPPTFGQGTKVEIKRTVAAPSVFIFPPSDEQLKS
GTASVVCLLNNFYPREAKVQWKVDNALQSGNSQESVTEQDSKDSTYSLSSTLTLSKADYEKHK
VYACEVTHQGLSSPVTKSFNRGEC (SEQ ID NO:13)

*FIG. 2*

Humanized 2H7.v16 Heavy Chain

EVQLVESGGGLVQPGGSLRLSCAASGYTFTSYNMHWVRQAPGKGLEWVGAIYPGNGDTSYNQK
FKGRFTISVDKSKNTLYLQMNSLRAEDTAVYYCARVVYYSNSYWYFDVWGQGTLVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHY
TQKSLSLSPGK (SEQ ID NO:14)

*FIG. 3*

Humanized 2H7.v31 Heavy Chain

EVQLVESGGGLVQPGGSLRLSCAASGYTFTSYNMHWVRQAPGKGLEWVGAIYPGNGDTSYNQK
FKGRFTISVDKSKNTLYLQMNSLRAEDTAVYYCARVVYYSNSYWYFDVWGQGTLVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNATYRVVSVLTVLH
QDWLNGKEYKCKVSNKALPAPIAATISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHY
TQKSLSLSPGK (SEQ ID NO:15)

*FIG. 4*

Light Chain Alignment

```
              1                                                32
hu2H7.v16     DIQMTQSPSSLSASVGDRVTITCRASSSVSYMHWYQQKPGKAPKPLIYAP
              **********************************.***************
hu2H7.v511    DIQMTQSPSSLSASVGDRVTITCRASSSVSYLHWYQQKPGKAPKPLIYAP 52
hu2H7.v16     SNLASGVPSRFSGSGSGTDFTLTISSLQPEDFATYYCQQWSFNPPTFGQG
              *******************************************.********
hu2H7.v511    SNLASGVPSRFSGSGSGTDFTLTISSLQPEDFATYYCQQWAFNPPTFGQG 102
hu2H7.v16     TKVEIKRTVAAPSVFIFPPSDEQLKSGTASVVCLLNNFYPREAKVQWKVD
              **************************************************
hu2H7.v511    TKVEIKRTVAAPSVFIFPPSDEQLKSGTASVVCLLNNFYPREAKVQWKVD 152
hu2H7.v16     NALQSGNSQESVTEQDSKDSTYSLSSTLTLSKADYEKHKVYACEVTHQGL
              **************************************************
hu2H7.v511    NALQSGNSQESVTEQDSKDSTYSLSSTLTLSKADYEKHKVYACEVTHQGL 202       214
hu2H7.v16     SSPVTKSFNRGEC
              *************
hu2H7.v511    SSPVTKSFNRGEC
```

*FIG. 5*

Heavy Chain Alignment

```
             1
hu2H7.v16    EVQLVESGGGLVQPGGSLRLSCAASGYTFTSYNMHW
             ***********************************
hu2H7.v511   EVQLVESGGGLVQPGGSLRLSCAASGYTFTSYNMHW 37            52a                        82abc
hu2H7.v16    VRQAPGKGLEWVGAIYPGNGDTSYNQKFKGRFTISVDKSKNTLYLQMNSL
             *******************  ****************************
hu2H7.v511   VRQAPGKGLEWVGAIYPGNGATSYNQKFKGRFTISVDKSKNTLYLQMNSL 83            100abcde        113
hu2H7.v16    RAEDTAVYYCARVVYYSNSYWYFDVWGQGTLVTVSS
             ****************  ******************
hu2H7.v511   RAEDTAVYYCARVVYYSYRYWYFDVWGQGTLVTVSS 118
hu2H7.v16    ASTKGPSVFPLAPS
             **************
hu2H7.v511   ASTKGPSVFPLAPS 132
hu2H7.v16    SKSTSGGTAALGCLVKDYFPEPVTVSWNSGALTSGVHTFPAVLQSSGLYS
             **************************************************
hu2H7.v511   SKSTSGGTAALGCLVKDYFPEPVTVSWNSGALTSGVHTFPAVLQSSGLYS 182
hu2H7.v16    LSSVVTVPSSSLGTQTYICNVNHKPSNTKVDKKVEPKSCDKTHTCPPCPA
             **************************************************
hu2H7.v511   LSSVVTVPSSSLGTQTYICNVNHKPSNTKVDKKVEPKSCDKTHTCPPCPA 232
hu2H7.v16    PELLGGPSVFLFPPKPKDTLMISRTPEVTCVVVDVSHEDPEVKFNWYVDG
             **************************************************
hu2H7.v511   PELLGGPSVFLFPPKPKDTLMISRTPEVTCVVVDVSHEDPEVKFNWYVDG 282
hu2H7.v16    VEVHNAKTKPREEQYNSTYRVVSVLTVLHQDWLNGKEYKCKVSNKALPAP
             *******************.************************ *****
hu2H7.v511   VEVHNAKTKPREEQYNATYRVVSVLTVLHQDWLNGKEYKCKVSNAALPAP 332
hu2H7.v16    IEKTISKAKGQPREPQVYTLPPSREEMTKNQVSLTCLVKGFYPSDIAVEW
             *  ***********************************************
hu2H7.v511   IAATISKAKGQPREPQVYTLPPSREEMTKNQVSLTCLVKGFYPSDIAVEW 382
hu2H7.v16    ESNGQPENNYKTTPPVLDSDGSFFLYSKLTVDKSRWQQGNVFSCSVMHEA
             **************************************************
hu2H7.v511   ESNGQPENNYKTTPPVLDSDGSFFLYSKLTVDKSRWQQGNVFSCSVMHEA 432       447
hu2H7.v16    LHNHYTQKSLSLSPGK
             ****************
hu2H7.v511   LHNHYTQKSLSLSPGK
```

FIG. 6

Overview of the Study Design and Dosing Regimen

| Screening | Randomization | Treatment Period | | | | | | | Treatment-free Period | | |
|---|---|---|---|---|---|---|---|---|---|---|---|
| | | 96-Week Study Treatment Period (4 Treatment Cycles[1]) | | | | | | | Follow-up Period | B-cell Monitoring Period | Observation Period |
| | Group | 1st Cycle | | 2nd Cycle[2,7] | | 3rd Cycle[3,7] | | 4th Cycle[7] | 24 Weeks | Variable | 24 Weeks |
| 28 Days | | Day 1 | Day 15 | Day 1 | Day 15 | Day 1 | | Day 1 | | | |
| | A (1000 mg dose regimen) | Ocrelizumab 1000 mg i.v. | Ocrelizumab 1000 mg i.v. | Ocrelizumab 1000 mg i.v. | Placebo i.v. | Ocrelizumab 1000 mg i.v.[5] | | Ocrelizumab 1000 mg i.v.[5] | | | |
| | B (600 mg dose regimen) | Ocrelizumab 300 mg i.v. | Ocrelizumab 300 mg i.v. | Ocrelizumab 600 mg i.v. | Placebo i.v. | Ocrelizumab 600 mg i.v.[6] | | Ocrelizumab 600 mg i.v.[6] | | | |
| | C (Placebo) | Placebo i.v. | Placebo i.v. | Ocrelizumab 300 mg i.v. | Ocrelizumab 300 mg i.v. | Ocrelizumab 600 mg i.v.[6] | | Ocrelizumab 600 mg i.v.[6] | | | |
| | D[4] (Avonex) | Avonex 30 μg i.m. Every Week | | Ocrelizumab 300 mg i.v. | Ocrelizumab 300 mg i.v. | Ocrelizumab 600 mg i.v.[6] | | Ocrelizumab 600 mg i.v.[6] | | | |

1. Each treatment cycle has a duration of 24 weeks.
2. All groups will receive a dual infusion, *i.e.* two i.v. infusions separated by 14 days. To maintain the blind in groups A, B and C until database closure for the primary analysis, the dual infusion will be either ocrelizumab followed by placebo (Groups A and B) or ocrelizumab followed by ocrelizumab (Group C).
3. As of the third treatment cycle, single ocrelizumab infusion should be administered in all groups. However, patients who miss their 2nd treatment cycle dosing, will receive the dosing of the 2nd treatment cycle (two infusions separated by 14 days) during the 3rd treatment cycle.
4. Patients from Group D (Avonex) are offered to be dosed with ocrelizumab on a voluntary basis.
5. Patients will be treated with the 1000 mg dose until a preferred dose is chosen on the basis of the primary analysis, at which time investigators and ethics committees will be informed of the preferred dose. After the preferred dose has been chosen patients will receive the preferred dose (600 mg or 1000 mg) for their next treatment cycle(s).
6. Patients will be treated with the 600 mg dose until a preferred dose is chosen on the basis of the primary analysis, at which time investigators and ethics committees will be informed of the preferred dose. After the preferred dose has been chosen patients will receive the preferred dose (600 mg or 1000 mg) for their next treatment cycle(s).
7. Prior to the 2nd, 3rd and 4th dosing cycles, a clinical evaluation will be performed to ensure that the patient remains eligible for retreatment.

FIG. 7

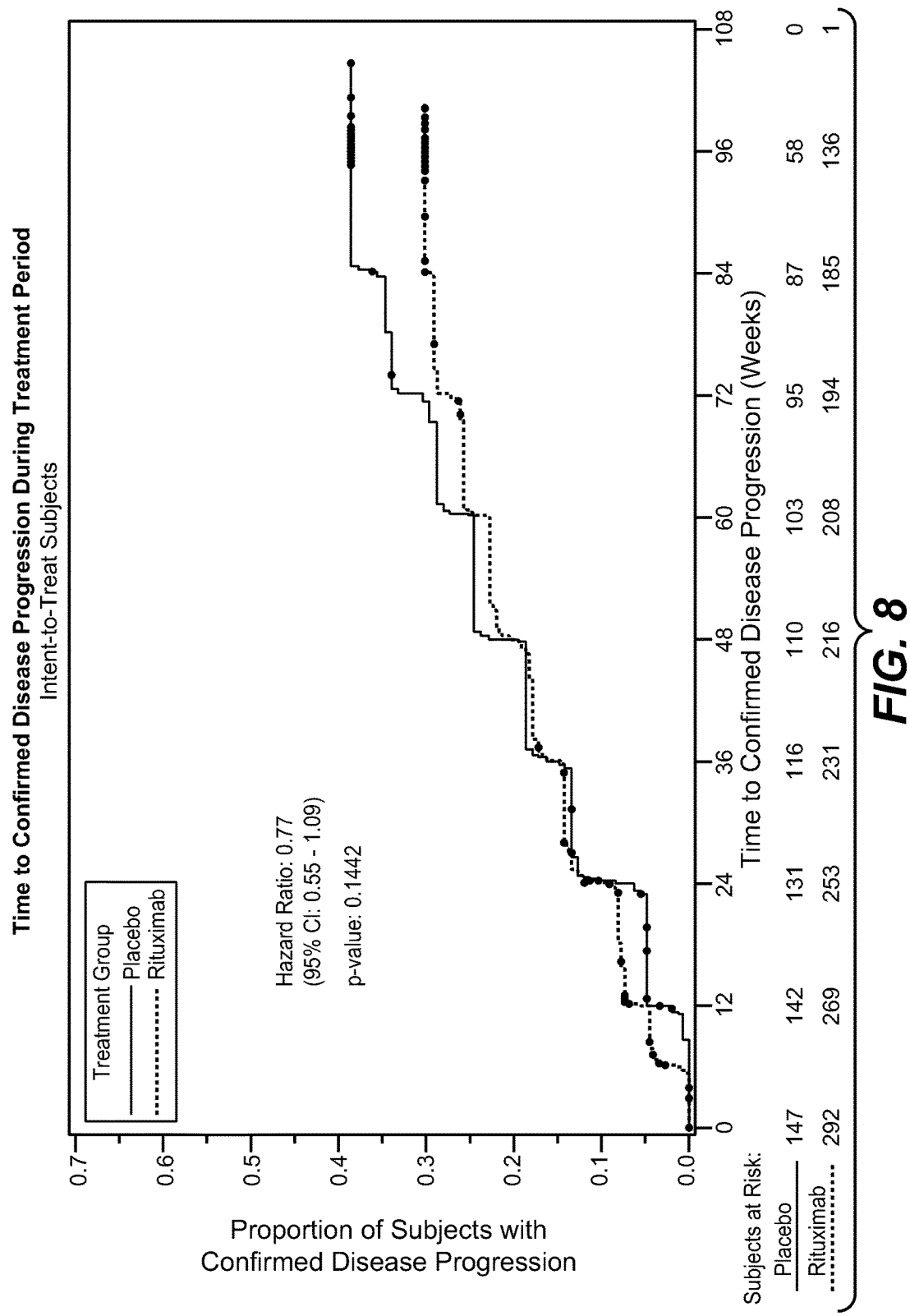

SEQUENCE LISTING

```
<160> NUMBER OF SEQ ID NOS: 25

<210> SEQ ID NO 1
<211> LENGTH: 107
<212> TYPE: PRT
<213> ORGANISM: Mus musculus

<400> SEQUENCE: 1

Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Ser Val Ser
                20                  25                  30

Tyr Met His Trp Tyr Gln Gln Lys Pro Gly Ser Ser Pro Lys Pro
                35                  40                  45

Trp Ile Tyr Ala Pro Ser Asn Leu Ala Ser Gly Val Pro Ala Arg
                50                  55                  60

Phe Ser Gly Ser Gly Ser Gly Thr Ser Tyr Ser Leu Thr Ile Ser
                65                  70                  75

Arg Val Glu Ala Glu Asp Ala Ala Thr Tyr Tyr Cys Gln Gln Trp
                80                  85                  90

Ser Phe Asn Pro Pro Thr Phe Gly Ala Gly Thr Lys Leu Glu Leu
                95                  100                 105

Lys Arg

<210> SEQ ID NO 2
<211> LENGTH: 107
```

```
<212> TYPE: PRT
<213> ORGANISM: Artificial sequence
<220> FEATURE:
<223> OTHER INFORMATION: Synthetic construct

<400> SEQUENCE: 2

Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser
                20                  25                  30

Tyr Met His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
        50                  55                  60

Phe Ser Gly Ser Gly Ser Gly Thr Asp Phe Thr Leu Thr Ile Ser
65                  70                  75

Ser Leu Gln Pro Glu Asp Phe Ala Thr Tyr Tyr Cys Gln Gln Trp
                80                  85                  90

Ser Phe Asn Pro Pro Thr Phe Gly Gln Gly Thr Lys Val Glu Ile
                95                  100                 105

Lys Arg

<210> SEQ ID NO 3
<211> LENGTH: 108
<212> TYPE: PRT
<213> ORGANISM: Artificial Sequence
<220> FEATURE:
<223> OTHER INFORMATION: Synthetic construct

<400> SEQUENCE: 3

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                  100                 105

Ile Lys Arg

<210> SEQ ID NO 4
<211> LENGTH: 10
<212> TYPE: PRT
<213> ORGANISM: Mus musculus

<400> SEQUENCE: 4

Arg Ala Ser Ser Ser Val Ser Tyr Met His
1               5                   10

<210> SEQ ID NO 5
<211> LENGTH: 7
<212> TYPE: PRT
<213> ORGANISM: Mus musculus
```

<400> SEQUENCE: 5

Ala Pro Ser Asn Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Trp Ser Phe Asn Pro Pro Thr
1               5

<210> SEQ ID NO 7
<211> LENGTH: 122
<212> TYPE: PRT
<213> ORGANISM: Mus musculus

<400> SEQUENCE: 7

Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr
                20                  25                  30

Ser Tyr Asn Met His Trp Val Lys Gln Thr Pro Arg Gln Gly Leu
            35                  40                  45

Glu Trp Ile Gly Ala Ile Tyr Pro Gly Asn Gly Asp Thr Ser Tyr
        50                  55                  60

Asn Gln Lys Phe Lys Gly Lys Ala Thr Leu Thr Val Asp Lys Ser
    65                  70                  75

Ser Ser Thr Ala Tyr Met Gln Leu Ser Ser Leu Thr Ser Glu Asp
            80                  85                  90

Ser Ala Val Tyr Phe Cys Ala Arg Val Val Tyr Tyr Ser Asn Ser
            95                  100                 105

Tyr Trp Tyr Phe Asp Val Trp Gly Thr Gly Thr Thr Val Thr Val
            110                 115                 120

Ser Ser

<210> SEQ ID NO 8
<211> LENGTH: 122
<212> TYPE: PRT
<213> ORGANISM: Artificial sequence
<220> FEATURE:
<223> OTHER INFORMATION: Synthetic construct

<400> SEQUENCE: 8

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Asp Thr Ser Tyr
        50                  55                  60

Asn Gln Lys Phe Lys Gly Arg Phe Thr Ile Ser Val Asp Lys Ser
    65                  70                  75

Lys Asn Thr Leu Tyr Leu Gln Met Asn Ser Leu Arg Ala Glu Asp
            80                  85                  90

```
Thr Ala Val Tyr Tyr Cys Ala Arg Val Val Tyr Ser Asn Ser
                 95                 100                 105

Tyr Trp Tyr Phe Asp Val Trp Gly Gln Gly Thr Leu Val Thr Val
            110                 115                 120

Ser Ser

<210> SEQ ID NO 9
<211> LENGTH: 119
<212> TYPE: PRT
<213> ORGANISM: Artificial Sequence
<220> FEATURE:
<223> OTHER INFORMATION: Synthetic construct

<400> SEQUENCE: 9

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
                35                  40                  45

Glu Trp Val Ala Val Ile Ser Gly Asp Gly Gly Ser Thr Tyr Tyr
                50                  55                  60

Ala Asp Ser Val Lys Gly Arg Phe Thr Ile Ser Arg Asp Asn Ser
                65                  70                  75

Lys Asn Thr Leu Thr Leu Gln Met Asn Ser Leu Arg Ala Glu Asp
                80                  85                  90

Thr Ala Val Tyr Tyr Cys Ala Arg Gly Arg Val Gly Tyr Ser Leu
                95                  100                 105

Tyr Asp Tyr Trp Gly Gln Gly Thr Leu Val Thr Val Ser Ser
            110                 115

<210> SEQ ID NO 10
<211> LENGTH: 10
<212> TYPE: PRT
<213> ORGANISM: Mus musculus

<400> SEQUENCE: 10

Gly Tyr Thr Phe Thr Ser Tyr Asn Met His
1               5                   10

<210> SEQ ID NO 11
<211> LENGTH: 17
<212> TYPE: PRT
<213> ORGANISM: Mus musculus

<400> SEQUENCE: 11

Ala Ile Tyr Pro Gly Asn Gly Asp Thr Ser Tyr Asn Gln Lys Phe
1               5                   10                  15

Lys Gly

<210> SEQ ID NO 12
<211> LENGTH: 13
<212> TYPE: PRT
<213> ORGANISM: Mus musculus

<400> SEQUENCE: 12

Val Val Tyr Tyr Ser Asn Ser Tyr Trp Tyr Phe Asp Val
1               5                   10

<210> SEQ ID NO 13
```

<211> LENGTH: 213
<212> TYPE: PRT
<213> ORGANISM: Artificial sequence
<220> FEATURE:
<223> OTHER INFORMATION: Synthetic construct

<400> SEQUENCE: 13

```
Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Val Ser
                20                  25                  30

Tyr Met His Trp Tyr Gln Gln Lys Pro Gly Lys Ala Pro Lys Pro
                35                  40                  45

Leu Ile Tyr Ala Pro Ser Asn Leu Ala Ser Gly Val Pro Ser Arg
                50                  55                  60

Phe Ser Gly Ser Gly Ser Gly Thr Asp Phe Thr Leu Thr Ile Ser
65                  65                  70                  75

Ser Leu Gln Pro Glu Asp Phe Ala Thr Tyr Tyr Cys Gln Gln Trp
                80                  85                  90

Ser Phe Asn Pro Pro Thr Phe Gly Gln Gly Thr Lys Val Glu Ile
                95                  100                 105

Lys Arg Thr Val Ala Ala Pro Ser Val Phe Ile Phe Pro Pro Ser
                110                 115                 120

Asp Glu Gln Leu Lys Ser Gly Thr Ala Ser Val Val Cys Leu Leu
                125                 130                 135

Asn Asn Phe Tyr Pro Arg Glu Ala Lys Val Gln Trp Lys Val Asp
                140                 145                 150

Asn Ala Leu Gln Ser Gly Asn Ser Gln Glu Ser Val Thr Glu Gln
                155                 160                 165

Asp Ser Lys Asp Ser Thr Tyr Ser Leu Ser Ser Thr Leu Thr Leu
                170                 175                 180

Ser Lys Ala Asp Tyr Glu Lys His Lys Val Tyr Ala Cys Glu Val
                185                 190                 195

Thr His Gln Gly Leu Ser Ser Pro Val Thr Lys Ser Phe Asn Arg
                200                 205                 210

Gly Glu Cys
```

<210> SEQ ID NO 14
<211> LENGTH: 452
<212> TYPE: PRT
<213> ORGANISM: Artificial sequence
<220> FEATURE:
<223> OTHER INFORMATION: Synthetic construct

<400> SEQUENCE: 14

```
Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Asp Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90
```

```
Thr Ala Val Tyr Tyr Cys Ala Arg Val Val Tyr Tyr Ser Asn Ser
                 95                 100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
                275                 280                 285

Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His
                305                 310                 315

Gln Asp Trp Leu Asn Gly Lys Glu Tyr Lys Cys Lys Val Ser Asn
                320                 325                 330

Lys Ala Leu Pro Ala Pro Ile Glu Lys Thr Ile Ser Lys Ala Lys
                335                 340                 345

Gly Gln Pro Arg Glu Pro Gln Val Tyr Thr Leu Pro Pro Ser Arg
                350                 355                 360

Glu Glu Met Thr Lys Asn Gln Val Ser Leu Thr Cys Leu Val Lys
                365                 370                 375

Gly Phe Tyr Pro Ser Asp Ile Ala Val Glu Trp Glu Ser Asn Gly
                380                 385                 390

Gln Pro Glu Asn Asn Tyr Lys Thr Thr Pro Pro Val Leu Asp Ser
                395                 400                 405

Asp Gly Ser Phe Phe Leu Tyr Ser Lys Leu Thr Val Asp Lys Ser
                410                 415                 420

Arg Trp Gln Gln Gly Asn Val Phe Ser Cys Ser Val Met His Glu
                425                 430                 435

Ala Leu His Asn His Tyr Thr Gln Lys Ser Leu Ser Leu Ser Pro
                440                 445                 450

Gly Lys

<210> SEQ ID NO 15
<211> LENGTH: 452
<212> TYPE: PRT
```

<213> ORGANISM: Artificial sequence
<220> FEATURE:
<223> OTHER INFORMATION: Synthetic construct

<400> SEQUENCE: 15

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
        35                  40                  45

Glu Trp Val Gly Ala Ile Tyr Pro Gly Asn Gly Asp Thr Ser Tyr
    50                  55                  60

Asn Gln Lys Phe Lys Gly Arg Phe Thr Ile Ser Val Asp Lys Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Asn Ser
            95                  100                 105

Tyr Trp Tyr Phe Asp Val Trp Gly Gln Gly Thr Leu Val Thr Val
        110                 115                 120

Ser Ser Ala Ser Thr Lys Gly Pro Ser Val Phe Pro Leu Ala Pro
    125                 130                 135

Ser Ser Lys Ser Thr Ser Gly Gly Thr Ala Ala Leu Gly Cys Leu
140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
        185                 190                 195

Ser Ser Leu Gly Thr Gln Thr Tyr Ile Cys Asn Val Asn His Lys
    200                 205                 210

Pro Ser Asn Thr Lys Val Asp Lys Lys Val Glu Pro Lys Ser Cys
215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp
    275                 280                 285

Gly Val Glu Val His Asn Ala Lys Thr Lys Pro Arg Glu Glu Gln
290                 295                 300

Tyr Asn Ala Thr Tyr Arg Val Val Ser Val Leu Thr Val Leu His
                305                 310                 315

Gln Asp Trp Leu Asn Gly Lys Glu Tyr Lys Cys Lys Val Ser Asn
            320                 325                 330

Lys Ala Leu Pro Ala Pro Ile Ala Ala Thr Ile Ser Lys Ala Lys
        335                 340                 345

Gly Gln Pro Arg Glu Pro Gln Val Tyr Thr Leu Pro Pro Ser Arg
    350                 355                 360

Glu Glu Met Thr Lys Asn Gln Val Ser Leu Thr Cys Leu Val Lys

```
                365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 16
<211> LENGTH: 213
<212> TYPE: PRT
<213> ORGANISM: Artificial sequence
<220> FEATURE:
<223> OTHER INFORMATION: Synthetic construct

<400> SEQUENCE: 16

Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Ser Val Ser
            20                  25                  30

Tyr Leu His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Gln Gln Trp
            80                  85                  90

Ala Phe Asn Pro Pro Thr Phe Gly Gln Gly Thr Lys Val Glu Ile
            95                  100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
            125                 130                 135

Asn Asn Phe Tyr Pro Arg Glu Ala Lys Val Gln Trp Lys Val Asp
            140                 145                 150

Asn Ala Leu Gln Ser Gly Asn Ser Gln Glu Ser Val Thr Glu Gln
            155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
            185                 190                 195

Thr His Gln Gly Leu Ser Ser Pro Val Thr Lys Ser Phe Asn Arg
            200                 205                 210

Gly Glu Cys

<210> SEQ ID NO 17
<211> LENGTH: 452
<212> TYPE: PRT
<213> ORGANISM: Artificial sequence
<220> FEATURE:
```

<223> OTHER INFORMATION: Synthetic construct

<400> SEQUENCE: 17

```
Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
        35                  40                  45

Glu Trp Val Gly Ala Ile Tyr Pro Gly Asn Gly Ala Thr Ser Tyr
    50                  55                  60

Asn Gln Lys Phe Lys Gly Arg Phe Thr Ile Ser Val Asp Lys Ser
65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Tyr Arg
        95                  100                 105

Tyr Trp Tyr Phe Asp Val Trp Gly Gln Gly Thr Leu Val Thr Val
    110                 115                 120

Ser Ser Ala Ser Thr Lys Gly Pro Ser Val Phe Pro Leu Ala Pro
125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
        155                 160                 165

Gly Ala Leu Thr Ser Gly Val His Thr Phe Pro Ala Val Leu Gln
    170                 175                 180

Ser Ser Gly Leu Tyr Ser Leu Ser Ser Val Val Thr Val Pro Ser
185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
        215                 220                 225

Asp Lys Thr His Thr Cys Pro Pro Cys Pro Ala Pro Glu Leu Leu
    230                 235                 240

Gly Gly Pro Ser Val Phe Leu Phe Pro Pro Lys Pro Lys Asp Thr
245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln
    290                 295                 300

Tyr Asn Ala Thr Tyr Arg Val Val Ser Val Leu Thr Val Leu His
305                 310                 315

Gln Asp Trp Leu Asn Gly Lys Glu Tyr Lys Cys Lys Val Ser Asn
            320                 325                 330

Ala Ala Leu Pro Ala Pro Ile Ala Ala Thr Ile Ser Lys Ala Lys
        335                 340                 345

Gly Gln Pro Arg Glu Pro Gln Val Tyr Thr Leu Pro Pro Ser Arg
    350                 355                 360

Glu Glu Met Thr Lys Asn Gln Val Ser Leu Thr Cys Leu Val Lys
365                 370                 375
```

```
Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly Lys

<210> SEQ ID NO 18
<211> LENGTH: 10
<212> TYPE: PRT
<213> ORGANISM: Artificial sequence
<220> FEATURE:
<223> OTHER INFORMATION: Synthetic construct
<220> FEATURE:
<221> NAME/KEY: Variant
<222> LOCATION: 9
<223> OTHER INFORMATION: Xaa is M or L

<400> SEQUENCE: 18

Arg Ala Ser Ser Ser Val Ser Tyr Xaa His
1               5                   10

<210> SEQ ID NO 19
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: Variant
<222> LOCATION: 4
<223> OTHER INFORMATION: Xaa is S or A

<400> SEQUENCE: 19

Gln Gln Trp Xaa Phe Asn Pro Pro Thr
1               5

<210> SEQ ID NO 20
<211> LENGTH: 17
<212> TYPE: PRT
<213> ORGANISM: Artificial sequence
<220> FEATURE:
<223> OTHER INFORMATION: Synthetic construct
<220> FEATURE:
<221> NAME/KEY: Variant
<222> LOCATION: 8
<223> OTHER INFORMATION: Xaa is D or A

<400> SEQUENCE: 20

Ala Ile Tyr Pro Gly Asn Gly Xaa Thr Ser Tyr Asn Gln Lys Phe
1               5                   10                  15

Lys Gly

<210> SEQ ID NO 21
<211> LENGTH: 13
<212> TYPE: PRT
<213> ORGANISM: Artificial sequence
<220> FEATURE:
<223> OTHER INFORMATION: Synthetic construct
<220> FEATURE:
<221> NAME/KEY: Variant
```

```
<222> LOCATION: 6
<223> OTHER INFORMATION: Xaa is N, A, Y, W or D
<220> FEATURE:
<221> NAME/KEY: Variant
<222> LOCATION: 7
<223> OTHER INFORMATION: Xaa is S or R

<400> SEQUENCE: 21

Val Val Tyr Tyr Ser Xaa Xaa Tyr Trp Tyr Phe Asp Val
1               5                   10

<210> SEQ ID NO 22
<211> LENGTH: 451
<212> TYPE: PRT
<213> ORGANISM: Artificial sequence
<220> FEATURE:
<223> OTHER INFORMATION: Synthetic construct

<400> SEQUENCE: 22

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Asp Thr Ser Tyr
        50                  55                  60

Asn Gln Lys Phe Lys Gly Arg Phe Thr Ile Ser Val Asp Lys Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Asn Ser
                95                  100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
        125                 130                 135

Ser Ser Lys Ser Thr Ser Gly Gly Thr Ala Ala Leu Gly Cys Leu
        140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp
                275                 280                 285
```

Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Lys Ala Leu Pro Ala Pro Ile Glu Lys Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Ser Asn
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly

<210> SEQ ID NO 23
<211> LENGTH: 107
<212> TYPE: PRT
<213> ORGANISM: Artificial sequence
<220> FEATURE:
<223> OTHER INFORMATION: Synthetic construct

<400> SEQUENCE: 23

Asp Ile Gln Met Thr Gln Ser Pro Ser Ser Leu Ser Ala Ser Val
1               5                   10                  15

Gly Asp Arg Val Thr Ile Thr Cys Arg Ala Ser Ser Val Ser
            20                  25                  30

Tyr Leu His Trp Tyr Gln Gln Lys Pro Gly Lys Ala Pro Lys Pro
            35                  40                  45

Leu Ile Tyr Ala Pro Ser Asn Leu Ala Ser Gly Val Pro Ser Arg
            50                  55                  60

Phe Ser Gly Ser Gly Ser Gly Thr Asp Phe Thr Leu Thr Ile Ser
            65                  70                  75

Ser Leu Gln Pro Glu Asp Phe Ala Thr Tyr Tyr Cys Gln Gln Trp
            80                  85                  90

Ala Phe Asn Pro Pro Thr Phe Gly Gln Gly Thr Lys Val Glu Ile
            95                  100                 105

Lys Arg

<210> SEQ ID NO 24
<211> LENGTH: 122
<212> TYPE: PRT
<213> ORGANISM: Artificial sequence
<220> FEATURE:
<223> OTHER INFORMATION: Synthetic construct

<400> SEQUENCE: 24

Glu Val Gln Leu Val Glu Ser Gly Gly Gly Leu Val Gln Pro Gly

```
Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Ala Thr Ser Tyr
            50                  55                  60

Asn Gln Lys Phe Lys Gly Arg Phe Thr Ile Ser Val Asp Lys Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Tyr Arg
            95                  100                 105

Tyr Trp Tyr Phe Asp Val Trp Gly Gln Gly Thr Leu Val Thr Val
            110                 115                 120

Ser Ser

<210> SEQ ID NO 25
<211> LENGTH: 451
<212> TYPE: PRT
<213> ORGANISM: Artificial sequence
<220> FEATURE:
<223> OTHER INFORMATION: Synthetic construct

<400> SEQUENCE: 25

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
            20                  25                  30

Ser Tyr Asn Met His Trp Val Arg Gln Ala Pro Gly Lys Gly Leu
            35                  40                  45

Glu Trp Val Gly Ala Ile Tyr Pro Gly Asn Gly Ala Thr Ser Tyr
            50                  55                  60

Asn Gln Lys Phe Lys Gly Arg Phe Thr Ile Ser Val Asp Lys Ser
            65                  70                  75

Lys Asn Thr Leu Tyr Leu Gln Met Asn Ser Leu Arg Ala Glu Asp
            80                  85                  90

Thr Ala Val Tyr Tyr Cys Ala Arg Val Val Tyr Tyr Ser Tyr Arg
            95                  100                 105

Tyr Trp Tyr Phe Asp Val Trp Gly Gln Gly Thr Leu Val Thr Val
            110                 115                 120

Ser Ser Ala Ser Thr Lys Gly Pro Ser Val Phe Pro Leu Ala Pro
            125                 130                 135

Ser Ser Lys Ser Thr Ser Gly Gly Thr Ala Ala Leu Gly Cys Leu
            140                 145                 150

Val Lys Asp Tyr Phe Pro Glu Pro Val Thr Val Ser Trp Asn Ser
            155                 160                 165

Gly Ala Leu Thr Ser Gly Val His Thr Phe Pro Ala Val Leu Gln
            170                 175                 180

Ser Ser Gly Leu Tyr Ser Leu Ser Ser Val Val Thr Val Pro Ser
            185                 190                 195

Ser Ser Leu Gly Thr Gln Thr Tyr Ile Cys Asn Val Asn His Lys
            200                 205                 210

Pro Ser Asn Thr Lys Val Asp Lys Lys Val Glu Pro Lys Ser Cys
            215                 220                 225
```

```
Asp Lys Thr His Thr Cys Pro Pro Cys Pro Ala Pro Glu Leu Leu
            230                 235                 240

Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln
            290                 295                 300

Tyr Asn Ala Thr Tyr Arg Val Val Ser Val Leu Thr Val Leu His
            305                 310                 315

Gln Asp Trp Leu Asn Gly Lys Glu Tyr Lys Cys Lys Val Ser Asn
            320                 325                 330

Ala Ala Leu Pro Ala Pro Ile Ala Ala Thr Ile Ser Lys Ala Lys
            335                 340                 345

Gly Gln Pro Arg Glu Pro Gln Val Tyr Thr Leu Pro Pro Ser Arg
            350                 355                 360

Glu Glu Met Thr Lys Asn Gln Val Ser Leu Thr Cys Leu Val Lys
            365                 370                 375

Gly Phe Tyr Pro Ser Asp Ile Ala Val Glu Trp Glu Ser Asn Gly
            380                 385                 390

Gln Pro Glu Asn Asn Tyr Lys Thr Thr Pro Pro Val Leu Asp Ser
            395                 400                 405

Asp Gly Ser Phe Phe Leu Tyr Ser Lys Leu Thr Val Asp Lys Ser
            410                 415                 420

Arg Trp Gln Gln Gly Asn Val Phe Ser Cys Ser Val Met His Glu
            425                 430                 435

Ala Leu His Asn His Tyr Thr Gln Lys Ser Leu Ser Leu Ser Pro
            440                 445                 450

Gly
```

METHODS FOR TREATING PROGRESSIVE MULTIPLE SCLEROSIS

CROSS-REFERENCE TO RELATED APPLICATIONS

This application is a Continuation of U.S. patent application Ser. No. 14/702,583, filed on May 1, 2015, which is a Continuation of U.S. patent application Ser. No. 14/049,130, filed Oct. 8, 2013, which is a Continuation of U.S. patent application Ser. No. 13/414,698, filed Mar. 7, 2012, which is a Divisional of U.S. patent application Ser. No. 12/561,131, filed Sep. 16, 2009, which claims priority benefit to U.S. Provisional Application Ser. No. 61/097,464, filed on Sep. 16, 2008, the disclosures of which are herein incorporated by reference in their entirety.

FIELD OF THE INVENTION

The present invention concerns methods for treating progressive multiple sclerosis (MS) in a patient, and an article of manufacture with instructions for such use.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392006103SeqList.txt, date recorded: Jun. 30, 2016, size: 33 KB).

BACKGROUND OF THE INVENTION

Multiple Sclerosis

Multiple Sclerosis (MS) is an inflammatory and demyelinating degenerative disease of the human central nervous system (CNS). It is a worldwide disease that affects approximately 300,000 persons in the United States; it is a disease of young adults, with 70%-80% having onset between 20 and 40 years old (Anderson et al. *Ann Neurology* 31(3): 333-6 (1992); Noonan et al. *Neurology* 58:136-8 (2002)). MS is a heterogeneous disorder based on clinical course, magnetic resonance imaging (MRI) scan assessment, and pathology analysis of biopsy and autopsy material (Lucchinetti et al. *Ann Neurol* 47:707-17 (2000)). The disease manifests itself in a large number of possible combinations of deficits, including spinal cord, brainstem, cranial nerve, cerebellar, cerebral, and cognitive syndromes. Progressive disability is the fate of most patients with MS, especially when a 25-year perspective is included. Half of MS patients require a cane to walk within 15 years of disease onset. MS is a major cause of neurologic disability in young and middle-aged adults and, until the past decade, has had no known beneficial treatments. MS is difficult to diagnose because of the non-specific clinical findings, which led to the development of highly structured diagnostic criteria that include several technological advances, consisting of MRI scans, evoked potentials, and cerebrospinal fluid (CSF) studies. All diagnostic criteria rely upon the general principles of scattered lesions in the central white matter occurring at different times and not explained by other etiologies such as infection, vascular disorder, or autoimmune disorder (McDonald et al. *Ann Neurol* 50:121-7 (2001)). MS has four patterns of disease: relapsing-remitting MS (RRMS; 80%-85% of cases at onset), primary progressive MS (PPMS; 10%-15% at onset), progressive relapsing MS (PRMS; 5% at onset); and secondary progressive MS (SPMS) (Kremenchutzky et al. *Brain* 122 (Pt 10):1941-50 (1999); Confavreux et al. *N Engl J Med* 343(20): 1430-8 (2000)). An estimated 50% of patients with RRMS will develop SPMS in 10 years, and up to 90% of RRMS patients will eventually develop SPMS (Weinshenker et al. *Brain* 112(Pt 1): 133-46 (1989)).

Currently, six drugs in four classes are approved in the United States for the treatment of RRMS, whereas no drugs have been approved for PPMS. The RRMS treatments include the following: interferon class, IFN-beta-1a (REBIF® and AVONEX®) and IFN-beta-1b (BETASERON®): glatiramer acetate (COPAXONE®), a polypeptide; natalizumab (TYSABRI®); and mitoxantrone (NOVANTRONE®), a cytotoxic agent. Other drugs have been used with varying degrees of success, including corticosteroids, methotrexate, cyclophosphamide, azathioprine, and intravenous (IV) immunoglobulin. The benefits of currently approved treatments are relatively modest (~30%) for relapse rate and prevention of disability in RRMS as suggested by two meta-analyses (Filippini et al. *Lancet* 361: 545-52 (2003)).

Other clinical studies evaluated other immunomodulatory agents in MS, including tumor necrosis factor-α inhibitors and altered peptide ligands, which aggravated rather than improved MS (Lenercept Multiple Sclerosis Study Group and the University of British Columbia MS/MRI *Neurology* 53:457-65 (1999); Bielekova et al. *Nat Med* 2000; 6:1167-75 (2000), erratum appears in *Nat Med* 6:1412 (2000)).

The predominant view of MS pathophysiology has held that inflammation is principally mediated by $CD4^+$ Th1 T cells. Therapeutic approaches based on this theory such as IFN-beta and glatiramer acetate decrease, but do not fully prevent, occurrence of exacerbations or accumulation of disability.

The existence of a humoral component in human MS has been implicitly recognized for decades, as evidenced by inclusion of CSF oligoclonal bands and increased intrathecal IgG synthesis in diagnostic criteria for MS (Siden A. *J Neurol* 221:39-51 (1979); McDonald et al. *Ann Neurol* 50:121-7 (2001); Andersson et al. *Eur J Neurol* 9:243-51 (2002); O'Connor, P. *Neurology* 59:S1-33 (2002). The presence of oligoclonal bands, increased free light chains, and increased intrathecal IgM synthesis correlates with MS disease activity and may be a predictor of more severe outcomes (Rudick et al. *Mult Scler* 1:150-5 (1995); Zeman et al. *Acta Cytol* 45:51-9 (2001); Izquierdo et al. *Acta Neurol Scand* 105:158-63 (2002); Wolinsky J. *J Neurol Sci* 206: 145-52 (2003); Villar et al. *Ann Neurol* 53:222-6 (2003)).

Anti-myelin antibodies (myelin basic protein (MBP) and myelin oligodendrocyte glycoprotein (MOG)) have been detected in the serum of patients with progressive and relapsing forms of MS (Reindl et al. *Brain* 122:2047-56 (1999); Egg et al. *Mult Scler* 7(5):285-9 (2001)). Anti-myelin antibodies have also been detected in the CSF of MS patients (Reindl et al. *Brain* 122:2047-56 (1999); Egg et al. *Mult Scler* 7(5):285-9 (2001); Andersson et al. *Eur J Neurol* 9:243-51 (2002)). Additional types of antibodies such as anti-ganglioside antibodies or anti-neurofilament antibodies have been observed in patients with MS (Mata et al. *Mult Scler* 5:379-88 (1999); Sadatipour et al. *Ann Neural* 44:980-3 (1998)). A report indicated that the presence of serum anti-MOG and anti-MBP antibodies was a strong predictor of progression from a clinically isolated demyelinating event to definite RRMS (Berger et al. *N Engl J Med* 349:139-45 (2003)). The adjusted hazard ratio for experiencing an exacerbation was 76.5 for patients who were seropositive for both antibodies and 31.6 for patients who were seropositive only for anti-MOG.

An international pathology consortium found that antibodies bound to myelin are present in the majority of patients with MS, with plasma cells and B cells also found in MS lesions, providing additional evidence for a humoral role in MS (Prineas and Wright, *Lab Invest* 38:409-21 (1978); Esiri M. *Neuropathol Appl Neurobiol* 6:9-21 (1980); Genain et al. *Nat Med* 5:170-5 (1999); Lucchinetti et al. *Ann Neurol* 47:707-17 (2000); Wingerchuk et al. *Lab Invest* 81:263-81 (2001)). B cells are detectable in the CSF of patients with MS, and the presence of a relatively high proportion of B cells may be predictive of more severe disability progression (Cepok et al. *Brain* 124(Pt 11):2169-76 (2001)).

In patients with RRMS or opsoclonus-myoclonus syndrome, Rituximab reportedly depleted peripheral B-cells in all patients and decreased the number of CSF B cells in some patients (Pranzatelli et al. *Neurology* 60(Suppl1) PO5.128: A395 (2003); Cross et al. "Preliminary Results from a Phase II Trial of Rituximab in MS" (abstract) *Eighth Annual Meeting of the Americas Committees for Research and Treatment in Multiple Sclerosis* ATRIMS 20-1 (October, 2003); Cross et al. *J. Neuroimmunol.* 180:63-70 (2006)). See also Cree et al. "Tolerability and Effects of Rituximab "Anti-CD20 Antibody" in Neuromyelitis Optica and Rapidly Worsening Multiple Sclerosis" *Meeting of the Am. Acad. Neurol.* (April, 2004); Cree et al. *Neurology* 64:1270-2 (2005).

CD20 Antibodies and Therapy Therewith

Lymphocytes are one of many types of white blood cells produced in the bone marrow during the process of hematopoiesis. There are two major populations of lymphocytes: B lymphocytes (B cells) and T lymphocytes (T cells). The lymphocytes of particular interest herein are B cells.

B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called "plasma cells". Memory B cells have a longer life span and continue to express membrane-bound antibody with the same specificity as the original parent cell. Plasma cells do not produce membrane-bound antibody but instead produce the antibody in a form that can be secreted. Secreted antibodies are the major effector molecule of humoral immunity.

The CD20 antigen (also called human B-lymphocyte-restricted differentiation antigen, Bp35) is a hydrophobic transmembrane protein with a molecular weight of approximately 35 kD located on pre-B and mature B lymphocytes (Valentine et al. *J. Biol. Chem.* 264(19):11282-11287 (1989); and Einfeld et al. *EMBO J.* 7(3):711-717 (1988)). The antigen is also expressed on greater than 90% of B-cell non-Hodgkin's lymphomas (NHL) (Anderson et al. *Blood* 63(6): 1424-1433 (1984)), but is not found on hematopoietic stem cells, pro-B cells, normal plasma cells or other normal tissues (Tedder et al. *J. Immunol.* 135(2):973-979 (1985)). CD20 regulates an early step(s) in the activation process for cell cycle initiation and differentiation (Tedder et al., supra) and possibly functions as a calcium ion channel (Tedder et al. *J. Cell. Biochem.* 14D:195 (1990)).

Given the expression of CD20 in B-cell lymphomas, this antigen can serve as a candidate for "targeting" of such lymphomas. In essence, such targeting can be generalized as follows: antibodies specific to the CD20 surface antigen of B cells are administered to a patient. These anti-CD20 antibodies specifically bind to the CD20 antigen of (ostensibly) both normal and malignant B cells; the antibody bound to the CD20 surface antigen may lead to the destruction and depletion of neoplastic B cells. Additionally, chemical agents or radioactive labels having the potential to destroy the tumor can be conjugated to the anti-CD20 antibody such that the agent is specifically "delivered" to the neoplastic B cells. Irrespective of the approach, a primary goal is to destroy the tumor; the specific approach can be determined by the particular anti-CD20 antibody that is utilized and, thus, the available approaches to targeting the CD20 antigen can vary considerably.

The Rituximab (RITUXAN®) antibody is a genetically engineered chimeric murine/human monoclonal antibody directed against the CD20 antigen. Rituximab is the antibody called "C2B8" in U.S. Pat. No. 5,736,137 issued Apr. 7, 1998 (Anderson et al.). RITUXAN® is indicated for the treatment of patients with relapsed or refractory low-grade or follicular, CD20-positive, B-cell non-Hodgkin's lymphoma. In vitro mechanism of action studies have demonstrated that RITUXAN® binds human complement and lyses lymphoid B-cell lines through complement-dependent cytotoxicity (CDC) (Reff et al. *Blood* 83(2):435-445 (1994)). Additionally, it has significant activity in assays for antibody-dependent cellular cytotoxicity (ADCC). More recently, RITUXAN® has been shown to have anti-proliferative effects in tritiated thymidine incorporation assays and to induce apoptosis directly, while other anti-CD19 and CD20 antibodies do not (Maloney et al. *Blood* 88(10):637a (1996)). Synergy between RITUXAN® and chemotherapies and toxins has also been observed experimentally. In particular, RITUXAN® sensitizes drug-resistant human B-cell lymphoma cell lines to the cytotoxic effects of doxorubicin, CDDP, VP-16, diphtheria toxin and ricin (Demidem et al. *Cancer Chemotherapy & Radiopharmaceuticals* 12(3):177-186 (1997)). In vivo preclinical studies have shown that RITUXAN® depletes B cells from the peripheral blood, lymph nodes, and bone marrow of cynomolgus monkeys, presumably through complement and cell-mediated processes (Reff et al. *Blood* 83(2):435-445 (1994)).

Rituximab was approved in the United States in November 1997 for the treatment of patients with relapsed or refractory low-grade or follicular CD20$^+$ B-cell non-Hodgkin's lymphoma (NHL) at a dose of 375 mg/m$^2$ weekly for four doses. In April 2001, the Food and Drug Administration (FDA) approved additional claims for the treatment of low-grade NHL: retreatment (weekly for four doses) and an additional dosing regimen (weekly for eight doses). There have been more than 300,000 patient exposures to Rituximab either as monotherapy or in combination with immunosuppressant or chemotherapeutic drugs. Patients have also been treated with Rituximab as maintenance therapy for up to 2 years (Hainsworth et al. *J Clin Oncol* 21:1746-51 (2003); Hainsworth et al. *J Clin Oncol* 20:4261-7 (2002)).

Rituximab has also been studied in a variety of non-malignant autoimmune disorders, in which B cells and autoantibodies appear to play a role in disease pathophysiology (Edwards et al. *Biochem Soc Trans* 30:824-8 (2002)). Rituximab has been reported to potentially relieve signs and symptoms of rheumatoid arthritis (RA) (Leandro et al. *Ann Rheum Dis.* 61:883-8 (2002); Emery et al. *Arthritis Rheum* 48(9):S439 (2003)), lupus (Eisenberg R. *Arthritis Res Ther* 5:157-9 (2003); Leandro et al. *Arthritis Rheum* 46:2673-7 (2002)), immune thrombocytopenia (D'Arena et al. *Leuk Lymphoma* 44:561-2 (2003)), autoimmune anemia (Zaja et al. *Haematologica* 87:189-95 (2002) (erratum appears in *Haematologica* 87:336 (2002)), autoimmune neuropathy (Pestronk et al. *J Neurol Neurosurg Psychiatry* 74:485-9 (2003)), paraneoplastic opsoclonus-myoclonus syndrome (Pranzatelli et al. *Neurology* 60(Suppl1) PO5.128:A395 (2003)), and relapsing-remitting multiple sclerosis (RRMS) (Cross et al. (abstract) Eighth Annual Meeting of the Americas Committees for Research and Treatment in Multiple Sclerosis 20-1 (2003)).

A Phase II study (WA16291) has been conducted in patients with rheumatoid arthritis (RA), providing 48-week follow-up data on safety and efficacy of Rituximab (Emery et al. *Arthritis Rheum* 48(9):S439 (2003); Szczepanski et al. *Arthritis Rheum* 48(9):S121 (2003)). A total of 161 patients were evenly randomized to four treatment arms: methotrexate, Rituximab alone, Rituximab plus methotrexate, Rituximab plus cyclophosphamide (CTX). The treatment regimen of Rituximab was 1 g administered intravenously on Days 1 and 15. Infusions of Rituximab in most patients with RA were well tolerated by most patients, with 36% of patients experiencing at least one adverse event during their first infusion (compared with 30% of patients receiving placebo). Overall, the majority of adverse events were considered to be mild to moderate in severity and were well balanced across all treatment groups. There were a total of 19 serious adverse events across the four arms over the 48 weeks, which were slightly more frequent in the Rituximab/CTX group. The incidence of infections was well balanced across all groups. The mean rate of serious infection in this RA patient population was 4.6 6 per 100 patient-years, which is lower than the rate of infections requiring hospital admission in RA patients (9.57 per 100 patient-years) reported in a community-based epidemiologic study (Doran et al. *Arthritis Rheum* 46:2287-93 (2002)).

The reported safety profile of Rituximab in a small number of patients with neurologic disorders, including autoimmune neuropathy (Pestronk et al. *J Neurol Neurosurg Psychiatry* 74:485-9 (2003)), opsoclonus/myoclonus syndrome (Pranzatelli et al. *Neurology* 60(Suppl1) PO5.128: A395 (2003)), and RRMS (Cross et al. Preliminary results from a phase II trial of Rituximab in MS (abstract) Eighth Annual Meeting of the Americas Committees for Research and Treatment in Multiple Sclerosis 20-1 (2003)), was reported. In an ongoing investigator-sponsored trial (IST) of Rituximab in combination with interferon-beta (IFN-beta☐) or glatiramer acetate in subjects with RRMS (Cross et al., supra), 1 of 10 treated subjects was admitted to the hospital for overnight observation after experiencing moderate fever and rigors following the first infusion of Rituximab, while the other 9 subjects completed the four-infusion regimen without any reported adverse events.

Patents and patent publications concerning CD20 antibodies, CD20-binding molecules, and self-antigen vaccines include U.S. Pat. Nos. 5,776,456, 5,736,137, 5,843,439, 6,399,061, and 6,682,734, as well as US 2002/0197255, US 2003/0021781, US 2003/0082172, US 2003/0095963, US 2003/0147885, US 2005/0186205, and WO 1994/11026 (Anderson et al.); U.S. Pat. No. 6,455,043, US 2003/0026804, US 2003/0206903, and WO 2000/09160 (Grillo-Lopez, A.); WO 2000/27428 (Grillo-Lopez and White); US 2004/0213784 and WO 2000/27433 (Grillo-Lopez and Leonard); WO 2000/44788 (Braslawsky et al.); WO 2001/10462 (Rastetter, W.); WO 2001/10461 (Rastetter and White); WO 2001/10460 (White and Grillo-Lopez); US 2001/0018041, US 2003/0180292, US 2002/0028178, WO 2001/34194, and WO 2002/22212 (Hanna and Hariharan); US 2002/0006404 and WO 2002/04021 (Hanna and Hariharan); US 2002/0012665, US 2005/0180975, WO 2001/74388, and U.S. Pat. No. 6,896,885 (Hanna, N.); US 2002/0058029 (Hanna, N.); US 2003/0103971 (Hariharan and Hanna); US 2005/0123540 (Hanna et al.); US 2002/0009444 and WO 2001/80884 (Grillo-Lopez, A.); WO 2001/97858; US 2005/0112060, US 2002/0039557, and U.S. Pat. No. 6,846,476 (White, C.); US 2002/0128448 and WO 2002/34790 (Reff, M.); WO 2002/060955 (Braslawsky et al.); WO 2002/096948 (Braslawsky et al.); WO 2002/079255 (Reff and Davies); U.S. Pat. Nos. 6,171,586 and 6,991,790, and WO 1998/56418 (Lam et al.); US 2004/0191256 and WO 1998/58964 (Raju, S.); WO 1999/22764 (Raju, S.): WO 1999/51642, U.S. Pat. No. 6,194,551, U.S. Pat. Nos. 6,242,195, 6,528,624 and 6,538,124 (Idusogie et al.); U.S. Pat. No. 7,122,637, US 2005/0118174, US 2005/0233382, US 2006/0194291, US 2006/0194290, US 2006/0194957, and WO 2000/42072 (Presta, L.); WO 2000/67796 (Curd et al.); WO 2001/03734 (Grillo-Lopez et al.); US 2002/0004587, US 2006/0025576, and WO 2001/77342 (Miller and Presta); US 2002/0197256 and WO 2002/078766 (Grewal, I.); US 2003/0157108 and WO 2003/035835 (Presta, L.); U.S. Pat. Nos. 5,648,267, 5,733,779, 6,017,733, and 6,159,730, and WO 1994/11523 (Reff et al. on expression technology); U.S. Pat. Nos. 6,565,827, 6,090,365, 6,287,537, 6,015,542, 5,843, 398, and 5,595,721 (Kaminski et al.); U.S. Pat. Nos. 5,500, 362, 5,677,180, 5,721,108, 6,120,767, 6,652,852, and 6,893, 625 as well as WO 1988/04936 (Robinson et al.); U.S. Pat. No. 6,410,391 (Zelsacher): U.S. Pat. No. 6,224,866 and WO 2000/20864 (Barbera-Guillem, E.); WO 2001/13945 (Barbera-Guillem, E.); WO 2000/67795 (Goldenberg); U.S. Pat. No. 7,074,403 (Goldenberg and Hansen); U.S. Pat. No. 7,151,164 (Hansen et al.); US 2003/0133930; WO 2000/74718 and US 2005/0191300A1 (Goldenberg and Hansen); US 2003/0219433 and WO 2003/68821 (Hansen et al.); WO 2004/058298 (Goldenberg and Hansen); WO 2000/76542 (Golay et al.); WO 2001/72333 (Wolin and Rosenblatt); U.S. Pat. No. 6,368,596 (Ghetie et al.); U.S. Pat. No. 6,306,393 and US 2002/0041847 (Goldenberg, D.); US 2003/0026801 (Weiner and Hartmann); WO 2002/102312 (Engleman, E.); US 2003/0068664 (Albitar et al.); WO 2003/002607 (Leung, S.); WO 2003/049694, US 2002/0009427, and US 2003/0185796 (Wolin et al.); WO 2003/061694 (Sing and Siegall); US 2003/0219818 (Bohen et al.); US 2003/0219433 and WO 2003/068821 (Hansen et al.); US 2003/0219818 (Bohen et al.); US 2002/0136719 (Shenoy et al.); WO 2004/032828 and US 2005/0180972 (Wahl et al.); and WO 2002/56910 (Hayden-Ledbetter). See also U.S. Pat. No. 5,849,898 and EP 330,191 (Seed et al.); EP332,865A2 (Meyer and Weiss); U.S. Pat. No. 4,861,579 (Meyer et al.); US 2001/0056066 (Bugelski et al.); WO 1995/03770 (Bhat et al.); US 2003/0219433 A1 (Hansen et al.): WO 2004/035607 and US 2004/167319 (Teeling et al.); WO 2005/103081 (Teeling et al.); US 2006/0034835, US 2006/0024300, and WO 2004/056312 (Lowman et al.); US 2004/0093621 (Shitara et al.); WO 2004/103404 (Watkins et al.); WO 2005/000901 (Tedder et al.); US 2005/0025764 (Watkins et al.); US 2006/0251652 (Watkins et al.); WO 2005/016969 (Carr et al.); US 2005/0069545 (Carr et al.); WO 2005/014618 (Chang et al.): US 2005/0079174 (Barbera-Guillem and Nelson); US 2005/0106108 (Leung and Hansen); US 2005/0123546 (Umana et al.); US 2004/0072290 (Umana et al.); US 2003/0175884 (Umana et al.); and WO 2005/044859 (Umana et al.); WO 2005/070963 (Allan et al.): US 2005/0186216 (Ledbetter and Hayden-Ledbetter); US 2005/0202534 (Hayden-Ledbetter and Ledbetter); US 2005/136049 (Ledbetter et al.): US 2003/118592 (Ledbetter et al.); US 2003/133939 (Ledbetter and Hayden-Ledbetter);

US 2005/0202012 (Ledbetter and Hayden-Ledbetter); US 2005/0175614 (Ledbetter and Hayden-Ledbetter); US 2005/0180970 (Ledbetter and Hayden-Ledbetter); US 2005/0202028 (Hayden-Ledbetter and Ledbetter); US 2005/0202023 (Hayden-Ledbetter and Ledbetter); WO 2005/017148 (Ledbetter et al.); WO 2005/037989 (Ledbetter et al.); U.S. Pat. No. 6,183,744 (Goldenberg); U.S. Pat. No. 6,897,044 (Braslawski et al.); WO 2006/005477 (Krause et al.); US 2006/0029543 (Krause et al.); US 2006/0018900 (McCormick et al.); US 2006/0051349 (Goldenberg and Hansen); WO 2006/042240 (Iyer and Dunussi-Joannopoulos); US 2006/0121032 (Dahiyat et al.); WO 2006/064121 (Teillaud et al.); US 2006/0153838 (Watkins), CN 1718587 (Chen et al.); WO 2006/084264 (Adams et al.); US 2006/0188495 (Barron et al.); US 2004/0202658 and WO 2004/091657 (Benynes, K.); US 2005/0095243, US 2005/0163775, WO 2005/00351, and WO 2006/068867 (Chan, A.); US 2006/0135430 and WO 2005/005462 (Chan et al.); US 2005/0032130 and WO 2005/017529 (Beresini et al.); US 2005/0053602 and WO 2005/023302 (Brunetta, P.); US 2006/0179501 and WO 2004/060052 (Chan et al.): WO 2004/060053 (Chan et al.); US 2005/0186206 and WO 2005/060999 (Brunetta, P.); US 2005/0191297 and WO 2005/061542 (Brunetta, P.); US 2006/0002930 and WO 2005/115453 (Brunetta et al.); US 2006/0099662 and WO 2005/108989 (Chuntharapai et al.); CN 1420129A (Zhongxin Guojian Pharmaceutical); US 2005/0276803 and WO 2005/113003 (Chan et al.); US 2005/0271658 and WO 2005/117972 (Brunetta et al.); US 2005/0255527 and WO 2005/11428 (Yang, J.); US 2006/0024295 and WO 2005/120437 (Brunetta, P.); US 2006/0051345 and WO 2005/117978 (Frohna, P.); US 2006/0062787 and WO 2006/012508 (Hitraya, E.); US 2006/0067930 and WO 2006/31370 (Lowman et al.); WO 2006/29224 (Ashkenazi, A.); US 2006/0110387 and WO 2006/41680 (Brunetta, P.); US 2006/0134111 and WO 2006/066086 (Agarwal, S.); WO 2006/069403 (Ernst and Yansura); US 2006/0188495 and WO 2006/076651 (Dummer, W.); WO 2006/084264 (Lowman, H.); WO 2006/093923 (Quan and Sewell); WO 2006/106959 (Numazaki et al.); WO 2006/126069 (Morawala); WO 2006/130458 (Gazit-Bornstein et al.): US 2006/0275284 (Hanna, G.); US 2007/0014785 (Golay et al.); US 2007/0014720 (Gazit-Bornstein et al.); and US 2007/0020259 (Hansen et al.); US 2007/0020265 (Goldenberg and Hansen); US 2007/0014797 (Hitraya); US 2007/0224189 (Lazar et al.); WO 2007/014238 (Bruge and Bruger); and WO 2008/003319 (Parren and Baadsgaard). Certain of these include, inter alia, treatment of multiple sclerosis.

Publications concerning therapy with Rituximab include: Perotta and Abuel "Response of chronic relapsing ITP of 10 years duration to Rituximab" Abstract #3360 *Blood* 10(1) (part 1-2): p. 88B (1998); Stashi et al. "Rituximab chimeric anti-CD20 monoclonal antibody treatment for adults with chronic idopathic thrombocytopenic purpura" *Blood* 98(4): 952-957 (2001); Matthews, R. "Medical Heretics" *New Scientist* (7 April, 2001); Leandro et al. "Clinical outcome in 22 patients with rheumatoid arthritis treated with B lymphocyte depletion" *Ann Rheum Dis* 61:833-888 (2002); Leandro et al. "Lymphocyte depletion in rheumatoid arthritis: early evidence for safety, efficacy and dose response. *Arthritis and Rheumatism* 44(9): S370 (2001); Leandro et al. "An open study of B lymphocyte depletion in systemic lupus erythematosus", *Arthritis & Rheumatism* 46(1):2673-2677 (2002); Edwards and Cambridge "Sustained improvement in rheumatoid arthritis following a protocol designed to deplete B lymphocytes" *Rhematology* 40:205-211 (2001); Edwards et al. "B-lymphocyte depletion therapy in rheumatoid arthritis and other autoimmune disorders" *Biochem. Soc. Trans.* 30(4):824-828 (2002); Edwards et al. "Efficacy and safety of Rituximab, a B-cell targeted chimeric monoclonal antibody: A randomized, placebo controlled trial in patients with rheumatoid arthritis. *Arthritis and Rheumatism* 46(9): S197 (2002); Levine and Pestronk "IgM antibody-related polyneuropathies: B-cell depletion chemotherapy using Rituximab" *Neurology* 52: 1701-1704 (1999); DeVita et al. "Efficacy of selective B cell blockade in the treatment of rheumatoid arthritis" *Arthritis & Rheum* 46:2029-2033 (2002); Hidashida et al. "Treatment of DMARD-Refractory rheumatoid arthritis with Rituximab." Presented at the *Annual Scientific Meeting of the American College of Rheumatology; October* 24-29; New Orleans, La. 2002; Tuscano, J. "Successful treatment of Infliximab-refractory rheumatoid arthritis with Rituximab" Presented at the *Annual Scientific Meeting of the American College of Rheumatology*; October 24-29; New Orleans, La. 2002; Specks et al. "Response of Wegener's granulomatosis to anti-CD20 chimeric monoclonal antibody therapy" *Arthritis & Rheumatism* 44(12):2836-2840 (2001); Anolik et al., "B lympocyte Depletion in the Treatment of Systemic Lupus (SLE): Phase I/II Trial of Rituximab (RITUXAN®) in SLE" *Arthritis And Rheumatism,* 46(9), S289-S289 Abstract 717 (October, 2002), and Albert et al., "A Phase I Trial of Rituximab (Anti-CD20) for Treatment of Systemic Lupus Erythematosus" *Arthritis And Rheumatism,* 48(12): 3659-3659, Abstract LB9 (December, 2003); Martin and Chan "Pathogenic Roles of B cells in Human Autoimmunity: Insights from the Clinic" *Immunity* 20:517-527 (2004); Cree et al. "An open label study of the effects of rituximab in neuromyelitis optica." *Neurology* 64(7):1270-2 (2005); Cross et al. "Rituximab reduces B cells and T cells in cerebrospinal fluid of multiple sclerosis patients." *J Neuroimmunol,* 180(1-2):63-70 (2006); Bar-Or A. et al., "Safety, pharmacodynamics, and activity of Rituximab in patients with relapsing-remitting multiple sclerosis: a phase I, multicentre, open-label clinical trial." *Ann Neurol* 63(3):395-400 (2008); Hauser S. et al., "B-cell depletion with Rituximab in relapsing-remitting multiple sclerosis." *NEJM,* 358(7):676-88, (2008); Hawker K et al., "Efficacy and Safety of rituximab in patients with primary progressive multiple sclerosis: results of a randomized, double-blind, placebo-controlled, multicenter trial." *Multiple Sclerosis* 14(1):S299 (2008), Abstract; Hawker K et al., "Efficacy and Safety of rituximab in patients with primary progressive multiple sclerosis: results of a randomized, double-blind, placebo-controlled, multicenter trial." *Neurology* 72(S3): A254 (2009), Abstract.

BRIEF SUMMARY OF THE INVENTION

The present invention provides methods of treating progressive multiple sclerosis in a patient comprising administering to the patient an effective amount of an anti-CD20 antibody, wherein treatment is based upon the patient having one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments, the effective amount of the anti-CD20 antibody is administered to the patient to provide an initial anti-CD20 antibody exposure of between about 0.3 to about 4.0 grams followed by a second anti-CD20 antibody exposure of between about 0.3 to about 4.0 grams. In some embodiments, the initial anti-CD20 antibody exposure and/or the second anti-CD20 antibody exposure is between about 0.3 to about 1.5 grams. In some embodiments, the second exposure not being provided until from about 16 to 60 weeks from the initial exposure. In some embodiments, each of the anti-CD20 antibody exposures is provided to the patient as one or two doses of anti-CD20 antibody.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention provides methods of treating progressive multiple sclerosis in a patient provided that the patient has been found to have one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, the treatment comprising administering to the patient an effective amount of an anti-CD20 antibody.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments, the effective amount of the anti-CD20 antibody is administered to the patient to provide an initial anti-CD20 antibody exposure of between about 0.3 to about 4.0 grams followed by a second anti-CD20 antibody exposure of between about 0.3 to about 4.0 grams. In some embodiments, the initial anti-CD20 antibody exposure and/or the second anti-CD20 antibody exposure is between about 0.3 to about 1.5 grams. In some embodiments, the second exposure not being provided until from about 16 to 60 weeks from the initial exposure. In some embodiments, each of the anti-CD20 antibody exposures is provided to the patient as one or two doses of anti-CD20 antibody.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention provides methods of treating progressive multiple sclerosis, comprising: (a) selecting a patient having progressive multiple sclerosis, wherein said patient has one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points, and (b) administering to the patient thus selected an effective amount of an anti-CD20 antibody.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments, the effective amount of the anti-CD20 antibody is administered to the patient to provide an initial anti-CD20 antibody exposure of between about 0.3 to about 4.0 grams followed by a second anti-CD20 antibody exposure of between about 0.3 to about 4.0 grams. In some embodiments, the initial anti-CD20 antibody exposure and/or the second anti-CD20 antibody exposure is between about 0.3 to about 1.5 grams. In some embodiments, the second exposure not being provided until from about 16 to 60 weeks from the initial exposure. In some embodiments, each of the anti-CD20 antibody exposures is provided to the patient as one or two doses of anti-CD20 antibody.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention also provides methods of assessing whether a patient with progressive multiple sclerosis will respond to treatment with an anti-CD20 antibody comprising assessing one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, wherein one or more of the characteristics in the patient indicates the patient will be responsive to the treatment.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the method further comprises advising a patient.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention also provides methods of identifying a patient with progressive multiple sclerosis likely to respond to anti-CD20 antibody treatment comprising: (a) assessing one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; and (b) identifying the patient having one or more characteristics selected from the group consisting of (i) an age less than about 55 years, (i) one or more gadolinium staining lesions, (iii) at least about a one point increase in Expanded Disability Status Scale (EDSS) over two years prior to starting the anti-CD20 treatment, and (iv) a Multiple Sclerosis Severity Score (MSSS) greater than about 5 points.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the method further comprises advising a patient.

In some embodiments, the anti-CD20 antibody comprises: a) a heavy chain variable region comprising SEQ ID NO:10, SEQ ID NO:11, and SEQ ID NO:12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention further provides methods for marketing an anti-CD20 antibody or a pharmaceutically acceptable composition thereof for use in a progressive multiple sclerosis patient subpopulation, the methods comprising informing a target audience about the use of the anti-CD20 antibody for treating the patient subpopulation characterized by the patients of such subpopulation having one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient subpopulation is not diagnosed with relapsing remitting multiple sclerosis when starting treatment.

In some embodiments, the patient subpopulation further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient subpopulation had an EDSS of greater than about 5.0 for less than about 15 years. In some embodiments, the patient subpopulation had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient subpopulation further had two or more relapses within two years prior to starting treatment. In some embodiments, the EDSS when starting treatment is between about 3.0 and about 6.5.

In some embodiments, the age of the patient subpopulation is less than about 51.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention provides articles of manufacture comprising, packaged together, a pharmaceutical composition comprising an anti-CD20 antibody and a pharmaceutically acceptable carrier and a label denoting (i.e., indicating) that the anti-CD20 antibody or pharmaceutical composition is indicated for treating patients with multiple sclerosis having one or more characteristics selected from the group consisting of (a) an age less than about 55 years. (b) one or more gadolinium staining lesions, (c) at least about a one point increase in Expanded Disability Status Scale (EDSS) over two years prior to starting the treatment, and (d) a Multiple Sclerosis Severity Score (MSSS) greater than about 5 points.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the patient has had an EDSS of greater than about 5.0 for less than about 15 years. In some embodiments, the patient has had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the patient further had two or more relapses within two years prior to starting treatment. In some embodiments, the EDSS when starting treatment is between about 3.0 and about 6.5.

In some embodiments, the age of the patient is less than about 51.

In some embodiments, the pharmaceutical composition comprising the anti-CD20 antibody and the pharmaceutically acceptable carrier is in a container. In some embodiments, the container comprises between about 0.3 to about 4.0 grams of the anti-CD20 antibody. In some embodiments, the container comprises between about 0.3 to about 1.5 grams of the anti-CD20 antibody.

In some embodiments, the label provides instructions, wherein the instructions indicate that an effective amount of the anti-CD20 antibody is administered to the patient to provide an initial anti-CD20 antibody exposure of between about 0.3 to about 4.0 grams followed by a second anti-CD20 antibody exposure of between about 0.3 to about 4.0 grams. In some embodiments, the initial anti-CD20 antibody exposure and/or the second anti-CD20 antibody exposure is between about 0.3 to about 1.5 grams. In some embodiments, the second exposure not being provided until from about 16 to 60 weeks from the initial exposure. In some embodiments, each of the anti-CD20 antibody exposures is provided to the patient as one or two doses of anti-CD20 antibody.

In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The present invention also provides methods for predicting whether a subject with progressive multiple sclerosis will respond to a treatment with a drug used to treat multiple sclerosis, the methods comprising assessing one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, whereby the age, the gadolinium staining lesions, the increase in EDDS over two years prior to starting the treatment, the MSSS, or a combination thereof indicates that the subject will respond to the treatment.

In some embodiments, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the subject is not diagnosed with relapsing remitting multiple sclerosis when starting treatment.

In some embodiments, the subject further has had evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments, the subject has had an EDSS of greater than about 5.0 for less than about 15 years. In some embodiments, the subject had an EDSS less than or equal to about 5.0 for less than about 10 years. In some embodiments, the increase in EDSS over two years prior to starting treatment is not attributable to relapse. In some embodiments, the increase in EDSS is at least about a 1.5 point increase in EDSS over two years prior to starting treatment. In some embodiments, the at least about a 1.5 point increase in EDSS over two years prior to starting treatment is not attributable to relapse. In some embodiments, the subject further had two or more relapses within two years prior to starting treatment. In some embodiments, the EDSS when starting treatment is between about 3.0 and about 6.5.

In some embodiments, the age of the subject is less than about 51.

In some embodiments of any of the methods or articles of manufacture described herein, the patients have one or more characteristics selected from the group consisting of (a) an age less than about 55 years, (b) one or more gadolinium staining lesions, and (c) at least about a one point increase in Expanded Disability Status Scale (EDSS) over two years prior to starting treatment.

The invention further provides methods of treating multiple sclerosis in a patient comprising administering an effective amount of ocrelizumab to the patient to provide an initial ocrelizumab exposure of between about 0.3 to about 0.6 grams followed by a second ocrelizumab exposure of between about 0.3 to about 0.6 grams, the second exposure not being provided until from about 16 to 60 weeks from the initial exposure, and each of the ocrelizumab exposures is provided to the patient as one or two doses of ocrelizumab.

In some embodiments, the initial ocrelizumab exposure is about 0.6 grams. In some embodiments, the second ocrelizumab exposure is about 0.6 grams. In some embodiments, the second exposure is administered from about 24 weeks from the initial exposure. In some embodiments, one or more of the ocrelizumab exposures are provided to the patient as one dose of ocrelizumab. In some embodiments, one or more of the ocrelizumab exposures are provided to the patient as two doses of ocrelizumab. In some embodiments, the initial ocrelizumab exposure comprises a first dose and a second dose of ocrelizumab, wherein the first dose and second dose of ocrelizumab is about 0.3 grams. In some embodiments, the second ocrelizumab exposure comprises a single dose of ocrelizumab, wherein the single dose of ocrelizumab is 0.6 grams. In some embodiments, the methods further comprising providing a third ocrelizumab exposure. In some embodiments, the methods further comprising providing a fourth ocrelizumab exposure. In some embodiments, the methods further comprising providing a fifth ocrelizumab exposure. In some embodiments of any of the methods, the methods further comprising providing between about one to about three subsequent ocrelizumab exposures.

The invention also provides articles of manufacture comprising: (a) a container comprising ocrelizumab; and (b) a package insert with instructions for treating multiple sclerosis in a patient, wherein the instructions denote that an amount of ocrelizumab is administered to the patient that is effective to provide an initial ocrelizumab exposure of between about 0.3 to about 0.6 grams followed by a second ocrelizumab exposure of between about 0.3 to about 0.6 grams, the second exposure not being administered until from about 16 to 60 weeks from the initial exposure, and each of the ocrelizumab exposures is provided to the patient as one or two doses of ocrelizumab.

In some embodiments, the initial ocrelizumab exposure is about 0.6 grams. In some embodiments, the second ocrelizumab exposure is about 0.6 grams. In some embodiments, the second exposure is administered from about 24 weeks from the initial exposure. In some embodiments, one or more of the ocrelizumab exposures are provided to the patient as one dose of ocrelizumab. In some embodiments, one or more of the ocrelizumab exposures are provided to the patient as two doses of ocrelizumab. In some embodiments, the initial ocrelizumab exposure comprises a first dose and a second dose of ocrelizumab, wherein the first dose and second dose of ocrelizumab is about 0.3 grains. In some embodiments, the instructions further comprising providing a third ocrelizumab exposure. In some embodiments, the instructions further comprising providing a fourth ocrelizumab exposure. In some embodiments, the instructions further comprising providing a fifth ocrelizumab exposure. In some embodiments of any of the methods, the instructions further comprising providing between about one to about three subsequent ocrelizumab exposures.

BRIEF DESCRIPTION OF THE DRAWINGS

FIG. 1A is a sequence alignment comparing the amino acid sequences of the light chain variable domain ($V_L$) of each of murine 2H7 (SEQ ID NO:1), humanized 2H7.v16 variant (SEQ ID NO:2), and the human kappa light chain subgroup I (SEQ ID NO:3). The CDRs of $V_L$ of 2H7 and hu2H7.v16 are as follows: CDR1 (SEQ ID NO:4), CDR2 (SEQ ID NO:5), and CDR3 (SEQ ID NO:6).

FIG. 1B is a sequence alignment comparing the amino acid sequences of the heavy chain variable domain ($V_H$) of each of murine 2H7 (SEQ ID NO:7), humanized 2H7.v16 variant (SEQ ID NO:8), and the human consensus sequence of the heavy chain subgroup III (SEQ ID NO:9). The CDRs of $V_H$ of 21H7 and hu2H17.v16 are as follows: CDR1 (SEQ ID NO: 10), CDR2 (SEQ ID NO:11), and CDR3 (SEQ ID NO:12).

In FIG. 1A and FIG. 1B, the CDR1, CDR2 and CDR3 in each chain are enclosed within brackets, flanked by the framework regions, FR1-FR4, as indicated, 2H7 refers to the murine 2H7 antibody. The asterisks in between two rows of sequences indicate the positions that are different between the two sequences. Residue numbering is according to Kabat et al. *Sequences of Immunological Interest,* 5th Ed. Public Health Service, National Institutes of Health, Bethesda, Md. (1991), with insertions shown as a, b, c, d, and e.

FIG. 2 shows the amino acid sequence of the mature 2H7.v16 light chain (SEQ ID NO:13)

FIG. 3 shows the amino acid sequence of the mature 2H7.v16 heavy chain (SEQ ID NO:14).

FIG. 4 shows the amino acid sequence of the mature 2H7.v31 heavy chain (SEQ ID NO:15). The L chain of 2H7.v31 is the same as for 2H7.v16.

FIG. 5 shows an alignment of the mature 2H7.v16 and 2H7.v511 light chains (SEQ ID NOS. 13 and 16, respectively), with Kabat variable domain residue numbering and Eu constant domain residue numbering.

FIG. 6 shows an alignment of the mature 2H7.v16 and 2H7.v511 heavy chains (SEQ ID NOS. 14 and 17, respectively), with Kabat variable domain residue numbering and Eu constant domain residue numbering.

FIG. 7 shows an overview of the study design for treating relapsing-remitting multiple sclerosis using ocrelizumab.

FIG. 8 shows Kaplan Meier plots of the time to confirmed disease progression for subjects in the placebo and rituximab groups.

FIG. 11A shows multivariate analysis of age <51 and Gd lesions at baseline=0. FIG. 11B shows multivariate analysis of age ≥51 and Gd lesions at baseline=0. FIG. 11C shows multivariate analysis of age <51 and Gd lesions at baseline ≥1. FIG. 11D shows multivariate analysis of age ≥51 and Gd lesions at baseline ≥1.

FIG. 12A shows multivariate analysis of age ≤55 and MSSS <5. FIG. 12B shows multivariate analysis of age >55 and MSSS <5. FIG. 12C shows multivariate analysis of age ≤55 and MSSS ≥5. FIG. 12D shows multivariate analysis of age >55 and MSSS ≥5.

DETAILED DESCRIPTION OF THE INVENTION

I. Definitions

Figure 9:
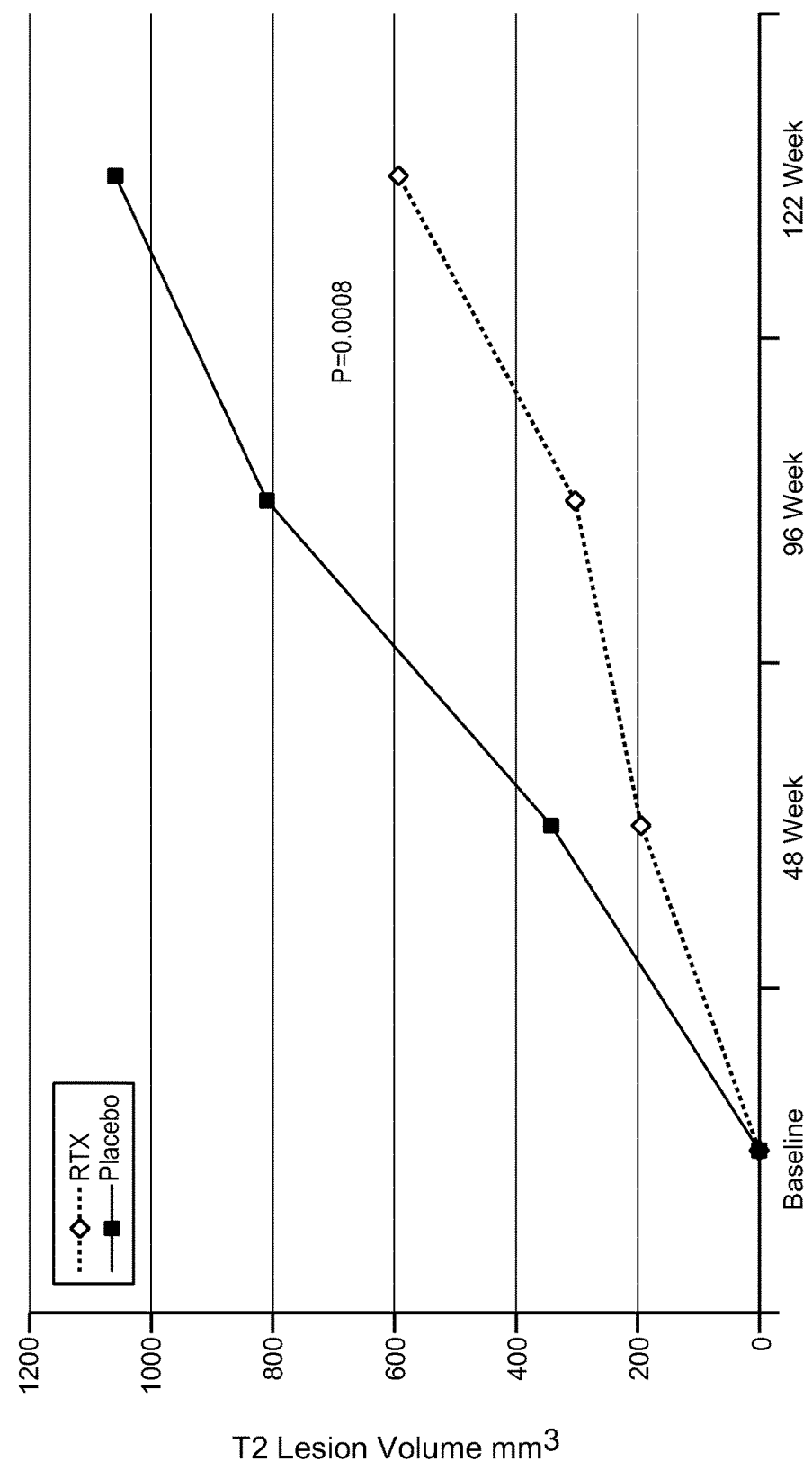
FIG. 9 shows the median change in T2 lesion volume from baseline to week 96. The Y-axis shows the T2 Lesion Volume $mm^3$.

A "B-cell" is a lymphocyte that matures within the bone marrow, and includes a naive B cell, memory B cell, or effector B cell (plasma cells). The B-cell herein may be a normal or non-malignant B cell.

A "B-cell surface marker" or "B-cell surface antigen" herein is an antigen expressed on the surface of a B cell that can be targeted with an antibody that binds thereto. Exemplary B-cell surface markers include the CD10. CD19. CD20, CD21, CD22, CD23, CD24, CD37, CD40, CD53, CD72, CD73, CD74, CDw75, CDw76, CD77, CDw78, CD79a, CD79b, CD80, CD81, CD82. CD83, CDw84, CD85 and CD86 leukocyte surface markers (for descriptions, see The Leukocyte Antigen Facts Book, 2nd Edition, 1997, ed. Barclay et al. Academic Press, Harcourt Brace & Co., New York). Other B-cell surface markers include RP105, FcRH2, B-cell CR2, CCR6, P2X5, HLA-DOB, CXCR5, FCER2, BR3, Btig, NAG14, SLGC16270, FcRH1, IRTA2, ATWD578, FcRH3, IRTA1, FcRH6, BCMA, and 239287. The B-cell surface marker of particular interest herein is preferentially expressed on B cells compared to other non-B-cell tissues of a mammal and may be expressed on both precursor B cells and mature B cells. The preferred B-cell surface marker herein is CD20.

The "CD20" antigen, or "CD20." is an about 35-kDa, non-glycosylated phosphoprotein found on the surface of greater than 90% of B cells from peripheral blood or lymphoid organs. CD20 is present on both normal B cells as well as malignant B cells, but is not expressed on stem cells. Other names for CD20 in the literature include "B-lymphocyte-restricted antigen" and "Bp35". The CD20 antigen is described in Clark et al. *Proc. Natl. Acad. Sci.* (USA) 82:1766 (1985), for example.

An "antibody antagonist" herein is a antibody that, upon binding to a B cell surface marker on B cells, destroys or depletes B cells in a mammal and/or interferes with one or more B-cell functions, e.g. by reducing or preventing a humoral response elicited by the B cell. The antibody antagonist preferably is able to deplete B cells (i.e. reduce circulating B-cell levels) in a mammal treated therewith. Such depletion may be achieved via various mechanisms such antibody-dependent cell-mediated cytotoxicity (ADCC) and/or complement dependent cytotoxicity (CDC), inhibition of B-cell proliferation and/or induction of B-cell death (e.g. via apoptosis).

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refer to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Growth inhibitory" antibodies are those that prevent or reduce proliferation of a cell expressing an antigen to which the antibody binds. For example, the antibody may prevent or reduce proliferation of B cells in vitro and/or in vivo.

Antibodies that "induce apoptosis" are those that induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

For the purposes herein, an "intact antibody" is one comprising heavy and light variable domains as well as an Fc region.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end: the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service. National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

A "naked antibody" is an antibody (as herein defined) that is not conjugated to a heterologous molecule, such as a cytotoxic moiety or radiolabel.

Examples of Examples of anti-CD20 antibodies include: "C2B8," which is now called "rituximab" ("RITUXAN®/MABTHERA®") (U.S. Pat. No. 5,736,137); the yttrium-[90]-labelled 2B8 murine antibody designated "Y2B8" or "Ibritumomab Tiuxetan" (ZEVALIN®) commercially available from Biogen Idec, Inc. (e.g., U.S. Pat. No. 5,736,137; 2B8 deposited with ATCC under accession no. HB11388 on Jun. 22, 1993); murine IgG2a "B1," also called "Tositumomab," optionally labelled with $^{131}$I to generate the "131I-B1" or "iodine I131 tositumomab" antibody (BEXXAR™) commercially available from Corixa (see, also, e.g., U.S. Pat. No. 5,595,721); murine monoclonal antibody "1F5" (e.g., Press et al. Blood 69(2):584-591 (1987) and variants thereof including "framework patched" or humanized 1F5 (e.g., WO 2003/002607, Leung, S.; ATCC deposit HB-96450); murine 2H117 and chimeric 2H7 antibody (e.g., U.S. Pat. No. 5,677,180): a 2H7 antibody (e.g., WO 2004/056312 (Lowman et al.) and as set forth below); HUMAX-CD20™ (ofatumumab) fully human, high-affinity antibody targeted at the CD20 molecule in the cell membrane of B-cells (Genmab, Denmark; see, for example, Glennie and van de Winkel, Drug Discovery Today 8: 503-510 (2003) and Cragg et al., Blood 101: 1045-1052 (2003)); the human monoclonal antibodies set forth in WO 2004/035607 and WO 2005/103081 (Teeling et al., GenMab/Medarex); the antibodies having complex N-glycoside-linked sugar chains bound to the Fc region described in US 2004/0093621 (Shitara et al.); a chimerized or humanized monoclonal antibody having a high binding affinity to an extracellular epitope of a CD20 antigen described in WO 2006/106959 (Numazaki et al., Biomedics Inc.); monoclonal antibodies and antigen-binding fragments binding to CD20 (e.g., WO 2005/000901, Tedder et al.) such as HB20-3, HB20-4, HB20-25, and MB20-11; single-chain proteins binding to CD20 including, but not limited to, TRU-015 (e.g., US 2005/0186216 (Ledbetter and Hayden-Ledbetter); US 2005/0202534 (Hayden-Ledbetter and Ledbetter); US 2005/0202028 (Hayden-Ledbetter and Ledbetter); US 2005/136049 (Ledbetter et al.); US 2005/0202023 (Hayden-Ledbetter and Ledbetter)—Trubion Pharm Inc.); CD20-binding molecules such as the AME series of antibodies, e.g., AME-133™ antibodies as set forth, for example, in WO 2004/103404; US 2005/0025764; and US 2006/0251652 (Watkins et al., Applied Molecular Evolution, Inc.) and the anti-CD20 antibodies with Fc mutations as set forth, for example, in WO 2005/070963 (Allan et al., Applied Molecular Evolution, Inc.); CD20-binding molecules such as those described in WO 2005/016969 and US 2005/0069545 (Carr et al.); bispecific antibodies as set forth, for example, in WO 2005/014618 (Chang et al.); humanized LL2 monoclonal antibodies and other anti-CD20 antibodies as described, for example, in U.S. Pat. No. 7,151,164 (Hansen et al., Immunomedics; US 2005/0106108 (Leung and Hansen; Immunomedics); fully human antibodies against CD20 as described, e.g., in WO 2006/130458; Gazit et al., Amgen/AstraZeneca); antibodies against CD20 as described, for example, in WO 2006/126069 (Morawala, Avestha Gengraine Technologies Pvt Ltd.); chimeric or humanized B-Ly1 antibodies to CD20 (e.g., GA-101) as described, for example, in WO 2005/044859; US 2005/0123546; US 2004/0072290; and US 2003/0175884 (Umana et al.; GlycArt Biotechnology AG); A20 antibody or variants thereof such as chimeric or humanized A20 antibody (cA20, hA20, respectively) and IMMUN-106 (e.g., US 2003/0219433, Immunomedics); and monoclonal antibodies 127. G28-2, 93-1B3, B-C1 or NU-B2 available from the International Leukocyte Typing Workshop (e.g., Valentine et al., In: Leukocyte Typing III (McMichael, Ed., p. 440, Oxford University Press (1987)). In some embodiments, the anti-CD20 antibodies herein are chimeric, humanized, or human anti-CD20 antibodies, more preferably rituximab, a 2H7 antibody, chimeric or humanized A20 antibody (Immunomedics), and HUMAX-CD20™ human anti-CD20 antibody (Genmab).

The terms "Rituximab" or "RITUXAN®" herein refer to the genetically engineered chimeric murine/human monoclonal antibody directed against the CD20 antigen and designated "C2B8" in U.S. Pat. No. 5,736,137, including fragments thereof that retain the ability to bind CD20. Rituximab is commercially available from Genentech.

Purely for the purposes herein and unless indicated otherwise, "humanized 2H7" refers to a humanized antibody that binds human CD20, or an antigen-binding fragment thereof, wherein the antibody is effective to deplete primate B cells in vivo, the antibody comprising in the H chain variable region ($V_H$) thereof at least a CDR H3 sequence of SEQ ID NO: 12 (FIG. 1B) from an anti-human CD20 antibody and substantially the human consensus framework (FR) residues of the human heavy-chain subgroup III ($V_H$III). In some embodiments, this antibody further comprises the H chain CDR H1 sequence of SEQ ID NO:10 and CDR H2 sequence of SEQ ID NO: 11, and, in some embodiments, further comprises the L chain CDR L1 sequence of SEQ ID NO:4, CDR L2 sequence of SEQ ID NO:5, CDR L3 sequence of SEQ ID NO:6 and substantially the human consensus framework (FR) residues of the human light chain □ subgroup I (V□I), wherein the $V_H$ region may be joined to a human IgG chain constant region, wherein the region may be, for example, IgG1 or IgG3. In some embodiments, such antibody comprises the $V_H$ sequence of SEQ ID NO:8 (v16, as shown in FIG. 1B), optionally also comprising the $V_L$ sequence of SEQ ID NO:2 (v16, as shown in FIG. 1A), which may have the amino acid substitutions of D56A and N100A in the H chain and S92A in the L chain (v96).

In some embodiments, the antibody is an intact antibody comprising the light and heavy chain amino acid sequences of SEQ ID NOS:13 and 14, respectively, as shown in FIGS. 2 and 3. In some embodiments, the antibody is 2H7.v31 comprising the light and heavy chain amino acid sequences of SEQ ID NOS:13 and 15, respectively, as shown in FIGS. 2 and 4. The antibody herein may further comprise at least one amino acid substitution in the Fc region that improves ADCC and/or CDC activity, such as one wherein the amino acid substitutions are S298A/E333A/K334A, and in some embodiments, the 2H7.v31 having the heavy chain amino acid sequence of SEQ ID NO: 15 (as shown in FIG. 4). Any of these antibodies may further comprise at least one amino acid substitution in the Fc region that decreases CDC activity, for example, comprising at least the substitution K322A. See U.S. Pat. No. 6,528,624B1 (Idusogie et al.).

The term "Ocrelizumab" herein refers to the genetically engineered humanized monoclonal antibody directed against the CD20 antigen and comprising (a) a light chain comprising the amino acid sequence of SEQ ID NO: 13 and (b) a heavy chain comprising the amino acid sequence of SEQ ID NO: 14, including fragments thereof that retain the ability to bind CD20. Ocrelizumab is available from Genentech.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In some embodiments, the antibody will be purified (1) to greater than 95% by weight of antibody as determined by the Lowry method, and in some embodiments, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, in some embodiments, silver stain. Isolated antibody includes the antibody in situ within recombinant cells since at least one component of the antibody's natural environment will not be present. Ordinarily, however, isolated antibody will be prepared by at least one purification step.

A "subject" or "patient" herein is a human subject or patient. Generally, the subject or patient is eligible for treatment for multiple sclerosis. For the purposes herein, such eligible subject or patient is one who is experiencing, has experienced, or is likely to experience, one or more signs, symptoms or other indicators of multiple sclerosis; has been diagnosed with multiple sclerosis, whether, for example, newly diagnosed (with "new onset" MS), previously diagnosed with a new relapse or exacerbation, previously diagnosed and in remission, etc; and/or is at risk for developing multiple sclerosis. One suffering from or at risk for suffering from multiple sclerosis may optionally be identified as one who has been screened for elevated levels of CD20-positive B cells in serum, cerebrospinal fluid (CSF) and/or MS lesion(s) and/or is screened for using an assay to detect autoantibodies, assessed qualitatively, and preferably quantitatively. Exemplary such autoantibodies associated with multiple sclerosis include anti-myelin basic protein (MBP), anti-myelin oligodendrocytic glycoprotein (MOG), anti-ganglioside and/or anti-neurofilament antibodies. Such autoantibodies may be detected in the subject's serum, cerebrospinal fluid (CSF) and/or MS lesion. By "elevated" autoantibody or B cell level(s) herein is meant level(s) of such autoantibodies or B cells which significantly exceed the level(s) in an individual without MS.

As used herein, "treatment" or "treating" is an approach for obtaining beneficial or desired results including clinical results. For purposes of this invention, beneficial or desired clinical results include, but are not limited to, one or more of the following: decreasing one or more symptoms resulting from the disease, diminishing the extent of the disease, stabilizing the disease (e.g., preventing or delaying the worsening of the disease), delay or slowing the progression of the disease, ameliorating the disease state, decreasing the dose of one or more other medications required to treat the disease, and/or increasing the quality of life.

As used herein, "delaying" the progression of multiple sclerosis means to defer, hinder, slow, retard, stabilize, and/or postpone development of the disease. This delay can be of varying lengths of time, depending on the history of the disease and/or individual being treated.

As used herein, "at the time of starting treatment" refers to the time period at or prior to the first exposure to a multiple sclerosis drug, such as an anti-CD20 antibody. In some embodiments, "at the time of starting treatment" is about any of one year, nine months, six months, three months, second months, or one month prior to a multiple sclerosis drug, such as an anti-CD20 antibody. In some embodiments, "at the time of starting treatment" is immediately prior to coincidental with the first exposure to a multiple sclerosis drug, such as an anti-CD20 antibody.

As used herein, "based upon" includes (1) assessing, determining, or measuring the patient characteristics as described herein (and preferably selecting a patient suitable for receiving treatment; and (2) administering the treatment(s) as described herein.

A "symptom" of MS is any morbid phenomenon or departure from the normal in structure, function, or sensation, experienced by the subject and indicative of MS.

"Multiple sclerosis" refers to the chronic and often disabling disease of the central nervous system characterized by the progressive destruction of the myelin. There are four internationally recognized forms of MS, namely, primary progressive multiple sclerosis (PPMS), relapsing-remitting multiple sclerosis (RRMS), secondary progressive multiple sclerosis (SPMS), and progressive relapsing multiple sclerosis (PRMS).

"Progressive multiple sclerosis" as used herein refers to primary progressive multiple sclerosis (PPMS), secondary progressive multiple sclerosis (SPMS), and progressive relapsing multiple sclerosis (PRMS). In some embodiments, progressive multiple sclerosis is characterized by documented, irreversible loss of neurological function persisting for ≥6 months that cannot be attributed to clinical relapse.

"Primary progressive multiple sclerosis" or "PPMS" is characterized by a gradual progression of the disease from its onset with no superimposed relapses and remissions at all. There may be periods of a leveling off of disease activity and there may be good and bad days or weeks. PPMS differs from RRMS and SPMS in that onset is typically in the late thirties or early forties, men are as likely women to develop it, and initial disease activity is often in the spinal cord and not in the brain. PPMS often migrates into the brain, but is less likely to damage brain areas than RRMS or SPMS. For example, people with PPMS are less likely to develop cognitive problems than those with RRMS or SPMS. PPMS is the sub-type of MS that is least likely to show inflammatory (gadolinium enhancing) lesions on MRI scans. The Primary Progressive form of the disease affects between 10 and 15% of all people with multiple sclerosis. PPMS may be defined according to the criteria in McDonald et al. *Ann Neurol* 50:121-7 (2001). The subject with PPMS treated herein is usually one with probable or definitive diagnosis of PPMS.

"Relapsing-remitting multiple sclerosis" or "RRMS" is characterized by relapses (also known as exacerbations) during which time new symptoms can appear and old ones resurface or worsen. The relapses are followed by periods of remission, during which time the person fully or partially recovers from the deficits acquired during the relapse. Relapses can last for days, weeks or months and recovery can be slow and gradual or almost instantaneous. The vast majority of people presenting with MS are first diagnosed with RRMS. This is typically when they are in their twenties or thirties, though diagnoses much earlier or later are known. Twice as many women as men present with this sub-type of MS. During relapses, myelin, a protective insulating sheath around the nerve fibers (neurons) in the white matter regions of the central nervous system (CNS), may be damaged in an inflammatory response by the body's own immune system. This causes a wide variety of neurological symptoms that vary considerably depending on which areas of the CNS are damaged. Immediately after a relapse, the inflammatory response dies down and a special type of glial cell in the CNS (called an oligodendrocyte) sponsors remyelination—a process whereby the myelin sheath around the axon may be repaired. It is this remyelination that may be responsible for the remission. Approximately 50% of patients with RRMS convert to SPMS within 10 years of disease onset. After 30 years, this figure rises to 90%. At any one time, the relapsing-remitting form of the disease accounts around 55% of all people with MS.

"Secondary progressive multiple sclerosis" or "SPMS" is characterized by a steady progression of clinical neurological damage with or without superimposed relapses and minor remissions and plateaux. People who develop SPMS will have previously experienced a period of RRMS which may have lasted anything from two to forty years or more. Any superimposed relapses and remissions there are, tend to tail off over time. From the onset of the secondary progressive phase of the disease, disability starts advancing much quicker than it did during RRMS though the progress can still be quite slow in some individuals. After 10 years, 50% of people with RRMS will have developed SPMS. By 25 to 30 years, that figure will have risen to 90%. SPMS tends to be associated with lower levels of inflammatory lesion formation than in RRMS but the total burden of disease continues to progress. At any one time, SPMS accounts around 30% of all people with multiple sclerosis.

"Progressive relapsing multiple sclerosis" refers to "PRMS" is characterized by a steady progression of clinical neurological damage with superimposed relapses and remissions. There is significant recovery immediately following a relapse but between relapses there is a gradual worsening of symptoms. PRMS affects around 5% of all people with multiple sclerosis. Some neurologists believe PRMS is a variant of PPMS.

The expression "effective amount" refers to an amount of the antibody (or other drug) that is effective for ameliorating or treating the multiple sclerosis. Such an effective amount will generally result in an improvement in the signs, symptoms or other indicators of MS, such as reducing relapse rate, preventing disability, reducing number and/or volume of brain MRI lesions, improving timed 25-foot walk, slow or delay the progression of the disease such as extending the time to disease progression (e.g. using Expanded Disability Status Scale, EDSS), etc.

"Antibody exposure" refers to contact with or exposure to the antibody herein in one or more doses administered over a period of time of about 1-20 days. The doses may be given at one time or at fixed or irregular time intervals over this period of exposure. Initial and later (e.g. second or third) antibody exposures are separated in time from each other as described in detail herein.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); nonsteroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antagonists including anti-interferon-alpha, -beta, or -gamma antibodies, anti-tumor necrosis factor-alpha antibodies (infliximab or adalimumab), anti-TNF-alpha immunoahesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies: soluble peptide containing a LFA-3 binding domain (WO 90/08187 published Jul. 26, 1990); streptokinase; TGF-beta; streptodornase; RNA or DNA from the host; FK506: RS-61443; deoxyspergualin; rapamycin; T-cell receptor (Cohen et al., U.S. Pat. No. 5,114,721); T-cell receptor fragments (Offner et al., *Science,* 251: 430-432 (1991); WO 90/11294; Ianeway, *Nature,* 341: 482 (1989); and WO 91/01133); and T cell receptor antibodies (EP 340,109) such as T10B9.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocannycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, camofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan: lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine): urethan; vindesine; dacarbazine; mannomustine; mitobronitol; mitolactol: pipobroman; gacytosine; arabinoside ("Ara-C"): cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide: edatrexate; daunomycin; aminopterin; xeloda; ibandronate; CPT-11; topoisomerase inhibitor RFS 2000; ditluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tanoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Ralf and H-Ras; vaccines such as gene therapy vaccines, for example, ALLOVECTIN® vaccine, LEU-VECTIN® vaccine, and VAXID® vaccine; PROLEUKIN® rIL-2; LURTOTECAN® topoisomerase 1 inhibitor: ABARELIX® rmRH; and pharmaceutically acceptable salts, acids or derivatives of any of the above.

The term "cytokine" is a generic term for proteins released by one cell population that act on another cell as intercellular mediators. Examples of such cytokines are lymphokines, monokines; interleukins (ILs) such as IL-1, IL-1α, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines, including synthetically produced small-molecule entities and pharmaceutically acceptable derivatives and salts thereof.

The term "hormone" refers to polypeptide hormones, which are generally secreted by glandular organs with ducts. Included among the hormones are, for example, growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); prolactin, placental lactogen, mouse gonadotropin-associated peptide, inhibin; activin; mullerian-inhibiting substance; and thrombopoietin. As used herein, the term hormone includes proteins from natural sources or from recombinant cell culture and biologically active equivalents of the native sequence hormone, including synthetically produced small-molecule entities and pharmaceutically acceptable derivatives and salts thereof.

The term "growth factor" refers to proteins that promote growth, and include, for example, hepatic growth factor; fibroblast growth factor; vascular endothelial growth factor; nerve growth factors such as NGF-β; platelet-derived growth factor; transforming growth factors (TGFs) such as TGF-α and TGF-β; insulin-like growth factor-I and -II; erythropoietin (EPO); osteoinductive factors; interferons such as interferon-α, -β, and -γ; and colony stimulating factors (CSFs) such as macrophage-CSF (M-CSF); granulocyte-macrophage-CSF (GM-CSF); and granulocyte-CSF (G-CSF). As used herein, the term growth factor includes proteins from natural sources or from recombinant cell culture and biologically active equivalents of the native sequence growth factor, including synthetically produced small-molecule entities and pharmaceutically acceptable derivatives and salts thereof.

The term "integrin" refers to a receptor protein that allows cells both to bind to and to respond to the extracellular matrix and is involved in a variety of cellular functions such as wound healing, cell differentiation, homing of tumor cells and apoptosis. They are part of a large family of cell adhesion receptors that are involved in cell-extracellular matrix and cell-cell interactions. Functional integrins consist of two transmembrane glycoprotein subunits, called alpha and beta that are non-covalently bound. The alpha subunits all share some homology to each other, as do the beta subunits. The receptors always contain one alpha chain and one beta chain. Examples include Alpha6beta1, Alpha3beta1, Alpha7beta1, LFA-1, alpha 4 integrin etc. As used herein, the term integrin includes proteins from natural sources or from recombinant cell culture and biologically active equivalents of the native sequence integrin, including synthetically produced small-molecule entities and pharmaceutically acceptable derivatives and salts thereof.

Examples of "integrin antagonists or antibodies" herein include an LFA-1 antibody such as Efalizumab (RAPTIVA®) commercially available from Genentech; an alpha 4 integrin antibody such as natalizumab (TYSABRI®) available from Biogen Idec/Elan Pharmaceuticals, Inc.; diazacyclic phenylalanine derivatives (WO 2003/89410); phenylalanine derivatives (WO 2003/70709, WO 2002/28830, WO 2002/16329 and WO 2003/53926); phenylpropionic acid derivatives (WO 2003/10135); enamine derivatives (WO 2001/79173); propanoic acid derivatives (WO 2000/37444); alkanoic acid derivatives (WO 2000/32575); substituted phenyl derivatives (U.S. Pat. Nos. 6,677,339 and 6,348,463); aromatic amine derivatives (U.S. Pat. No. 6,369,229); and ADAM disintegrin domain polypeptide (US2002/0042368), antibodies to alphavbeta3 integrin (EP 633945); aza-bridged bicyclic amino acid derivatives (WO 2002/02556) etc.

For the purposes herein. "tumor necrosis factor alpha (TNF-alpha)" refers to a human TNF-alpha molecule comprising the amino acid sequence as described in Pennica et al., *Nature,* 312:721 (1984) or Aggarwal et al., *JBC,* 260: 2345 (1985).

A "TNF-alpha inhibitor" herein is an agent that inhibits, to some extent, a biological function of TNF-alpha, generally through binding to TNF-alpha and neutralizing its activity. Examples of TNF inhibitors specifically contemplated herein are Etanercept (ENBREL®), Infliximab (REMICADE®) and Adalimumab (HUMIRA™).

Examples of "disease-modifying anti-rheumatic drugs" or "DMARDs" include hydroxycloroquine, sulfasalazine, methotrexate, leflunomide, etanercept, infliximab (plus oral and subcutaneous methrotrexate), azathioprine, D-penicillamine, Gold (oral), Gold (intramuscular), minocycline, cyclosporine, Staphylococcal protein A immunoadsorption, including salts and derivatives thereof, etc.

Examples of "nonsteroidal anti-inflammatory drugs" or "NSAIDs" are acetylsalicylic acid, ibuprofen, naproxen, indomethacin, sulindac, tolmetin, including salts and derivatives thereof, etc.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone, glucocorticoid and betamethasone.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

A "label" is used herein to refer to information customarily included with commercial packages of pharmaceutical formulations including containers such as vials and package inserts, as well as other types of packaging.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Treatment

The present invention provides methods of treating progressive multiple sclerosis in a patient comprising administering to the patient an effective amount of an anti-CD20 antibody.

In some embodiments, the invention provides methods of treating progressive multiple sclerosis in a patient comprising administering to the patient an effective amount of an anti-CD20 antibody, wherein treatment is based upon the patient having one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments, the invention provides methods of treating progressive multiple sclerosis in a patient provided that the patient has been found to have one or more characteristics selected from the group consisting of (a) an age less than about 55 years, (b) one or more gadolinium staining lesions, (c) at least about a one point increase in Expanded Disability Status Scale (EDSS) over two years prior to starting the treatment, and (d) a Multiple Sclerosis Severity Score (MSSS) greater than about 5 points, the treatment comprising administering to the patient an effective amount of an anti-CD20 antibody.

In some embodiments, the invention provides methods of treating progressive multiple sclerosis in a patient comprising administering to the patient an effective amount of an anti-CD20 antibody, wherein the patient has at the time of starting treatment one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, whereby evidence of the age, the gadolinium staining lesions, the increase in EDDS over two years prior to starting the treatment, MSSS, or a combination thereof indicates that the patient will respond to treatment with the anti-CD20 antibody.

In some embodiments, the invention provides methods of treating progressive multiple sclerosis, comprising: (a) selecting a patient has one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; and (b) administering to the patient thus selected an effective amount of an anti-CD20 antibody.

In some embodiments, the invention provides methods of treating progressive multiple sclerosis in a patient, comprising administering to the patient an effective amount of an anti-CD20 antibody, and wherein one or more characteristics selected from the group consisting of (a) an age less than about 55 years, (b) one or more gadolinium staining lesions. (c) at least about a one point increase in Expanded Disability Status Scale (EDSS) over two years prior to starting treatment, and (d) a Multiple Sclerosis Severity Score (MSSS) greater than about 5 points is used as a basis for selecting the patient to receive the treatment, and wherein said treatment comprises administering an effective amount of the anti-CD20 antibody to the patient.

The invention further provides methods of treating multiple sclerosis in a patient comprising administering an effective amount of ocrelizumab to the patient to provide an initial ocrelizumab exposure of between about 0.3 to about 0.6 grams followed by a second ocrelizumab exposure of between about 0.3 to about 0.6 grams, the second exposure not being provided until from about 16 to 60 weeks from the initial exposure, and each of the ocrelizumab exposures is provided to the patient as one or two doses of ocrelizumab. In some embodiments, the initial ocrelizumab exposure is about 0.6 grams. In some embodiments, the second ocrelizumab exposure is about 0.6 grams. In some embodiments, the second exposure is administered from about 24 weeks from the initial exposure. In some embodiments, one or more of the ocrelizumab exposures are provided to the patient as one dose of ocrelizumab. In some embodiments, one or more of the ocrelizumab exposures are provided to the patient as two doses of ocrelizumab. In some embodiments, the two doses of ocrelizumab comprise about 0.3 grams of ocrelizumab.

The present invention also provides methods of assessing and/or predicting responsiveness of a patient with progressive multiple sclerosis to an anti-CD20 antibody treatment.

In some embodiments, the invention provides methods of assessing whether a patient with progressive multiple sclerosis will respond to treatment with an anti-CD20 antibody comprising assessing one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, wherein one or more of the characteristics in the patient indicates the patient will be responsive to the treatment.

In some embodiments, the invention provides methods of assessing whether a patient with progressive multiple sclerosis will respond to treatment with an anti-CD20 antibody comprising: (a) assessing one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; (b) implementing an algorithm to determine that the patient is responsive to said treatment; and (c) recording a result specific to the patient being tested.

In some embodiments, the invention provides methods of treating progressive multiple sclerosis in a patient comprising: (a) assessing one or more characteristics selected from the group consisting of (i) an age less than about 55 years, (i) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points, wherein the patient is selected for treatment based on the patient having one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; and (b) treating said selected patient by administering to said selected patient an effective amount of an anti-CD20 antibody.

In some embodiments, the invention provides methods for selecting a therapy for a patient and/or a patient population with progressive multiple sclerosis comprising: (a) assessing one or more characteristics selected from the group consisting of (i) an age less than about 55 years. (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; and (b) selecting an anti-CD20 antibody for treatment if the patient or patient population has one or more characteristics selected from the group consisting of (i) an age less than about 55 years, (ii) one or more gadolinium staining lesions, (iii) at least about a one point increase in Expanded Disability Status Scale (EDSS) over two years prior to starting the anti-CD20 treatment, and (iv) a Multiple Sclerosis Severity Score (MSSS) greater than about 5 points.

In some embodiments, the invention provides methods for predicting whether a patient with progressive multiple sclerosis will respond to an anti-CD20 antibody, the methods comprising assessing one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, whereby the age, the gadolinium staining lesions, the increase in EDDS over two years prior to starting treatment, MSSS, or a combination thereof indicates that the patient will respond to the anti-CD20 antibody.

In some embodiments, the invention provides methods of identifying a patient with progressive multiple sclerosis likely to respond to anti-CD20 antibody treatment comprising: (a) assessing one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; and (b) identifying the patient having one or more characteristics selected from the group consisting of (i)

an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points.

In some embodiments of any of the methods of treating, assessing, and/or predicting responsiveness described herein, the patients have one or more characteristics selected from the group consisting of (a) an age less than about 55 years, (b) one or more gadolinium staining lesions, and (c) at least about a one point increase in Expanded Disability Status Scale (EDSS) over two years prior to starting treatment.

In some embodiments of any of the methods of assessing and/or predicting responsiveness described herein, the methods further comprise advising a patient.

In some embodiments of any of the methods of treating and assessing and/or predicting responsiveness described herein, the patient has more than one characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments of any of the methods of treating and assessing and/or predicting responsiveness described herein, the patient has two characteristics selected from the group consisting of (a) an age less than about 55 years. (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has three characteristics selected from the group consisting of (a) an age less than about 55 years, (b) one or more gadolinium staining lesions, and (c) at least about a one point increase in EDSS over two years prior to starting treatment. In some embodiments, the patient has (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the methods of treating and assessing and/or predicting responsiveness described herein, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient and/or patient population is not diagnosed with relapsing remitting multiple sclerosis when starting treatment.

In some embodiments of any of the methods of treating and assessing and/or predicting responsiveness described herein, the patient and/or patient population further has evidence of inflammation in a sample. Evidence of inflammation is indicated by assessing one or more indicia of inflammation. The sample can be any suitable sample to assess inflammation. In some embodiments, the sample is tissue or fluid. In some embodiments, the fluid sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing. In some embodiments, the evidence of inflammation is detected by MRI. In some embodiments, the evidence of inflammation is detected by the presence of Gd-enhancing lesions or T2 lesions. Other methods of assessing evidence of inflammation are known in the art.

In some embodiments of any of the methods of treating and assessing and/or predicting responsiveness described herein, the patient and/or patient population is characterized by a change in EDSS over a period of time. In some embodiments, the patient and/or patient population is characterized by at least about any of 1 point, 1.25 point, 1.5 point, 1.75 point, 2 point, 2.25 point, 2.5 point, 2.75 point, or 3 point increase in EDSS over two years prior to starting the anti-CD20 antibody treatment. In some embodiments, the increase in EDSS is at least about a 1.5 point increase in EDSS over two years prior to starting treatment. In some embodiments, the increase in EDSS over two years prior to starting treatment is not attributable to relapse. In some embodiments, the patient and/or patient population is characterized by having had an EDSS of greater than about 5.0 for less than about any of 5 years, 6 years, 7 years, 8 years, 9 years, 10 years, 11 years, 12 years, 13 years, 14 years, 15 years, 16 years, 17 years, 18 years, 19 years, or 20 years. In some embodiments, the patient and/or patient population is characterized by having had an EDSS of greater than about 5.0 for less than about 15 years. In some embodiments, the patient and/or patient population is characterized by having had an EDSS less than or equal to about 5.0 for less than about any of 5 years, 6 years, 7 years, 8 years, 9 years, 10 years, 11 years, 12 years, 13 years, 14 years, or 15 years. In some embodiments, the patient and/or patient population is characterized by having had an EDSS less than or equal to about 5.0 for less than about 10 years.

In some embodiments of any of the methods of treating and assessing and/or predicting responsiveness described herein, the patient and/or patient population is characterized by having an EDSS of between about any of 1.5 points to 7 points, 1.5 points to 6.5 points, 2 points to 6.5 points, or 3 points to 6.5 points. In some embodiments, the patient and/or patient population is characterized by having an EDSS when starting treatment is between about 3.0 and about 6.5.

In some embodiments of any of the methods of treating, assessing and/or predicting responsiveness described herein, the patient and/or patient population is characterized by having an MSSS of greater than about any of 6, 7, 8, or 9. In some embodiments of any of the methods of treating and assessing and/or predicting responsiveness described herein, the patient and/or patient population is characterized by having an MSSS of greater than about 9.

In some embodiments of any of the methods of treating and assessing and/or predicting responsiveness described herein, the patient and/or patient population is further characterized by having two or more relapses within two years prior to starting treatment. In some embodiments, the patient and/or patient population is further characterized by having any of 2 relapses, 3 relapses, 4 relapses, or 5 relapses within two years prior to starting treatment.

In some embodiments of any of the methods of treating and assessing and/or predicting responsiveness described herein, the patient and/or patient population is characterized by an age. In some embodiments, the patient and/or patient population is characterized by having an age less than about any of 55 years, 54 years, 53 years, 52 years, 51 years, or 50 years. In some embodiments, the patient and/or patient population is characterized by having an age of less than about 51 years.

In some embodiments of any of the methods of treating and assessing and/or predicting responsiveness described herein, the treatment reduces time to confirmed disease progression. In some embodiments, the confirmed disease progression is an increase in EDSS that is sustained for about any of 4 weeks, 8 weeks, 12 weeks, 16 weeks, 20 weeks, 24 weeks, 28 weeks, or 32 weeks. In some embodiments, the confirmed disease progression is an increase in EDSS that is sustained for twelve weeks. In some embodiments, the confirmed disease progression is an increase in EDSS that is sustained for twenty-four weeks.

In some embodiments of any of the methods of treating and assessing and/or predicting responsiveness described herein, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments of any of the methods described herein, the anti-CD20 antibody is ocrelizumab. In some embodiments of any of the methods described herein, the anti-CD20 antibody is rituximab. In some embodiments of any of the methods described herein, the anti-CD20 antibody is ofatumumab. In some embodiments of any of the methods described herein, the anti-CD20 antibody is TRU-015 or SBI-087. In some embodiments of any of the methods described herein, the anti-CD20 antibody is GA101. In some embodiments of any of the methods described herein, the anti-CD20 antibody is hA20.

The methods described herein may encompass any combination of the embodiments described herein. For example, the methods include methods of treatment and assessing and/or predicting wherein the patient has (a) an age less than about 55 years and (b) one or more gadolinium staining lesions.

III. Dosages

According to some embodiments of any of the methods or articles of manufacture described herein, the method or instructions comprises administering an effective amount of an anti-CD20 antibody to the multiple sclerosis patient to provide an initial antibody exposure of about 0.3 to about 4 grams (preferably about 0.3 to about 1.5 grams, such as about 0.6 grams or about 1.0 grams) followed by a second antibody exposure of about 0.3 to about 4 grams (preferably about 0.3 to about 1.5 grams, such as about 0.6 grams or about 1.0 grams), the second antibody exposure not being provided until from about 16 to about 60 weeks from the initial antibody exposure. For purposes of this invention, the second antibody exposure is the next time the patient is treated with the anti-CD20 antibody after the initial antibody exposure, there being no intervening anti-CD20 antibody treatment or exposure between the initial and second exposures. In some embodiments, the initial antibody exposure and/or the second antibody exposure is about any of 0.3 grams, 0.4 grams, 0.5 grams, 0.6 grams, 0.7 grams, 0.8 grams, 0.9 grams, or 1.0 grams.

The interval between the initial and second or subsequent antibody exposures can be measured from either the first or second dose of the initial antibody exposure, but in some embodiments, from the first dose of the initial antibody exposure.

In some embodiments, the antibody exposures are approximately 24 weeks or 6 months apart; or approximately 48 weeks or 12 months apart.

In one embodiment, the second antibody exposure is not provided until about 20 to about 30 weeks from the initial exposure, optionally followed by a third antibody exposure of about 0.3 to about 4 grams (preferably about 0.3 to about 1.5 grams), the third exposure not being administered until from about 46 to 60 weeks (preferably from about 46 to 54 weeks) from the initial exposure, and then, in some embodiments, no further antibody exposure is provided until at least about 70-75 weeks from the initial exposure. In some embodiments, the third antibody exposure is about any of 0.3 grams, 0.4 grams, 0.5 grams, 0.6 grams, 0.7 grams, 0.8 grams, 0.9 grams, or 1.0 grams.

In an alternative embodiment, the second antibody exposure is not provided until about 46 to 60 weeks from the initial exposure, and subsequent antibody exposures, if any, are not provided until about 46 to 60 weeks from the previous antibody exposure.

Any one or more of the antibody exposures herein may be provided to the patient as a single dose of antibody, or as two separate doses of the antibody (i.e., constituting a first and second dose). The particular number of doses (whether one or two) employed for each antibody exposure is dependent, for example, on the type of MS treated, the type of antibody employed, whether and what type of second medicament is employed, and the method and frequency of administration. Where two separate doses are administered, the second dose is preferably administered from about 3 to 17 days, more preferably from about 6 to 16 days, and most preferably from about 13 to 16 days from the time the first dose was administered. In some embodiments, where two separate doses are administered, the second dose is about 14 days. Where two separate doses are administered, the first and second dose of the antibody is preferably about 0.3 to 1.5 grams, more preferably about 0.3 to about 1.0 grams. In some embodiments, where two separate doses are administered, the first and second dose of the antibody is about any of 0.3 grams, 0.4 grams, 0.5 grams, or 0.6 grams. In some embodiments, the initial ocrelizumab exposure comprises a first dose and a second dose of ocrelizumab, wherein the first dose and second dose of ocrelizumab is about 0.3 grams. In some embodiments, the second ocrelizumab exposure comprises a single dose of ocrelizumab, wherein the single dose of ocrelizumab is 0.6 grams.

In one embodiment, the patient is provided at least about three, at least about four, or at least about five exposures of the antibody, for example, from about 3 to 60 exposures, and more particularly about 3 to 40 exposures, most particularly, about 3 to 20 exposures. In some embodiments of any of the methods, the methods further comprising providing between about one to about three subsequent ocrelizumab exposures. In some embodiments, such exposures are administered at intervals each of approximately 24 weeks or 6 months, or 48 weeks or 12 months. In one embodiment, each antibody exposure is provided as a single dose of the antibody. In an alternative embodiment, each antibody exposure is provided as two separate doses of the antibody. However, not every antibody exposure need be provided as a single dose or as two separate doses.

The antibody may be a naked antibody or may be conjugated with another molecule such as a cytotoxic agent such as a radioactive compound. In some embodiments, the antibody is Rituximab, humanized 2H7 (e.g. comprising the variable domain sequences in SEQ ID NOS. 2 and 8) or humanized 2H7 comprising the variable domain sequences in SEQ ID NOS. 23 and 24, or huMax-CD20 (Genmab). In some embodiments, the antibody is ocrelizumab (e.g., comprising (a) a light chain comprising the amino acid sequence of SEQ ID NO: 13 and (b) a heavy chain comprising the amino acid sequence of SEQ ID NO: 14).

In one embodiment, the patient has never been previously treated with drug(s), such as immunosuppressive agent(s), to treat the multiple sclerosis and/or has never been previously treated with an antibody to a B-cell surface marker (e.g. never previously treated with a CD20 antibody).

The antibody is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated (see, e.g., US Patent Appln No. 2002/0009444, Grillo-Lopez, A concerning intrathecal delivery of a CD20 antibody). In addition, the antibody may suitably be administered by pulse infusion, e.g., with declining doses of the antibody. In some embodiments, the dosing is given intravenously, subcutaneously or intrathecally. In some embodiments, the dosing is given by intravenous infusion(s).

While the CD20 antibody may be the only drug administered to the patient to treat the multiple sclerosis, one may optionally administer a second medicament, such as a cytotoxic agent, chemotherapeutic agent, immunosuppressive agent, cytokine, cytokine antagonist or antibody, growth factor, hormone, integrin, integrin antagonist or antibody (e.g. an LFA-1 antibody such as efalizumab (RAPTIVA®) commercially available from Genentech, or an alpha 4 integrin antibody such as natalizumab (TYSABRI®) available from Biogen Idec/Elan Pharmaceuticals, Inc) etc, with the antibody that binds a B cell surface marker (e.g. with the CD20 antibody).

In some embodiments of combination therapy, the antibody is combined with an interferon class drug such as IFN-beta-1a (REBIF® and AVONEX®) or IFN-beta-1b (BETASERON®); an oligopeptide such a glatiramer acetate (COPAXONE®) a cytotoxic agent such as mitoxantrone (NOVANTRONE®), methotrexate, cyclophosphamide, chlorambucil, azathioprine; intravenous immunoglobulin (gamma globulin); lymphocyte-depleting therapy (e.g., mitoxantrone, cyclophosphamide. Campath, anti-CD4, cladribine, total body irradiation, bone marrow transplantation); corticosteroid (e.g. methylprednisolone, prednisone, dexamethasone, or glucorticoid), including systemic corticosteroid therapy; non-lymphocyte-depleting immunosuppressive therapy (e.g., mycophenolate mofetil (MMF) or cyclosporine); cholesterol-lowering drug of the "statin" class, which includes cerivastatin (BAYCOL®), fluvastatin (LESCOL®), atorvastatin (LIPITOR®), lovastatin (MEVACOR®), pravastatin (PRAVACHOL®), Simvastatin (ZOCOR®); estradiol; testosterone (optionally at elevated dosages; Stuve et al. *Neurology* 8:290-301 (2002)); hormone replacement therapy; treatment for symptoms secondary or related to MS (e.g., spasticity, incontinence, pain, fatigue); a TNF inhibitor, disease-modifying anti-rheumatic drug (DMARD); non-steroidal anti-inflammatory drug (NSAID); plasmapheresis; levothyroxine; cyclosporin A; somatastatin analogue; cytokine or cytokine receptor antagonist; antimetabolite; immunosuppressive agent; rehabilitative surgery; radioiodine; thyroidectomy; another B-cell surface antagonist/antibody; etc.

The second medicament is administered with the initial exposure and/or later exposures of the CD20 antibody, such combined administration includes co-administration, using separate formulations or a single pharmaceutical formulation, and consecutive administration in either order, wherein preferably there is a time period while both (or all) active agents simultaneously exert their biological activities.

Aside from administration of antibodies to the patient, the present application contemplates administration of antibodies by gene therapy. Such administration of nucleic acid encoding the antibody is encompassed by the expression administering an "effective amount" of an antibody. See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes that are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

In some embodiments, the in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins that bind to a cell surface membrane protein associated with endocytosis may be used for targeting and/or to facilitate uptake, e.g. capsid proteins or fragments thereof tropic for a particular cell type, antibodies for proteins that undergo internalization in cycling, and proteins that target intracellular localization and enhance intracellular half-life. The technique of receptor-mediated endocytosis is described, for example, by Wu et al., *J. Biol. Chem.* 262: 4429-4432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

IV. Antibodies and their Production

The methods and articles of manufacture of the present invention use, or incorporate, an antibody that binds to a B-cell surface marker, especially one that binds to CD20. Accordingly, methods for generating such antibodies will be described here.

The B cell surface marker to be used for production of, or screening for, antibodies may be, e.g., a soluble form of the marker or a portion thereof, containing the desired epitope. Alternatively, or additionally, cells expressing the marker at their cell surface can be used to generate, or screen for, antibodies. Other forms of the B cell surface marker useful for generating antibodies will be apparent to those skilled in the art.

A description follows as to exemplary techniques for the production of the antibodies used in accordance with the present invention.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

In a further embodiment, antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151:2296 (1993): Chothia et al., *J. Mol. Biol.*, 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

In some embodiments, the humanized anti-CD20 antibody is a humanized 2H7 antibody. In some embodiments, the humanized 2H7 antibody preferably comprises one, two, three, four, five or six of the following CDR sequences:

CDR L1 sequence RASSSVSYXH wherein X is M or L (SEQ ID NO. 18), for example SEQ ID NO:4 (FIG. 1A), CDR L2 sequence of SEQ ID NO:5 (FIG. 1A), CDR L3 sequence QQWXFNPPT wherein X is S or A (SEQ ID NO. 19), for example SEQ ID NO:6 (FIG. 1A), CDR H1 sequence of SEQ ID NO:10 (FIG. 1B), CDR H2 sequence of AIYPGNGXTSYNQKFKG wherein X is D or A (SEQ ID NO. 20), for example SEQ ID NO:11 (FIG. 1B), and CDR H3 sequence of VVYYSXXYWYFDV wherein the X at position 6 is N, A, Y, W or D, and the X as position 7 is S or R (SEQ ID NO. 21), for example SEQ ID NO: 12 (FIG. 1B).

The CDR sequences above are generally present within human variable light and variable heavy framework sequences, such as substantially the human consensus FR residues of human light chain kappa subgroup I ($V_L6I$), and substantially the human consensus FR residues of human heavy chain subgroup III ($V_HIII$). See also WO 2004/056312 (Lowman et al.).

In some embodiments, the variable heavy region may be joined to a human IgG chain constant region, wherein the region may be, for example, IgG1 or IgG3, including native sequence and variant constant regions.

In some embodiments, such antibody comprises the variable heavy domain sequence of SEQ ID NO:8 (v16, as shown in FIG. 1B), optionally also comprising the variable light domain sequence of SEQ ID NO:2 (v16, as shown in FIG. 1A), which optionally comprises one or more amino acid substitution(s) at positions 56, 100, and/or 100a, e.g. D56A, N100A or N100Y, and/or S100aR in the variable heavy domain and one or more amino acid substitution(s) at positions 32 and/or 92, e.g. M32L and/or S92A, in the variable light domain. In some embodiments, the antibody is an intact antibody comprising the light chain amino acid sequences of SEQ ID NOs. 13 or 16, and heavy chain amino acid sequences of SEQ ID NO. 14, 15, 17, 22 or 25. In some embodiments, the humanized 2H7 antibody is ocrelizumab (Genentech).

In the embodiments, the humanized 2H7 is an intact antibody or antibody fragment comprising the variable light chain sequence:

```
                                               (SEQ ID NO: 2)
DIQMTQSPSSLSASVGDRVTITCRASSSVSYMHWYQQKPGKAPKPLIYAP

SNLASGVPSRFSGSGSGTDFTLTISSLQPEDFATYYCQQWSFNPPTFGQG

TKVEIKR;
``` and the variable heavy chain sequence:

```
                                               (SEQ ID NO: 8)
EVQLVESGGGLVQPGGSLRLSCAASGYTFTSYNMHWVRQAPGKGLEWVGA
```

```
IYPGNGDTSYNQKFKGRFTISVDKSKNTLYLQMNSLRAEDTAVYYCARVV

YYSNSYWYFDVWGQGTLVTVSS.
```

In some embodiments, the humanized 2H7 antibody is an intact antibody, in some embodiments, it comprises the light chain amino acid sequence:

```
                                           (SEQ ID NO: 13)
DIQMTQSPSSLSASVGDRVTITCRASSSVSYMHWYQQKPGKAPKPLIYAP

SNLASGVPSRFSGSGSGTDFTLTISSLQPEDFATNYCQQWSFNPPTFGQG

TKVEIKRYVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC;
``` and the heavy chain amino acid sequence:

```
                                           (SEQ ID NO: 14)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

VYYSNSYWYFDVWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLS

PGK
``` or the heavy chain amino acid sequence:

```
                                           (SEQ ID NO: 15)
EVQLVESGGGLVQPGGSLRLSCAASGYTFTSYNMHWVRQAPGKGLEWVGA

IYPGNGDTSYNQKFKGRFTISVDKSKNTLYLQMNSLRAEDTAVYYCARVV

YYSNSYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNKALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK.
```

In some embodiments, the humanized 2H7 antibody comprises 2H7.v511 variable light domain sequence:

```
                                           (SEQ ID NO: 23)
DIQMTQSPSSLSASVGDRVTITCRASSSVSYLHWYQQKPGKAPKPLIYAP

SNLASGVPSRFSGSGSGTDFTLTISSLQPEDFATYYCQQWAFNPPTFGQG

TKVEIKR
``` and 2H7.v511 variable heavy domain sequence:

```
                                           (SEQ ID NO. 24)
EVQLVESGGGLVQPGGSLRLSCAASGYTFTSYNMHWVRQAPGKGLEWVG

AIYPGNGATSYNQKFKGRFTISVDKSKNTLYLQMNSLRAEDTAVYYCAR

VVYYSYRYWYFDVWGQGILVTVSS.
```

In some embodiments, the humanized 2H7.v511 antibody is an intact antibody, it may comprise the light chain amino acid sequence:

```
                                           (SEQ ID NO: 16)
DIQMTQSPSSLSASVGDRVTITCRASSSVSYLHWYQQKPGKAPKPLIYA

PSNASGVPSRFSGSGSGTDFTLTISSLQPEDFATYYCQQWAFNPPTFGQ

GTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTH

QGLSSPVTKSFNRGEC
``` and the heavy chain amino acid sequence of SEQ ID NO. 17 or:

```
                                           (SEQ ID NO: 25)
EVQLVESGGGLVQPGGSLRLSCAASGYTFTSYNMHWVRQAPGKGLEWVGA

IYPGNGATSYNQKFKGRFTISVDKSKNTLYLQMNSERAEDTAVYYCARVV

YYSYRYWYFDVWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNATYRVVSVLTVLHQDWLNGKEYKCKVSNAALPAPIAATISKAKGQPRE

PQVYTLPPSREEMTKNQVSLTCLVKGFYPSDIAVEWESNGQPENNYKTIP

PVLDSDGSFFLYSKLTVDKSRWQQGNVFSCSVMHEALHNHYTQKSLSLSP

G.
```

In some embodiments, the antibody herein may further comprise at least one amino acid substitution in the Fc region that improves ADCC activity, such as one wherein the amino acid substitutions are at positions 298, 333, and 334, preferably S298A, E333A, and K334A, using Eu numbering of heavy chain residues. See also U.S. Pat. No. 6,737,056B1, Presta. Any of these antibodies may comprise at least one substitution in the Fc region that improves FcRn binding or serum half-life, for example a substitution at heavy chain position 434, such as N434W. See also U.S. Pat. No. 6,737,056B1, Presta. Any of these antibodies may further comprise at least one amino acid substitution in the Fc region that increases CDC activity, for example, comprising at least a substitution at position 326, preferably K326A or K326W. See also U.S. Pat. No. 6,528,624B1 (Idusogie et al.).

In some embodiments, the humanized 2H7 variants are those comprising the variable light domain of SEQ ID NO:2 and the variable heavy domain of SEQ ID NO:8, including those with or without substitutions in an Fc region (if present), and those comprising a variable heavy domain with alteration N100A; or D56A and N100A; or D56A, N100Y, and S100aR; in SEQ ID NO:8 and a variable light domain with alteration M32L; or S92A: or M32L and S92A; in SEQ ID NO:2. M34 in the variable heavy domain of 2H7.v16 has been identified as a potential source of antibody stability and is another potential candidate for substitution.

In some embodiments of the invention, the variable region of variants based on 2H7.v16 comprise the amino acid sequences of v16 except at the positions of amino acid substitutions that are indicated in the table below. Unless otherwise indicated, the 2H7 variants will have the same light chain as that of v16.

TABLE 1

Exemplary Humanized 2H7 Antibody Variants

| 2H7 Version | Heavy chain ($V_H$) changes | Light chain ($V_L$) changes | Fc changes |
|---|---|---|---|
| 16 for reference | — | — | — |
| 31 | — | — | S298A, E333A, K334A |
| 73 | N100A | M32L | |
| 75 | N100A | M32L | S298A, E333A, K334A |
| 96 | D56A, N100A | S92A | |
| 114 | D56A, N100A | M32L, S92A | S298A, E333A, K334A |
| 115 | D56A, N100A | M32L, S92A | S298A, E333A, K334A, E356D, M358L |
| 116 | D56A, N100A | M32L, S92A | S298A, K334A, K322A |
| 138 | D56A, N100A | M32L, S92A | S298A, E333A, K334A, K326A |
| 477 | D56A, N100A | M32L, S92A | S298A, E333A, K334A, K326A, N434W |
| 375 | — | — | K334L |
| 588 | — | — | S298A, E333A, K334A, K326A |
| 511 | D56A, N100Y, S100aR | M32L, S92A | S298A, E333A, K334A, K326A |

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993): Bruggermann et al., *Year in Immuno.,* 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g. Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

Various techniques have been developed for the production of antibody fragments.

Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the B cell surface marker. Other such antibodies may bind the B cell surface marker and further bind a second different B-cell surface marker. Alternatively, an anti-B cell surface marker binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell surface marker-binding arm and an arm that binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. $F(ab')_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

V. Conjugates and Other Modifications of the Antibody

The antibody used in the methods or included in the articles of manufacture herein is optionally conjugated to a cytotoxic agent. For instance, the antibody may be conjugated to a drug as described in WO2004/032828.

Chemotherapeutic agents useful in the generation of such antibody-cytotoxic agent conjugates have been described above.

Conjugates of an antibody and one or more small molecule toxins, such as a calicheamicin, a maytansine (U.S. Pat. No. 5,208,020), a trichothene, and CC 1065 are also contemplated herein. In one embodiment of the invention, the antibody is conjugated to one or more maytansine molecules (e.g. about 1 to about 10 maytansine molecules per antibody molecule). Maytansine may, for example, be converted to May-SS-Me, which may be reduced to May-SH13 and reacted with modified antibody (Chari et al. *Cancer Research* 52: 127-131 (1992)) to generate a maytansinoid-antibody conjugate.

Alternatively, the antibody is conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^I$, $\alpha_2^I$, $\alpha_3^I$, N-acetyl-$\gamma_1^I$, PSAG and $\theta^I_1$ (Hinman et al. *Cancer Research* 53: 3336-3342 (1993) and Lode et al. *Cancer Research* 58: 2925-2928 (1998)).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates antibody conjugated with a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) that is conjugated to a cytotoxic agent (e.g. a radionucleotide).

The antibodies of the present invention may also be conjugated with a prodrug-activating enzyme that converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs: arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs: β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 (1984)).

Other modifications of the antibody are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. In some embodiments, the antibody fragments, such as Fab', are linked to one or more PEG molecules.

The antibodies disclosed herein may also be formulated as liposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

Amino acid sequence modification(s) of the antibody are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by different residue. The sites of greatest interest for substitutional mutagenesis of antibody antibodies include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in Table 2, may be introduced and the products screened.

TABLE 2

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln: Lys: Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |

TABLE 2-continued

| Original Residue | Exemplary Substitutions | Preferred Substitutions |
| --- | --- | --- |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)
Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg:
(5) residues that influence chain orientation: Gly, Pro;
(6) aromatic: Trp, Tyr. Phe.
Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant (s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is patiented to screening as described herein and antibodies with superior properties in one or more relevant assays may be selected for further development.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1 (Presta, L.); see also US 2004/0093621 A1 (Kyowa Hakko Kogyo Co., Ltd) concerning a CD20 antibody composition. Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087 (Patel et al.); see also WO98/58964 (Raju, S.) and WO99/22764 (Raju, S.) concerning antibodies with altered carbohydrate attached to the Fc region thereof.

In some embodiments, the glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US Pat. Appl. No. US 2003/0157108 A1, Presta, L; WO 00/61739A1; WO01/29246A1; US2003/0115614A1; US2002/0164328A1; US2004/0093621A1; US2004/0132140A1; US2004/0110704A1; US2004/0110282A1; US2004/0109865A1; WO03/085119A1; WO03/084570A1; WO2005/035778; WO2005/035586 (describing RNA inhibition (RNAi) of fucosylation); Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L: and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered that has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fe region thereof. In some embodiments, the antibody with improved ADCC comprises substitutions at positions 298, 333, and/or 334 of the Fc region. In some embodiments, the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogic et al.). The antibodies comprise an amino acid substitution at one or more of amino acid positions 270, 322, 326, 327, 329, 313, 333 and/or 334 of the Fe region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fe region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et al.).

VI. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides: proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA: sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations are described in WO98/56418. This publication describes a liquid multidose formulation comprising 40 mg/mL Rituximab, 25 mM acetate, 150 mM trehalose, 0.9% benzyl alcohol, 0.02% polysorbate 20 at pH 5.0 that has a minimum shelf life of two years storage at 2-8BC. Another anti-CD20 formulation of interest comprises 10 mg/mL Rituximab in 9.0 mg/mL sodium chloride, 7.35 mg/mL sodium citrate dihydrate, 0.7 mg/mL polysorbate 80, and Sterile Water for Injection, pH 6.5.

Lyophilized formulations adapted for subcutaneous administration are described in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystallized forms of the antibody or antibody are also contemplated. See, for example, US 2002/0136719A1 (Shenoy et al.).

The formulation herein may also contain more than one active compound as necessary for the particular indication being treated, in some embodiments, those with complementary activities that do not adversely affect each other. For example, it may be desirable to further provide a cytotoxic agent; chemotherapeutic agent; immunosuppressive agent; cytokine; cytokine antagonist or antibody; growth factor; hormone; integrin: integrin antagonist or antibody (e.g. an LFA-1 antibody such as efalizumab/RAPTIVA commercially available from Genentech, or an alpha 4 integrin antibody such as natalizumab/TYSABRI® available from Biogen Idec/Elan Pharmaceuticals, Inc.); interferon class drug such as IFN-beta-1a (REBIF® and AVONEX®) or IFN-beta-1b (BETASERON®); an oligopeptide such a glatiramer acetate (COPAXONE®); a cytotoxic agent such as mitoxantrone (NOVANTRONE®), methotrexate, cyclophosphamide, chlorambucil, or azathioprine; intravenous immunoglobulin (gamma globulin): lymphocyte-depleting drug (e.g., mitoxantrone, cyclophosphamide, Campath, anti-CD4, or cladribine); non-lymphocyte-depleting immunosuppressive drug (e.g., mycophenolate mofetil (MMF) or cyclosporine); cholesterol-lowering drug of the "statin" class; estradiol; testosterone: hormone replacement therapy; drug that treats symptoms secondary or related to MS (e.g., spasticity, incontinence, pain, fatigue): a TNF inhibitor; disease-modifying anti-rheumatic drug (DMARD); non-steroidal anti-inflammatory drug (NSAID); corticosteroid (e.g. methylprednisolone, prednisone, dexamethasone, or glucorticoid): levothyroxine; cyclosporin A; somatastatin analogue; cytokine antagonist; anti-metabolite: immunosuppressive agent; integrin antagonist or antibody (e.g. an LFA-1 antibody, such as efalizumab or an alpha 4 integrin antibody such as natalizumab); or another B-cell surface antagonist/antibody; etc in the formulation. The type and effective amounts of such other agents depend, for example, on the amount of antibody present in the formulation, the type of multiple sclerosis being treated, and clinical parameters of the patients. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

In some embodiments, the formulation comprises one or more of the group consisting of a histidine buffer, trehalose, sucrose, and polysorbate 20. In some embodiments, the histidine buffer is a histidine-acetate buffer, pH 6.0. Examples of formulations suitable for the administration of the anti-CD20 antibody are found in Andya et al., US2006/0088523, which is incorporated by reference in its entirety with respect to formulations.

Exemplary anti-CD20 antibody formulations are described in Andya et al., US2006/0088523 and WO98/56418, which are incorporated by reference in its entirety. In some embodiments, formulation is a liquid multidose formulation comprising the anti-CD20 antibody at 40 mg/mL, 25 mM acetate, 150 mM trehalose, 0.9% benzyl alcohol, 0.02% polysorbate 20 at pH 5.0 that has a minimum shelf life of two years storage at 2-8° C. In some embodiments, anti-CD20 formulation of interest comprises 10 mg/mL antibody in 9.0 mg/mL sodium chloride, 7.35 mg/mL sodium citrate dihydrate, 0.7 mg/mL polysorbate 80, and Sterile Water for Injection, pH 6.5. In some embodiments, the anti-CD20 antibody is in an aqueous pharmaceutical formulation comprising 10-30 mM sodium acetate from about pH 4.8 to about pH 5.5, preferably at pH5.5, polysorbate as a surfactant in a an amount of about 0.01-0.1% v/v, trehalose at an amount of about 2-10% w/v, and benzyl alcohol as a preservative (U.S. Pat. No. 6,171,586, which is incorporated by reference in its entirety). Lyophilized formulations adapted for subcutaneous administration are described in WO97/04801, which is incorporated by reference in its entirety. Such lyophilized formulations may be reconstituted with a suitable diluent to a high protein concentration and the reconstituted formulation may be administered subcutaneously to the mammal to be treated herein.

In some embodiments, the humanized 2H7 variants formulation is antibody at 12-14 mg/mL in 10 mM histidine, 6% sucrose, 0.02% polysorbate 20, pH 5.8. In a specific embodiment, 2H117 variants and in particular 2H7.v16 is formulated at 20 mg/mL antibody in 10 mM histidine sulfate, 60 mg/ml sucrose, 0.2 mg/ml polysorbate 20, and Sterile Water for Injection, at pH5.8. In a specific embodiment, one IV formulation of humanized 2H7 v16 is: 30 mg/ml antibody in 20 mM sodium acetate, 4% trehalose dihydrate, 0.02% polysorbate 20 (Tween 20™), pH 5.3. In some embodiments, the humanized 2H7.v511 variant formulation is 15-30 mg/ml antibody, preferably 20 mg/mL antibody, in 10 mM histidine sulfate, 60 mg/ml sucrose (6%), 0.2 mg/ml polysorbate 20 (0.02%), and Sterile Water for Injection, at pH 5.8. In yet another embodiment, the formulation for 2H7 variants and in particular 2H7.v511 is 20 mg/ml 2H7, 20 mM sodium acetate, 4% trehalose dihydrate, 0.02% polysorbate 20, pH 5.5, for intravenous administration. In some embodiments, 2H117.v 114 formulation is antibody at 15-25 mg/ml, preferably 20 mg/ml, in 20 mM Sodium Acetate, 240 mM (8%) trehalose dihydrate, 0.02% Polysorbate 20, pH 5.3.

VII. Articles of Manufacture and Methods of Manufacture

The invention provides articles of manufacture comprising: (a) a container comprising ocrelizumab; and (b) a package insert with instructions for treating multiple sclerosis in a patient, wherein the instructions denote (i.e., indicate) that an amount of ocrelizumab is administered to the patient that is effective to provide an initial ocrelizumab exposure of between about 0.3 to about 0.6 grams followed by a second ocrelizumab exposure of between about 0.3 to about 0.6 grams, the second exposure not being administered until from about 16 to 60 weeks from the initial exposure, and each of the ocrelizumab exposures is provided to the patient as one or two doses of ocrelizumab. In some embodiments, the initial ocrelizumab exposure is about 0.6 grams. In some embodiments, the second ocrelizumab exposure is about 0.6 grams. In some embodiments, the second exposure is administered from about 24 weeks from the initial exposure. In some embodiments, one or more of the ocrelizumab exposures are provided to the patient as one dose of ocrelizumab. In some embodiments, one or more of the ocrelizumab exposures are provided to the patient as two doses of ocrelizumab. In some embodiments, the two doses of ocrelizumab comprise about 0.3 grams of ocrelizumab.

The invention further provides articles of manufacture containing materials useful for the treatment of progressive multiple sclerosis described herein. In some embodiments, the article of manufacture comprising, packaged together, a pharmaceutical composition comprising an anti-CD20 antibody and a pharmaceutically acceptable carrier and a label denoting that the anti-CD20 antibody or pharmaceutical composition is indicated for treating patients with multiple sclerosis having one or more characteristics selected from the group consisting of (a) an age less than about 55 years, (b) one or more gadolinium staining lesions, (c) at least about a one point increase in Expanded Disability Status Scale (EDSS) over two years prior to starting the treatment, and (d) a Multiple Sclerosis Severity Score (MSSS) greater than about 5 points.

In some embodiments, the article of manufacture comprising, packaged together, a pharmaceutical composition comprising an anti-CD20 antibody and a pharmaceutically acceptable carrier and a label denoting that administration of the anti-CD20 antibody or pharmaceutical composition is based upon the patient having one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments, the article of manufacture comprising, packaged together, a pharmaceutical composition comprising an anti-CD20 antibody and a pharmaceutically acceptable carrier and a label denoting that the pharmaceutical composition is administered to a selected patient, wherein the selected patient has one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the articles of manufacture described herein, the patients have one or more characteristics selected from the group consisting of (a) an age less than about 55 years, (b) one or more gadolinium staining lesions, and (c) at least about a one point increase in Expanded Disability Status Scale (EDSS) over two years prior to starting treatment.

In some embodiments of any of the articles of manufacture described herein, the patient has more than one characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments of any of the articles of manufacture described herein, the patient has two characteristics selected from the group consisting of (a) an age less than about 55 years, (b) one or more gadolinium staining lesions, and (c) at least about a one point increase in EDSS over two years prior to starting treatment. In some embodiments, the patient has three characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the articles of manufacture, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments of any of the articles of manufacture, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments of any of the articles of manufacture, the increase in EDSS over two years prior to starting treatment is not attributable to relapse. In some embodiments, the patient has had an EDSS of greater than about 5.0 for less than about 15 years. In some embodiments, the patient has had an EDSS less than or equal to about 5.0 for less than about 10 years. In some embodiments, the EDSS when starting treatment is between about 3.0 and about 6.5. In some embodiments, the increase in EDSS is at least about a 1.5 point increase in EDSS over two years prior to starting treatment. In some embodiments, the 1.5 point increase in EDSS over two years prior to starting treatment is not attributable to relapse. In some embodiments, the patient further had two or more relapses within two years prior to starting treatment.

In some embodiments of any of the articles of manufacture described herein, the patient and/or patient population is characterized by having an MSSS of greater than about any of 6, 7, 8, or 9. In some embodiments of any of the articles of manufacture, the patient and/or patient population is characterized by having an MSSS of greater than about 9.

In some embodiments of any of the articles of manufacture, the age of the patient is less than about 51.

In some embodiments of any of the articles of manufacture, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments of any of the articles of manufacture, the anti-CD20 antibody comprises: a) a heavy chain variable region comprising SEQ ID NO: 10, SEQ ID NO: 11, and SEQ ID NO:12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The article of manufacture comprises a container and a label or package insert on or associated with the container. Suitable containers include, for example, bottles, vials, syringes, etc. The containers may be formed from a variety of materials such as glass or plastic. The container holds or contains a composition that is effective for treating the multiple sclerosis and may have a sterile access port (for example the container may be an intravenous solution bag or a vial having a stopper pierceable by a hypodermic injection needle). At least one active agent in the composition is the antibody. In some embodiments, the container comprises between about 0.3 to about 4.0 grams of the anti-CD20 antibody. In some embodiments, the container comprises between about 0.3 to about 1.5 grams of the anti-CD20 antibody.

The label or package insert indicates that the composition is used for treating multiple sclerosis in a patient suffering therefrom with specific guidance regarding dosing amounts and intervals of antibody and any other drug being provided. The article of manufacture may further comprise a second container comprising a pharmaceutically acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Optionally, the article of manufacture herein further comprises a container comprising an agent other than the antibody for treatment and further comprising instructions on treating the patient with such agent, such agent preferably being a chemotherapeutic agent or immunosuppressive agent, interferon class drug such as IFN-beta-1a (REBIF® and AVONEX®) or IFN-beta-1b (BETASERON®): an oligopeptide such a glatiramer acetate (COPAXONE®); a cytotoxic agent such as mitoxantrone (NOVANTRONE®), methotrexate, cyclophosphamide, chlorambucil, or azathioprine; intravenous immunoglobulin (gamma globulin); lymphocyte-depleting drug (e.g., mitoxantrone, cyclophosphamide, Campath, anti-CD4, or cladribine); non-lymphocyte-depleting immunosuppressive drug (e.g., mycophenolate mofetil (MMF) or cyclosporine); cholesterol-lowering drug of the "statin" class: estradiol; hormone replacement therapy; drug that treats symptoms secondary or related to MS (e.g., spasticity, incontinence, pain, fatigue); a TNF inhibitor; disease-modifying anti-rheumatic drug (DMARD); non-steroidal anti-inflammatory drug (NSAID); corticosteroid (e.g. methylprednisolone, prednisone, dexamethasone, or glucorticoid); levothyroxine; cyclosporin A; somatastatin analogue; cytokine or cytokine receptor antagonist; anti-metabolite; immunosuppressive agent; integrin antagonist or antibody (e.g. an LFA-1 antibody, such as efalizumab or an alpha 4 integrin antibody such as natalizumab); and another B-cell surface marker antibody; etc.

In some embodiments, the label may further denote any of the embodiments described herein. For example, the label may denote that the patient has (a) an age less than about 55 years and (b) one or more gadolinium staining lesions.

In another embodiment of the invention, a method for manufacturing containing materials useful for the treatment of progressive multiple sclerosis described herein is provided. In some embodiments, the method for manufacturing an anti-CD20 antibody or a pharmaceutical composition thereof comprising combining in a package the anti-CD20 antibody or pharmaceutical composition and a label denoting that the anti-CD20 antibody or pharmaceutical composition is indicated for treating patients with progressive multiple sclerosis, wherein the patients have one or more characteristics selected from the group consisting of (a) an age less than about 55 years. (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the methods of manufacturing described herein, the patients have one or more characteristics selected from the group consisting of (a) an age less than about 55 years, (b) one or more gadolinium staining lesions, and (c) at least about a one point increase in Expanded Disability Status Scale (EDSS) over two years prior to starting treatment.

VIII. Methods of Advertising and Marketing

The present invention also provides methods for advertising an anti-CD20 antibody or a pharmaceutically acceptable composition thereof comprising promoting, to a target audience, the use of the anti-CD20 antibody or pharmaceutical composition thereof for treating a patient or patient population with progressive multiple sclerosis, wherein the patient or patient population has one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

Provided herein are also methods for marketing an anti-CD20 antibody or a pharmaceutically acceptable composition thereof for use in a progressive multiple sclerosis patient subpopulation, the method comprising informing a target audience about the use of the anti-CD20 antibody for treating the patient subpopulation characterized by the patients of such subpopulation having one or more characteristics selected from the group consisting of (a) an age less than about 55 years. (b) one or more gadolinium staining lesions. (c) at least about a one point increase in Expanded Disability Status Scale (EDSS) over two years prior to starting treatment, and (d) a Multiple Sclerosis Severity Score (MSSS) greater than about 5 points.

In addition, the invention provides methods of specifying an anti-CD20 antibody for use in a progressive multiple sclerosis patient subpopulation, the method comprising providing instruction to administer the anti-CD20 antibody or a pharmaceutically acceptable composition thereof to the patient subpopulation characterized by the subpopulation has one or more characteristics selected from the group consisting of (a) an age less than about 55 years. (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

The invention further provides methods of providing a treatment option for patients with progressive multiple sclerosis comprising packaging an anti-CD20 antibody in a vial with a package insert containing instructions to treat patients with progressive multiple sclerosis, wherein the patients have one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the methods, the patients have one or more characteristics selected from the group consisting of (a) an age less than about 55 years, (b) one or more gadolinium staining lesions, and (c) at least about a one point increase in Expanded Disability Status Scale (EDSS) over two years prior to starting treatment.

In some embodiments of any of the methods, the patient has two characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has three characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the methods, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments of any of the methods, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments of any of the methods, the increase in EDSS over two years prior to starting treatment is not attributable to relapse. In some embodiments, the patient has had an EDSS of greater than about 5.0 for less than about 15 years. In some embodiments, the patient has had an EDSS less than or equal to about 5.0 for less than about 10 years. In some embodiments, the EDSS when starting treatment is between about 3.0 and about 6.5. In some embodiments, the increase in EDSS is at least about a 1.5 point increase in EDSS over two years prior to starting treatment. In some embodiments, the 1.5 point increase in EDSS over two years prior to starting treatment is not attributable to relapse. In some embodiments, the patient further had two or more relapses within two years prior to starting treatment.

In some embodiments of any of the methods, the age of the patient is less than about 51.

In some embodiments of any of the methods, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments of any of the methods, the anti-CD20 antibody is ocrelizumab. In some embodiments of any of the methods, the anti-CD20 antibody is rituximab. In some embodiments of any of the methods, the anti-CD20 antibody is ofatumumab. In some embodiments of any of the methods, the anti-CD20 antibody is TRU-015 or SBI-087. In some embodiments of any of the methods, the anti-CD20 antibody is GA101. In some embodiments of any of the methods, the anti-CD20 antibody is hA20.

The methods described herein may encompass any combination of the embodiments described herein. For example, the methods include methods, wherein the patient (a) an age less than about 55 years and (b) one or more gadolinium staining lesions.

IX. Systems and Methods for Predicting Responsiveness to Multiple Sclerosis Treatment The invention also provides systems and methods for analyzing whether a subject and/or patient with progressive multiple sclerosis will respond to a treatment with a drug used to treat multiple sclerosis. The invention provides systems for analyzing responsiveness of a patient with progressive multiple sclerosis to treatment with a drug used to treat multiple sclerosis comprising: (a) assessing one or more characteristics selected from the group consisting of (i) an age less than about 55 years, (ii) one or more gadolinium staining lesions, (iii) at least about a one point increase in Expanded Disability Status Scale (EDSS) over two years prior to starting treatment, and (iv) a Multiple Sclerosis Severity Score (MSSS) greater than about 5 points; (b) hardware to perform the assessment of (a); and (c) computational means to perform an algorithm to determine if the patient is susceptible or responsive to said treatment.

The invention further provides methods for predicting whether a subject with progressive multiple sclerosis will respond to a treatment with a drug used to treat multiple sclerosis, the methods comprising assessing one or more characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points, whereby the age, the gadolinium staining lesions, the increase in EDDS over two years prior to starting the treatment, MSSS, or a combination thereof indicates that the subject will respond to the treatment.

In some embodiments of any of the systems and/or methods, the patient has more than one characteristics selected from the group consisting of (a) an age less than about 55 years, (b) one or more gadolinium staining lesions, and (c) at least about a one point increase in Expanded Disability Status Scale (EDSS) over two years prior to starting treatment.

In some embodiments of any of the systems and/or methods described herein, the patient has more than one characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments of any of the systems and/or methods, the patient has two characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has three characteristics selected from the group consisting of (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points. In some embodiments, the patient has (a) an age less than about 55 years, (b) one or more gadolinium staining lesions, (c) at least about a one point increase in Expanded Disability Status Scale (EDSS) over two years prior to starting treatment, and (d) a Multiple Sclerosis Severity Score (MSSS) greater than about 5 points.

In some embodiments of any of the systems and/or methods, the progressive multiple sclerosis is primary progressive multiple sclerosis. In some embodiments, the progressive multiple sclerosis is secondary progressive multiple sclerosis. In some embodiments, the progressive multiple sclerosis is progressive relapsing multiple sclerosis. In some embodiments, the patient is not diagnosed with relapsing remitting multiple sclerosis when starting treatment.

In some embodiments of any of the systems or methods, the patient further has evidence of inflammation in a sample. In some embodiments, the sample is a cerebrospinal fluid sample. In some embodiments, the evidence of inflammation is indicated by an elevated IgG index. In some embodiments, the evidence of inflammation is indicated by IgG oligoclonal bands detected by isoelectric focusing.

In some embodiments of any of the systems and/or methods, the increase in EDSS over two years prior to starting treatment is not attributable to relapse. In some embodiments, the patient has had an EDSS of greater than about 5.0 for less than about 15 years. In some embodiments, the patient has had an EDSS less than or equal to about 5.0 for less than about 10 years. In some embodiments, the EDSS when starting treatment is between about 3.0 and about 6.5. In some embodiments, the increase in EDSS is at least about a 1.5 point increase in EDSS over two years prior to starting treatment. In some embodiments, the 1.5 point increase in EDSS over two years prior to starting treatment is not attributable to relapse. In some embodiments, the patient further had two or more relapses within two years prior to starting treatment.

In some embodiments of any of the systems and/or methods, the age of the patient is less than about 51.

In some embodiments of any of the systems and/or methods, the systems or methods further comprises advising the patient.

In some embodiments of any of the systems and/or methods, the treatment reduces the time to confirmed disease progression. In some embodiments, the confirmed disease progression is an increase in EDSS that is sustained for twelve weeks. In some embodiments, the confirmed disease progression is an increase in EDSS that is sustained for twenty-four weeks.

In some embodiments of any of the systems and/or methods, the drug is a Interferon beta-1b (e.g., Betaseron®), Interferon beta-1a (e.g., Avonex® or Rebif®), Glatiramer (e.g., Copaxone®), Mitoxantrone (e.g., Novantrone), corticosteroids (e.g., ethylprednisolone, prednisone, dexamethasone), 3-4 diaminopyridine, ABT-874, Alemtuzumab, Albuterol (Proventil®), ATL1102, Atorvastatin (Lipitor®), Azathioprine, BG00012 (dimethyl fumarate), BHT-3009, Botulinum toxin A (Botox®), C-105, cannador, dronabinol, tetrahydrocannabinol, cannabidiol, CDP323, Cladribine, CNTO 1275, Cyclophosphamide, Daclizumab, Dextromethorphan/quinidine (AVP-923, Zenvia™), Donepezil (Aricept®), Doxycycline, Estradiol, Estriol, Estroprogestins, Fampridine-SR (4-aminopyridine, sustained release), Fingolimod (FTY720). Interferon tau, lamotrigine (Lamictal®), Laquinimod, Lidocaine+prilocaine (EMLA), MBP8298 (synthetic myelin basic protein peptide), Memantine (Namenda®), Methylprednisolone, MN-166, Modafinil (Provigil®), Mycophenolate mofetil (Cellcept®), naltrexone, Natalizumab (Tysabri®), Paroxetine (Paxil®), PL-2301 (copolymer), Pioglitazone (Actos®), Pixantrone (BBR 2778), Pravastatin (Pravachol®), Pregabalin (Lyrica®), Progesterone, RG2077, Riluzole (Rilutek®), Rolipram (phosphodiesterase-4 inhibitor), RTL1000, SB-683699, Simvastatin (Zocor®), T cell receptor peptide vaccine (NeuroVax™), Teriflunomide, Testosterone gel (Androgel®), or Trimethoprim.

In some embodiments of any of the systems and/or methods, the drug used to treat multiple sclerosis is an anti-CD20 antibody. In some embodiments, the anti-CD20 antibody comprises: a) a heavy chain variable region comprising SEQ ID NO: 10, SEQ ID NO: 11, and SEQ ID NO: 12, and b) a light chain variable region comprising SEQ ID NO:4, SEQ ID NO:5, and SEQ ID NO:6. In some embodiments, the anti-CD20 antibody is ocrelizumab. In some embodiments, the anti-CD20 antibody is rituximab. In some embodiments, the anti-CD20 antibody is ofatumumab. In some embodiments, the anti-CD20 antibody is TRU-015 or SBI-087. In some embodiments, the anti-CD20 antibody is GA101. In some embodiments, the anti-CD20 antibody is hA20.

The systems and/or methods described herein may encompass any combination of the embodiments described herein. For example, the methods include methods, wherein the patient (a) an age less than about 55 years and (b) one or more gadolinium staining lesions.

Further details of the invention are illustrated by the following non-limiting Examples. The disclosures of all citations in the specification are expressly incorporated herein by reference.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

Example 1: A Phase II Study of Ocrelizumab in Relapsing-Remitting Multiple Sclerosis (RRMS)

A phase II, multicenter, randomized, parallel-group, partially blinded, placebo and Avonex controlled dose finding study to evaluate the efficacy as measured by brain Magnetic Resonance Imaging (MRI) lesions, and safety of two dose regimens of ocrelizumab in patients with Relapsing-Remitting Multiple Sclerosis (RRMS) is performed.

The two ocrelizumab dose regimens under investigation are as follows: 1) ocrelizumab 1000 mg dose regimen: consisting of a dual infusion of 1000 mg for the first treatment cycle followed by single infusions of 1000 mg for the subsequent treatment cycles and 2) ocrelizumab 600 mg dose regimen: consisting of a dual infusion of 300 mg for the first treatment cycle followed by single infusions of 600 mg for the subsequent treatment cycles.

Eligible patients are randomized (1:1:1:1) into one of four treatment groups A, B, C or D as described in FIG. 7. The overview of the study design is illustrated in FIG. 7.

Group A (ocrelizumab 1000 mg): Two intravenous (i.v.) infusions of ocrelizumab each of 1000 mg separated by 14 days for the 1st treatment cycle. Patients then receive the maintenance dose regimen, i.e., a single infusion of 1000 mg for every subsequent 24-week treatment cycle. Subsequently, in order to maintain the study double-blind during the 2nd treatment cycle, patients receive two infusions separated by 14 days, the first infusion is ocrelizumab 1000 mg and the second infusion placebo. In the 3rd and 4th treatment cycles, patients are treated with a single 1000 mg infusion, without a second placebo infusion, in a double-blind manner until a preferred dose is chosen on the basis of the primary analysis.

Group B (ocrelizumab 600 mg): Two i.v. infusions of ocrelizumab each of 300 mg separated by 14 days for the 1st treatment cycle. Patients then receive the maintenance dose regimen, i.e., a single infusion of 600 mg for every subsequent 24-week treatment cycle. Subsequently, in order to maintain the study double-blind during the 2nd treatment cycle, patients receive two infusions separated by 14 days, the first infusion is ocrelizumab 600 mg and the second infusion placebo. In the 3rd and 4th treatment cycles, patients are treated with a single 600 mg infusion, without a second placebo infusion in a double-blind manner until a preferred dose is chosen on the basis of the primary analysis.

Group C (placebo): Two i.v. infusions of placebo separated by 14 days for the 1st treatment cycle. Thereafter, patients are placed on the 600 mg dose regimen of ocrelizumab starting with two double-blind i.v. infusions of ocrelizumab 300 mg separated by 14 days at the start of the 2nd treatment cycle. Patients then receive the maintenance dose regimen, i.e., a single infusion of 600 mg administered in a double-blind manner for the 3rd and 4th treatment cycles, until a preferred dose is chosen on the basis of the primary analysis.

Group D (Avonex): Avonex 30 µg intra-muscular (i.m.) weekly for the 1st treatment cycle. Thereafter, patients are offered, on a voluntary and open label basis, the 600 mg dose regimen of ocrelizumab starting with two i.v. infusions of ocrelizumab 300 mg separated by 14 days at the start of the 2nd treatment cycle. Patients in the 3rd and 4th treatment cycles are treated with a single 600 mg infusion until a preferred dose is chosen on the basis of the primary analysis.

For all groups, after investigators and ethics committees are informed of the preferred dose, patients receive the preferred dose (600 mg or 1000 mg) as a single infusion at their next successive treatment cycle(s).

The first administration of study medication whether an i.v. infusion (ocrelizumab or placebo) or the first i.m. injection of Avonex will define the start of the Treatment Period (Day 1). All patients also receive an i.v. infusion of methylprednisolone 100 mg on study day 1 and with each subsequent ocrelizumab or placebo infusion or, for patients receiving Avonex (Group D) according to the time points required for the ocrelizumab infusions.

There are four treatment cycles, i.e. cycle 1=Baseline to Week 24; cycle 2=Week 24 to Week 48; cycle 3=Week 48 to Week 72; cycle 4=Week 72 to Week 96. After the 1st cycle infusion visits (Visits 2 and 3, Day 1 and Week 2, respectively), visits occur at Week 4 and every 4 weeks thereafter for the first 24 weeks. After the 2nd cycle infusion visits (Visits 9 and 10, Week 24 and 26, respectively), visits occur at Week 36 and every 12 weeks thereafter through the end of the Treatment and Follow-up Periods. All effort should be made to schedule the visits within the provided windows. Additional unscheduled visits for the assessment of potential relapses, new neurological symptoms or safety events may occur at any time.

Study Population and Selection Criteria

Men and women from 18 to 55 years of age inclusive, who are diagnosed with relapsing-remitting multiple sclerosis (RRMS) in accordance with the revised McDonald criteria (2005) and who meet the inclusion/exclusion criteria provided below are eligible for enrollment into the study.

Inclusion Criteria:

Patients must meet the following criteria to be eligible for study entry:

1. RRMS in accordance with the revised McDonald criteria (2005);
2. Ages 18-55 years inclusive;
3. At least two documented relapses within the last 3 years prior to screening, at least one of which occurred within the last year prior to screening;
4. Expanded Disability Status Scale (EDSS) at baseline from 1.0 to 6.0 points;

5. Evidence of Multiple Sclerosis (MS) disease burden as defined below:
   a. At least six T2 lesions on an MRI scan done in the year prior to screening, based on local reading. Should an MRI scan be unavailable within the last year or showing less than six T2 lesions, a screening MRI scan with at least six T2 lesions is required for the patient to be eligible, OR
   b. Patient had 2 documented relapses within the year prior to screening.

Exclusion Criteria

Patients who meet the following criteria will be excluded from study entry:

1. Secondary or primary progressive multiple sclerosis at screening (Visit 1);
2. Disease duration of more than 15 years in patients with an EDSS ≤2.0.

Efficacy Analysis

The primary objective in this study is to investigate the effect of ocrelizumab given as two dose regimens of 600 or 1000 mg intravenously (see FIG. 7) on the total number of gadolinium-enhancing T1 lesions observed on MRI scans of the brain at weeks 12, 16, 20 and 24 as compared with placebo.

The secondary objectives of this study are to evaluate the efficacy and safety of ocrelizumab compared with placebo, as reflected by the following: the annualized protocol defined relapse rate by Week 24; proportion of patients who remain relapse-free by Week 24 (protocol defined relapses); the total number of gadolinium-enhancing T1 lesions observed on MRI scans of the brain at Weeks 4, 8, 12, 16, 20 and 24; the total number of new and/or persisting gadolinium-enhancing T1 lesions on MRI scans of the brain at Weeks 4, 8, 12, 16, 20 and 24; change in total volume of T2 lesions on MRI scans of the brain from baseline to Week 24, to evaluate the safety and tolerability of two dose regimens of ocrelizumab in patients with RRMS as compared with placebo and Avonex at Week 24 and the overall safety of ocrelizumab administered for up to 96 weeks, and to investigate the pharmacokinetics and other pharmacodynamic study endpoints of ocrelizumab.

In this Example, a relapse is defined as the occurrence of new or worsening neurological symptoms attributable to MS and immediately preceded by a relatively stable or improving neurological state of at least 30 days. Symptoms must persist for >24 hours and should not be attributable to confounding clinical factors (e.g., fever, infection, injury, adverse reactions to concomitant medications). The new or worsening neurological symptoms must be accompanied by objective neurological worsening consistent with an increase of at least half a step on the EDSS, or 2 points on one of the appropriate Functional System Scores (FSS), or 1 point on two or more of the appropriate FSS. The change must affect the selected FSS (i.e., pyramidal, gait, cerebellar, brainstem, sensory, or visual). Sensory changes, episodic spasms, fatigue, mood change or bladder or bowel urgency or incontinence do not suffice to establish a relapse. The examining investigator confirms those relapses that adhere to the above criteria.

The exploratory objectives in this study will include, but may not be limited to: change in brain volume on MRI scans of the brain from the baseline scan to Week 12; change in brain volume on MRI scans of the brain from Week 12 to Week 96 in a subgroup of patients receiving ocrelizumab; the total number of new and/or enlarging T2 lesions observed on MRI scans of the brain at Weeks 4, 8, 12, 16, 20 and 24; the proportion of patients who remain free of new gadolinium-enhancing T1 lesions by Week 24; time to first new gadolinium-enhancing T1 lesions developing over 24 weeks; to evaluate the treatment withdrawal effect by means of the total number of gadolinium-enhancing T1 lesions 48 weeks after receiving up to 4 treatment cycles of ocrelizumab in a subgroup of patients; proportion of patients who remain free from relapses (clinical and protocol-defined relapses) during each treatment cycle and at Weeks 48 and 96; proportion of patients requiring systemic methylprednisolone treatment for an MS relapse during each treatment cycle and at Weeks 48 and 96; annualized clinical and protocol-defined relapse rate during each treatment cycle and at Weeks 48 and 96; time to first protocol-defined relapse by Week 24; time to first protocol-defined relapse by Week 96; time to onset of sustained disability progression as defined by the sustained worsening in EDSS of 1.0 point or more for 12 weeks through Week 96; time to onset of sustained disability progression as defined by the sustained worsening in EDSS of 1.0 point or more for 24 weeks through Week 96; to explore the effects of ocrelizumab on the primary and secondary study endpoints vs. Avonex; to explore the correlation of polymorphic variants in genes associated with RRMS susceptibility and ocrelizumab activity and therapeutic response to ocrelizumab in RRMS patients; to explore the relationship between circulating biomarkers associated with RRMS susceptibility and ocrelizumab activity and therapeutic response to ocrelizumab treatment in RRMS patients; change in the Modified Fatigue Impact Scale (MFIS) from baseline to Weeks 24 and 48; change in the Fatigue Scale for Motor and Cognitive Functions (FSMC) from baseline to Weeks 24 and 48; change in the proportion of patients who moved from "severe" to "moderate" and from "moderate" to "mild" fatigue on the FSMC, comparing baseline to Weeks 24 and 48; change in the Center for Epidemiological Studies-Depression Scale (CES-D) from baseline to Weeks 24 and 48; and change in the proportion of patients who moved from a state of greater depressive symptomatology to a state of less depressive symptomatology on the CES-D, comparing baseline to Weeks 24 and 48.

Brain MRI

MRI is a useful tool for monitoring central nervous system (CNS) lesions in MS. Brain MRI scans are only obtained at screening in some patients (see Secondary Endpoints) and in all patients at baseline and at four-week intervals between baseline and week 24. In addition, in a subgroup of patients (Groups A and B), a brain MRI scan is performed at weeks 96 (Visit 16) and 48 weeks later, i.e., week 144.

The MRI includes the acquisition of the following scans at each time point: T2-weighted MRI scan, T1-weighted MRI scan (without gadolinium-enhancement), and T1-weighted MRI scan (with gadolinium-enhancement).

Assessment of Disability

Disability progression as measured by EDSS is assessed in all patients by the independent examining investigator at screening and every 12 weeks throughout the study until the Observation Period at which time disability progression is assessed after 24 weeks.

Disability progression is defined as an increase of ≥1.0 point from the baseline EDSS score that is not attributable to another etiology (e.g. fever, concurrent illness, or concomitant medication) when the baseline score is 5.0 or less, and ≥0.5 when the baseline score is 5.5 or more. Disease progression is considered sustained when the increase in the EDSS is confirmed at a regularly scheduled visit at least 12 weeks after the initial documentation of the progression. An alternative definition of sustained disability progression requires that the increase in EDSS be confirmed at least 24 weeks after the initial documentation of the progression.

The EDSS is based on a standard neurological examination; the seven categories of the EDSS representing functional systems (pyramidal, cerebellar, brainstem, sensory, bowel and bladder, visual, and cerebral and/or mental, plus "other") are rated and scored (collectively, functional system scores or FSS). Each score of the FSS is an ordinal clinical rating scale ranging from 0 to 5 or 6. These ratings are then used in conjunction with observations and information concerning ambulation and use of assistive devices to determine the EDSS score. The EDSS is a disability scale that ranges in 0.5-point steps from 0 (normal) to 10 (death).

Example 2: A Phase II/III Study of Rituximab in Primary Progressive Multiple Sclerosis (PPMS)

A randomized, double-blind, parallel group, placebo controlled, multicenter Phase II/II study (U2786g) to evaluate the safety and efficacy of rituximab in adults with Primary Progressive Multiple Sclerosis (PPMS) as defined by McDonald et al (Ann Neurol 50:121-7 (2001)) was performed.

Subjects were randomized in a 2:1 ratio to receive either rituximab or placebo. Rituximab, commercially available from Genentech, was formulated for i.v. administration as a sterile product in 9.0 mg/ml sodium chloride, 0.7 mg/ml polysorbate 80, 7.35 mg/ml sodium citrate dehydrate, and sterile water for injection (pH 6.5). Each course of study drug consisted of two i.v. infusions (separated by 14 days) of 1000 mg rituximab or placebo. Subjects received the first course of treatment at Days 1 and 15 and received additional courses at Weeks 24, 48, and 72. Subjects received acetaminophen (1 g) and diphenhydramine HCl (50 mg), or equivalent, by mouth 30-60 min prior to start of each infusion. Glucocorticoids were not administered prior to infusion. In 96 weeks of trial duration, subjects were seen at regularly scheduled visits for physical examinations, neurologic and MRI assessments, to collect adverse events and vital signs, and to complete routine hematology, serum chemistries, and urinalysis lab tests.

Baseline demographics of Intent-To-Treat (ITT) subjects are presented in Table 3.

TABLE 3

Demographic and Baseline Characteristics: Intent-to-Treat Subjects.

| Characteristic | Placebo (n = 147) | Rituximab (n = 292) | All Subjects (n = 439) |
|---|---|---|---|
| Age (yr) | | | |
| n | 147 | 292 | 439 |
| Mean (SD) | 49.6 (8.69) | 50.1 (9.02) | 49.9 (8.90) |
| Median | 51.0 | 51.0 | 51.0 |
| Minimum to maximum | 20-66 | 18-66 | 18-66 |
| 18-<40 | 20 (13.6%) | 40 (13.7%) | 60 (13.7%) |
| 40-<55 | 80 (54.4%) | 145 (49.7%) | 225 (51.3%) |
| ≥55 | 47 (32.0%) | 107 (36.6%) | 154 (35.1%) |

MS disease duration was similar in both treatment groups. Baseline MRI results are summarized in Table 4. The baseline MRI characteristics were similar in placebo and rituximab groups.

TABLE 4

Baseline MRI Results: Intent-to-Treat Subjects.

| MRI Endpoint | Placebo (N = 147) | Rituximab (N = 292) | All Subjects (N = 439) |
|---|---|---|---|
| Total gadolinium-enhancing lesion count | 2 | | |
| N | 147 | 290 | 437 |
| Mean (SD) | 0.5 (1.26) | 0.7 (2.96) | 0.7 (2.52) |
| Median | 0.0 | 0.0 | 0.0 |
| Minimum to maximum | 0-8 | 0-32 | 0-32 |
| 0 | 110 (74.8%) | 220 (75.9%) | 330 (75.5%) |
| 1 | 23 (15.6%) | 44 (15.2%) | 67 (15.3%) |
| 2 | 5 (3.4%) | 10 (3.4%) | 15 (3.4%) |
| 3 | 5 (3.4%) | 5 (1.7%) | 10 (2.3%) |
| ≥4 | 4 (2.7%) | 11 (3.8%) | 15 (3.4%) |
| Total gadolinium-enhancing lesion volume (mm$^3$) | | | |
| N | 147 | 290 | 437 |
| Mean (SD) | 27.56 (81.86) | 49.50 (220.32) | 42.12 (185.82) |
| Median | 0.00 | 0.00 | 0.00 |
| Minimum to maximum | 0.00-556.40 | 0.00-2660.00 | 0.00-2660.00 |
| T2 lesion volume (mm$^3$) | | | |
| N | 147 | 290 | 437 |
| Mean (SD) | 8850.86 (11808.95) | 9336.66 (13744.94) | 9173.25 (13113.98) |
| Median | 5199.50 | 5240.50 | 5220.70 |
| Minimum to maximum | 73.83-74534.0 | 174.00-155303.0 | 73.83-155303.0 |
| Brain volume (cc) | | | |
| N | 130 | 237 | 367 |
| Mean (SD) | 1210.91 (128.89) | 1202.92 (120.23) | 1205.75 (123.25) |
| Median | 1209.5 | 1204.0 | 1207.0 |
| Minimum to maximum | 642.0-1522.0 | 712.60-1508.0 | 642.0-1522.0 |

MRI = magnetic resonance imaging.

Randomization was stratified according to study site; baseline disease severity defined by EDSS (≤4.0, >4.0). Baseline EDSS is summarized in Table 5. As a result of the dynamic randomization, the percentage of subjects in each treatment group was similar at all levels of the stratification factors.

TABLE 5

Baseline Stratification Factors, Disease Severity Intent-to-Treat Subjects.

| Stratification Factor | Placebo (n = 147) | Rituximab (n = 292) | All Subjects (n = 439) |
|---|---|---|---|
| EDSS | | | |
| N | 147 | 292 | 439 |
| 2 | 6 (4.1%) | 8 (2.7%) | 14 (3.2%) |
| 2.5 | 5 (3.4%) | 11 (3.8%) | 16 (3.6%) |
| 3 | 11 (7.5%) | 22 (7.5%) | 33 (7.5%) |
| 3.5 | 21 (14.3%) | 36 (12.3%) | 57 (13.0%) |
| 4 | 25 (17.0%) | 47 (16.1%) | 72 (16.4%) |
| 4.5 | 8 (5.4%) | 19 (6.5%) | 27 (6.2%) |
| 5 | 6 (4.1%) | 10 (3.4%) | 16 (3.6%) |
| 5.5 | 10 (6.8%) | 10 (3.4%) | 20 (4.6%) |
| 6 | 28 (19.0%) | 81 (27.7%) | 109 (24.8%) |
| 6.5 | 27 (18.4%) | 48 (16.4%) | 75 (17.1%) |
| Mean (SD) | 4.73 (1.395) | 4.84 (1.369) | 4.80 (1.377) |
| Median | 4.50 | 5.00 | 5.00 |
| Minimum to maximum | 2.0-6.5 | 2.0-6.5 | 2.0-6.5 |

EDSS = Expanded Disability Status Scale.

Additionally, the two treatment groups were similar in other baseline disease severity measures: EDSS, Kurtzke Functional System Scores, the Multiple Sclerosis Functional Composite Scale (MSFCS) score and the MSFCS components (Timed 25-Foot Walk, 9-Hole Peg Test, and PASAT-3).

Efficacy Results

The primary efficacy analysis for this trial compared the time to confirmed disease progression, during the 96 week treatment period, between rituximab and placebo. Disease progression is defined as an increase of ≥1.0 point from baseline EDSS (Kurtzke J. Neurology 33(11):1444-52 (1983)), if the baseline EDSS is between 2.0 and 5.5 points (inclusive), or an increase of ≥0.5 point if the baseline EDSS is >5.5 points, for which change is not attributable to another etiology (e.g., fever, concurrent illness, MS relapse or exacerbation, or concomitant medication).

Stratified analysis showed that rituximab did not significantly delay the confirmed disease progression compared with placebo (p=0.1442, stratified log-rank). The percentage of patients progressing by 96 weeks was estimated to be 38.5% and 30.2% for the placebo and rituximab groups, respectively (Table 6). Kaplan-Meier plots for the time to confirmed disease progression are shown in the FIG. 8.

TABLE 6

The Time to Confirmed Disease Progression during Treatment Period Intent-to-Treat Subjects.

| | Placebo (n = 147) | Rituximab (n = 292) |
|---|---|---|
| No. of subjects who had CDP (%) | 53 (36.1%) | 83 (28.4%) |
| No. of subjects who censored (%) | 94 (63.9%) | 209 (71.6%) |
| Stratified p-value | | |
| Log-rank test | | 0.1442 |
| Stratified hazard ratio (rel to placebo) | | 0.773 |
| 95% CI for | | (0.546-1.093) |
| Proportion of subjects with CDP | | |
| at week 24 | 6.9% | 9.1% |
| at week 48 | 19.3% | 20.2% |
| at week 72 | 30.3% | 28.0% |
| at week 96 | 38.5% | 30.2% |

Secondary efficacy endpoints included change from baseline to Week 96 in the total volume of T2 lesions and change from baseline to Week 96 in the brain volume. A Hochberg-Bonferroni procedure was used to control the type I error rate in testing these two secondary endpoints. The change from baseline to Week 96 in the brain volume was not significantly different in the two treatment groups (p=0.6237). See Table 7.

TABLE 7

Change in Brain Volume from Baseline to Week 96.

| | Placebo (N = 130) | Rituximab (N = 237) | P-value |
|---|---|---|---|
| Volume at baseline (cm3) | | | |
| mean (SD) | 1211 (129) | 1203 (120) | |
| median | 1209.5 | 1204.0 | |
| Volume change from baseline to week 96 (LOCF) | | | |
| mean (SD) | −9.9 (37.0) | −10.8 (40.3) | 0.62 |
| median | −14.0 | −13.1 | |

A significant difference was observed between the two treatments for the change in T2 lesion volume from baseline to week 96 (p=0.0008). The median increase in volume of the T2 lesion was 809.50 mm$^3$ and 301.95 mm$^3$ in the placebo and rituximab groups, respectively. (See Table 8 and FIG. 9).

TABLE 8

Change from Baseline to Week 96 in the Total Volume of T2 Lesions on Brain MRI Scans Intent-to-Treat Subjects

| | Placebo (n = 147) | Rituximab (n = 292) | p-Value |
|---|---|---|---|
| Total volume of T2 lesions on brain MRI scan (mm3) | | | |
| Baseline | | | |
| N | 147 | 290 | |
| Mean(SD) | 8850.86 (11808.95) | 9336.66 (13744.94) | |
| Median | 5199.50 | 5240.50 | |
| Range | 73.83-74534.00 | 174.00-155303.0 | |

TABLE 8-continued

Change from Baseline to Week 96 in the Total Volume of
T2 Lesions on Brain MRI Scans Intent-to-Treat Subjects

|  | Placebo (n = 147) | Rituximab (n = 292) | p-Value |
|---|---|---|---|
| SE | 973.99 | 807.13 | |
| 95% CI | (6925.93-10775.79) | (7748.06-10925.26) | |
| Week 96 | | | |
| N | 147 | 290 | |
| Mean(SD) | 11055.55 (14536.29) | 10843.80 (15827.44) | |
| Median | 5526.60 | 5569.35 | |
| Range | 94.92-86232.00 | 179.30-170464.0 | |
| SE | 1198.93 | 929.42 | |
| 95% CI | (8686.04-13425.05) | (9014.51-12673.09) | |
| Change from baseline to week 96 | | | |
| N | 147 | 290 | |
| Mean(SD) | 2204.69 (4306.24) | 1507.14 (3739.45) | |
| Median | 809.50 | 301.95 | |
| Range | −8557.00-26367.00 | −4031.00-24076.00 | |
| SE | 355.17 | 219.59 | |
| 95% CI | (1502.74-2906.63) | (1074.94-1939.33) | |
| Treatment difference in LS means(vs. placebo) | | −718.24 | |
| 95% CI of the difference in LS means | | (−1504.48, 68.00) | |
| ANOVA t-test (stratified) | | | 0.0733 |
| Friedman ranked ANOVA test | | | 0.0008 |
| ANOVA t-test (stratified) on percent change from baseline to week 96 | | | 0.0006 |
| Friedman ranked ANOVA test on percent change from baseline to week 96 | | | 0.0005 |

Analyses of all exploratory endpoints except the change in T2 lesion volume, enlarging T2 lesion and new T2 lesion showed statistically non-significant differences between placebo and rituximab arms. Compared to placebo, the rituximab group experienced significantly less increase in T2 lesion volume at Week 48 and 122 (p=0.0051 and 0.0222, respectively); had less new T2 lesion at week 48 and 96 (p<0.001); had less enlarging T2 lesion count at week 48 and 96 (p=0.008 and 0.072, respectively).

Subgroup Analysis

Subgroup analysis for the primary endpoints included time to confirmed disease progression according to the following demographic and baseline disease characteristics: sites, age, gender, race, prior MS therapies, baseline EDSS, duration since MS symptom onset and baseline gadolinium (Gd) lesion, and baseline Multiple Sclerosis Severity Score (MSSS) (an index of how fast the patient progressed; see Roxburgh et al. *Neurology* 64; 1144-1151 (2005)).

Figure 10:
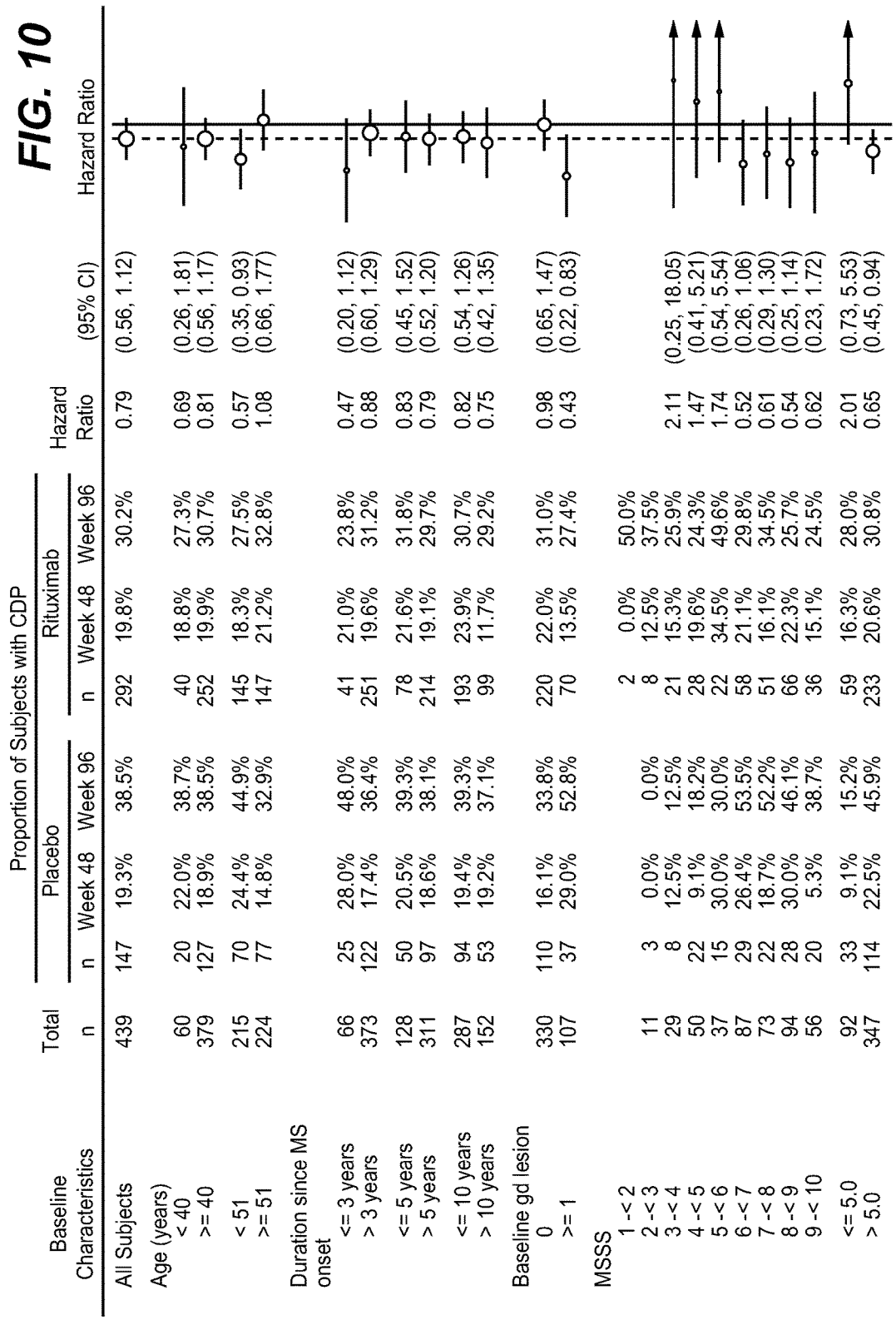
FIG. 10 shows a summary of baseline characteristics and hazard ratio of subjects in the placebo and rituximab groups.
Figure 11A:
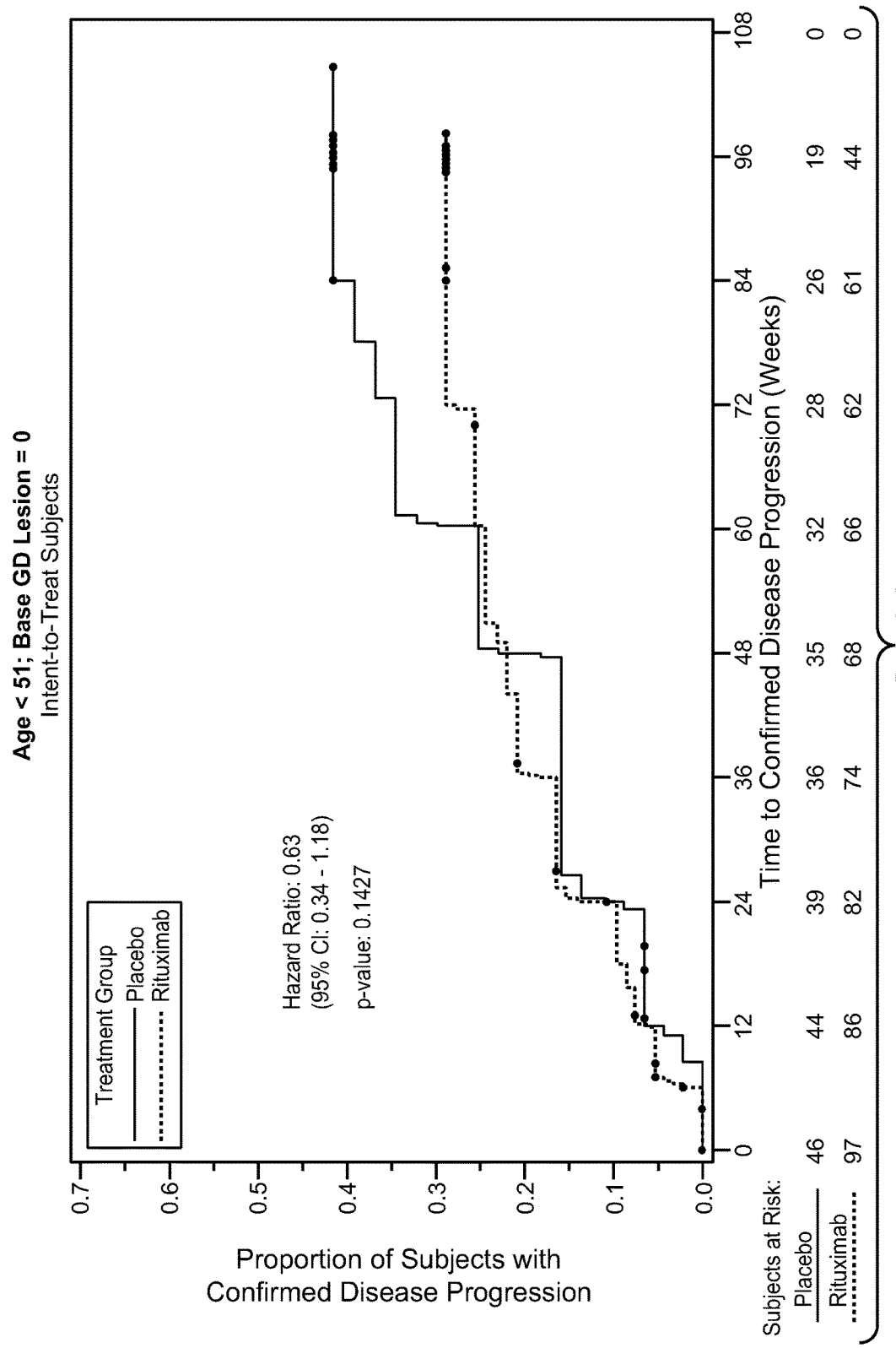
FIGS. 11A-11D show multivariate analysis of additive predictive effects of age and gadolinium (Gd) lesion at baseline for the treatment effect in the placebo and rituximab groups.
Figure 11B:
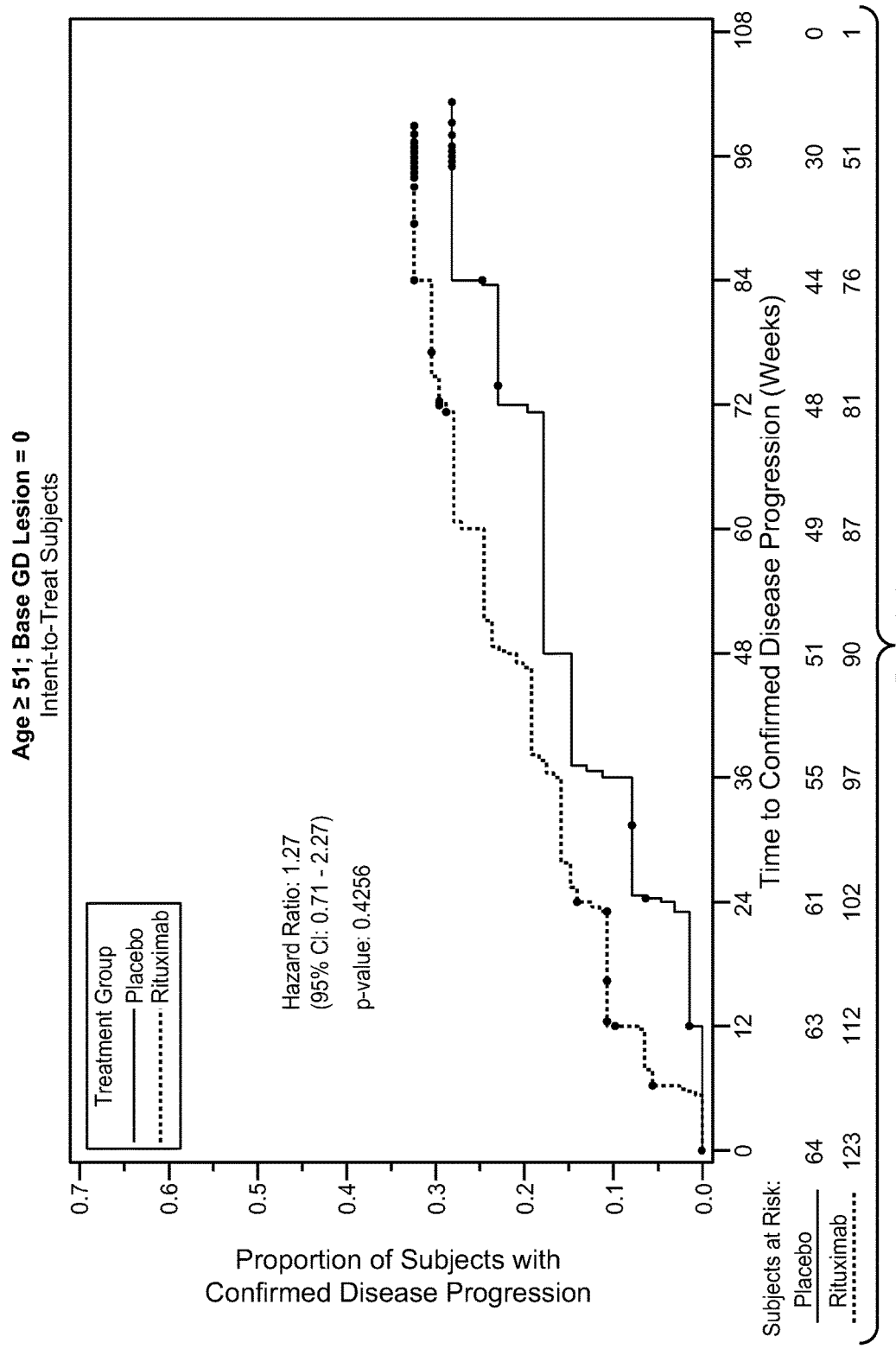
Figure 11C:
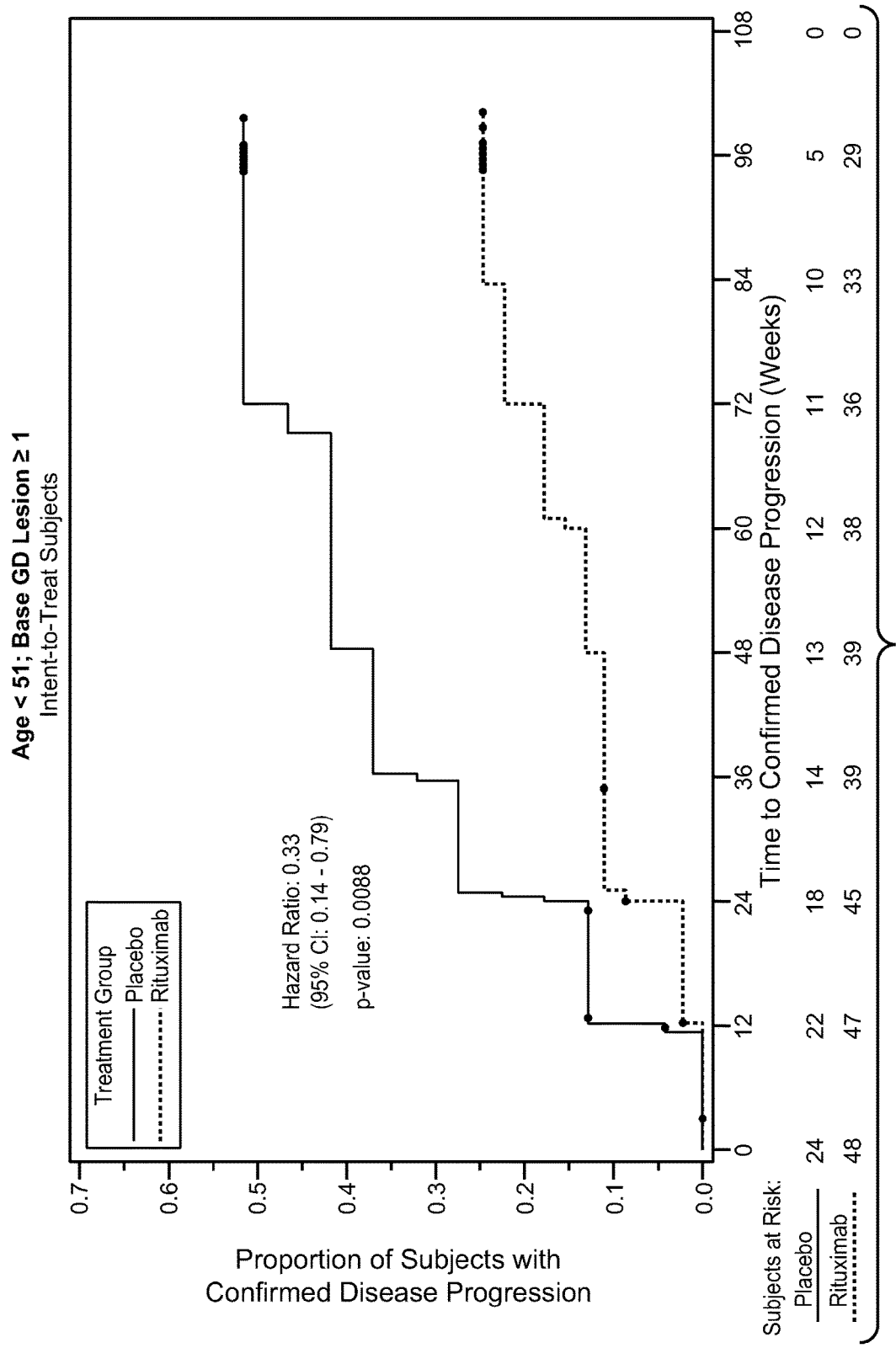
Figure 11D:
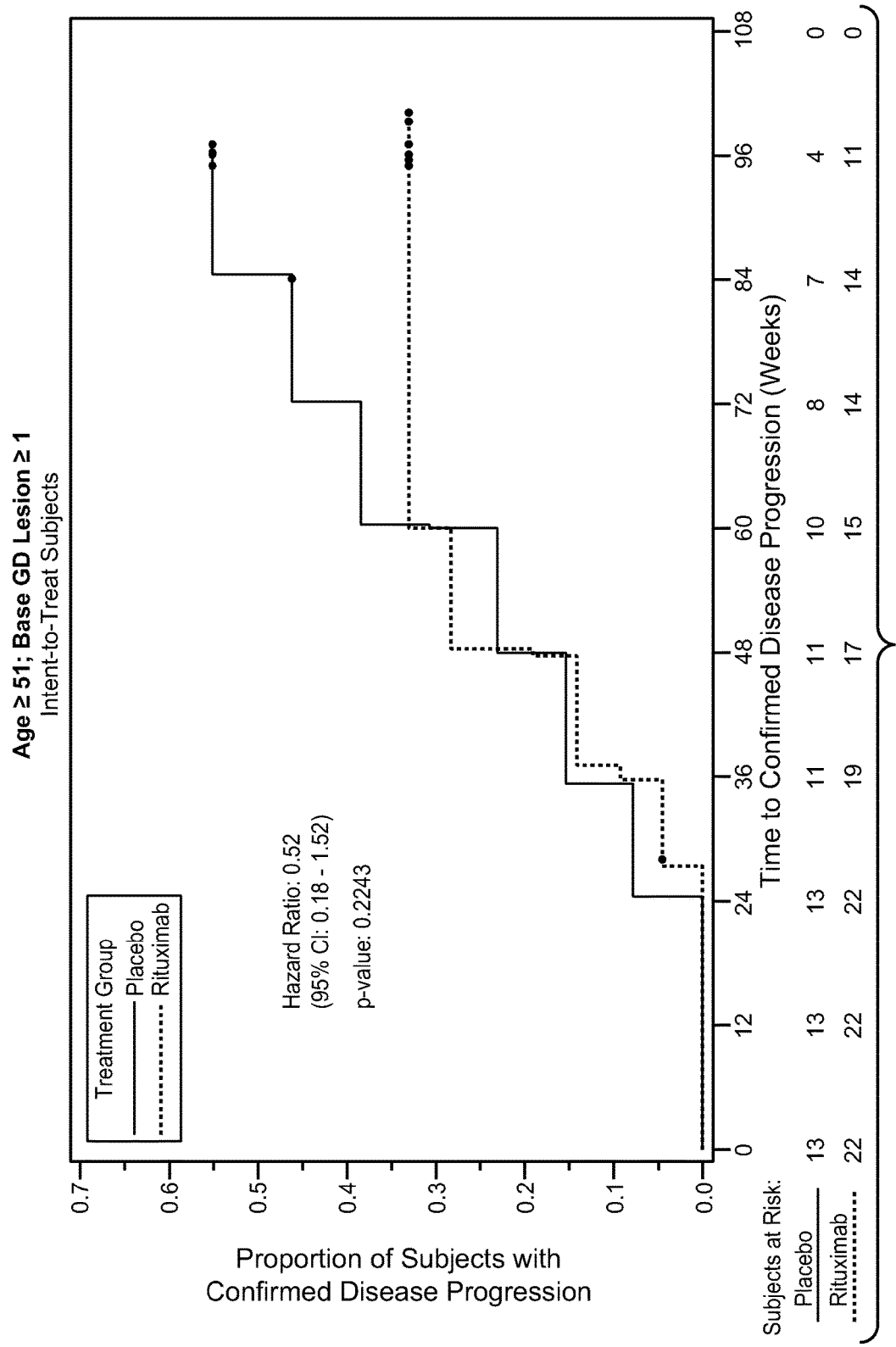
Figure 12A:
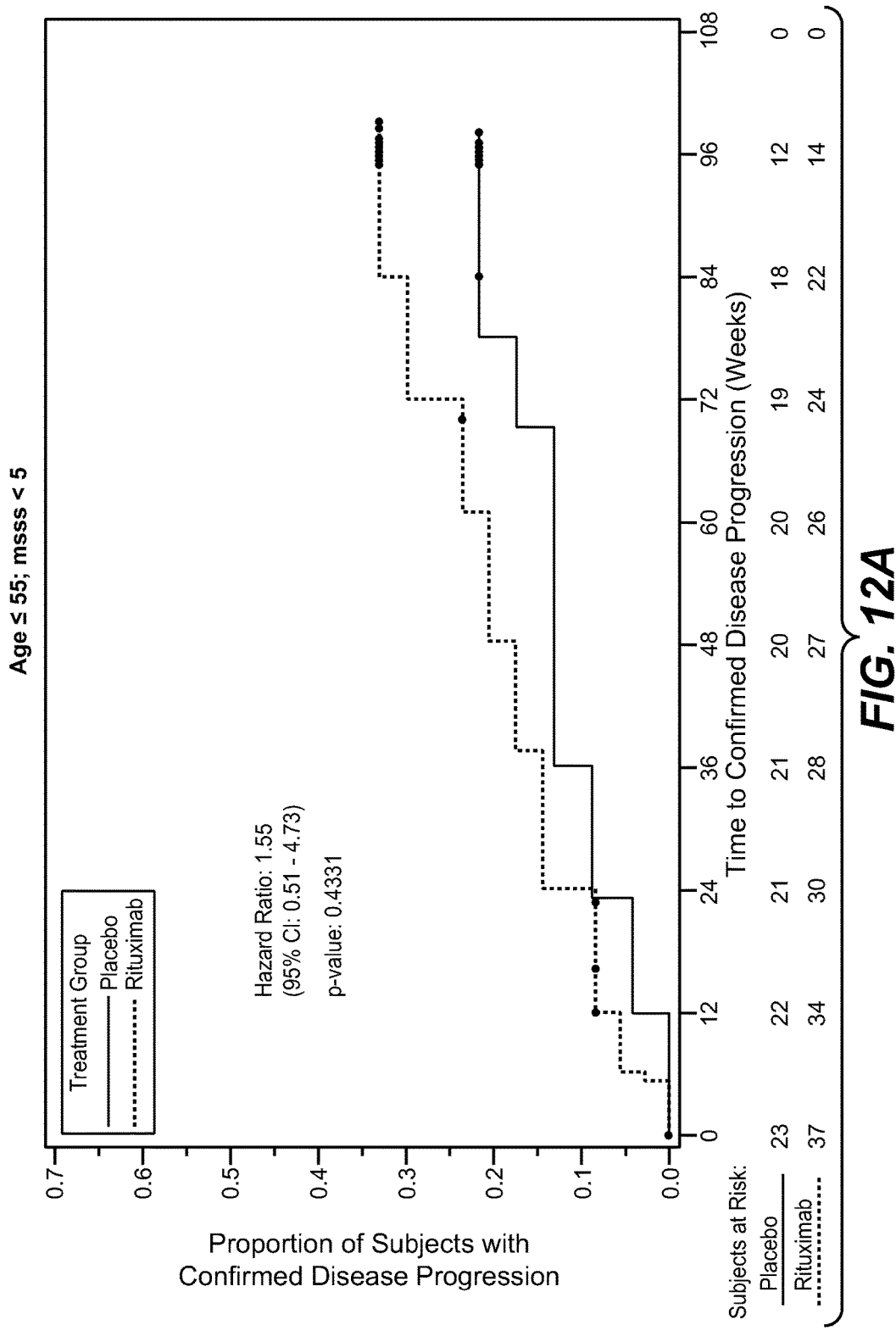
FIGS. 12A-12D show multivariate analysis of additive predictive effects of age and Multiple Sclerosis Severity Score (MSSS) for the treatment effect in the placebo and rituximab groups.
Figure 12B:
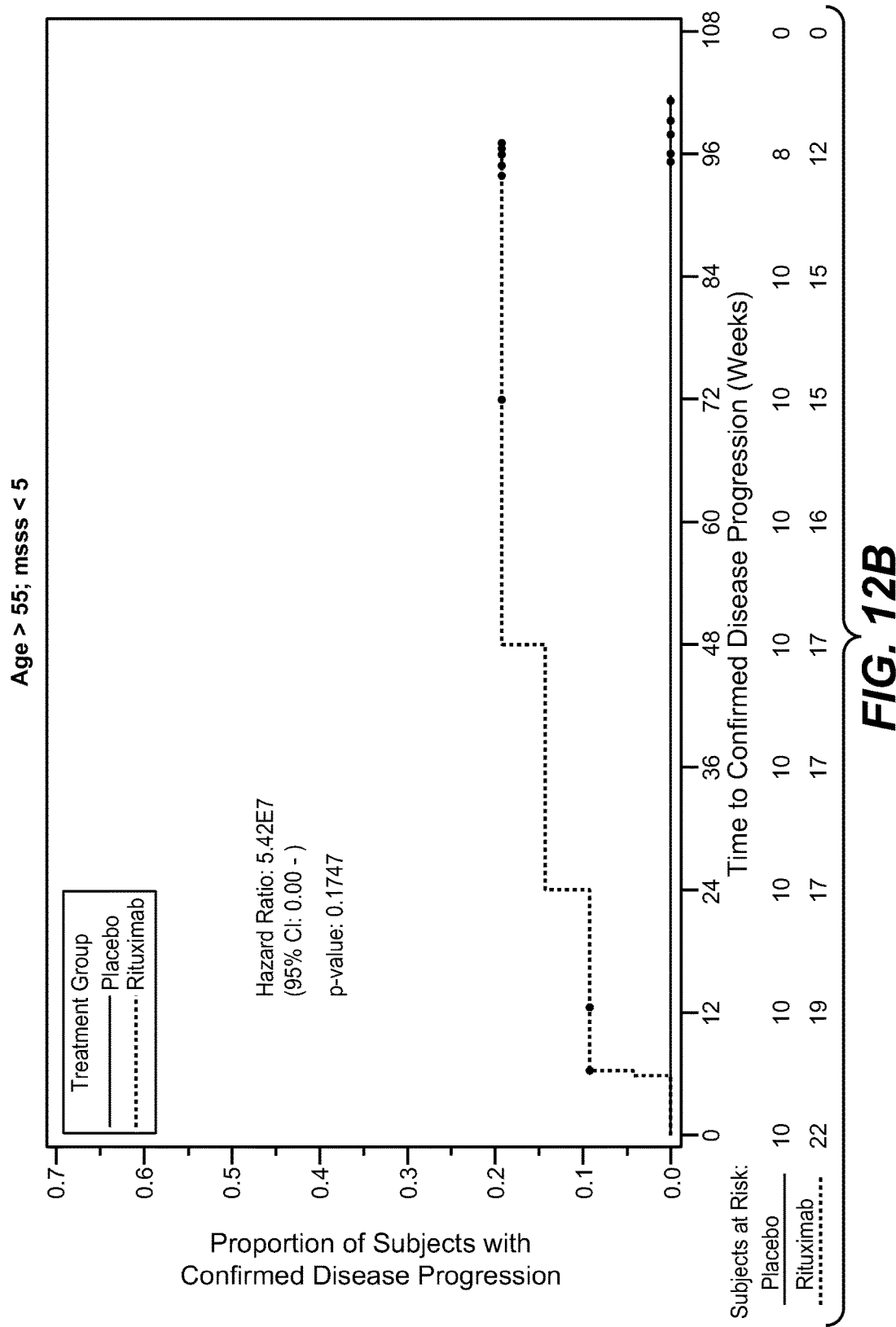
Figure 12C:
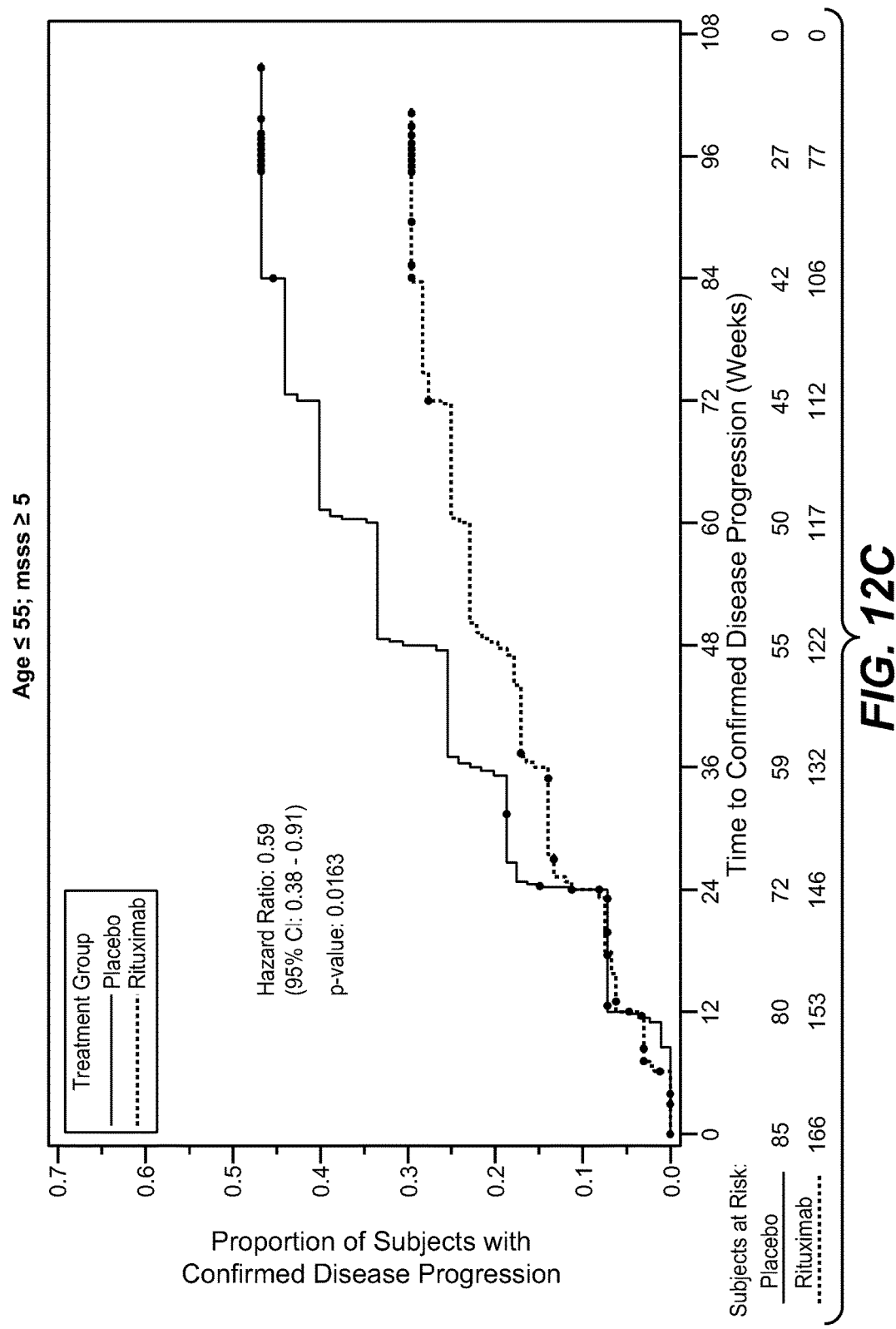
Figure 12D:
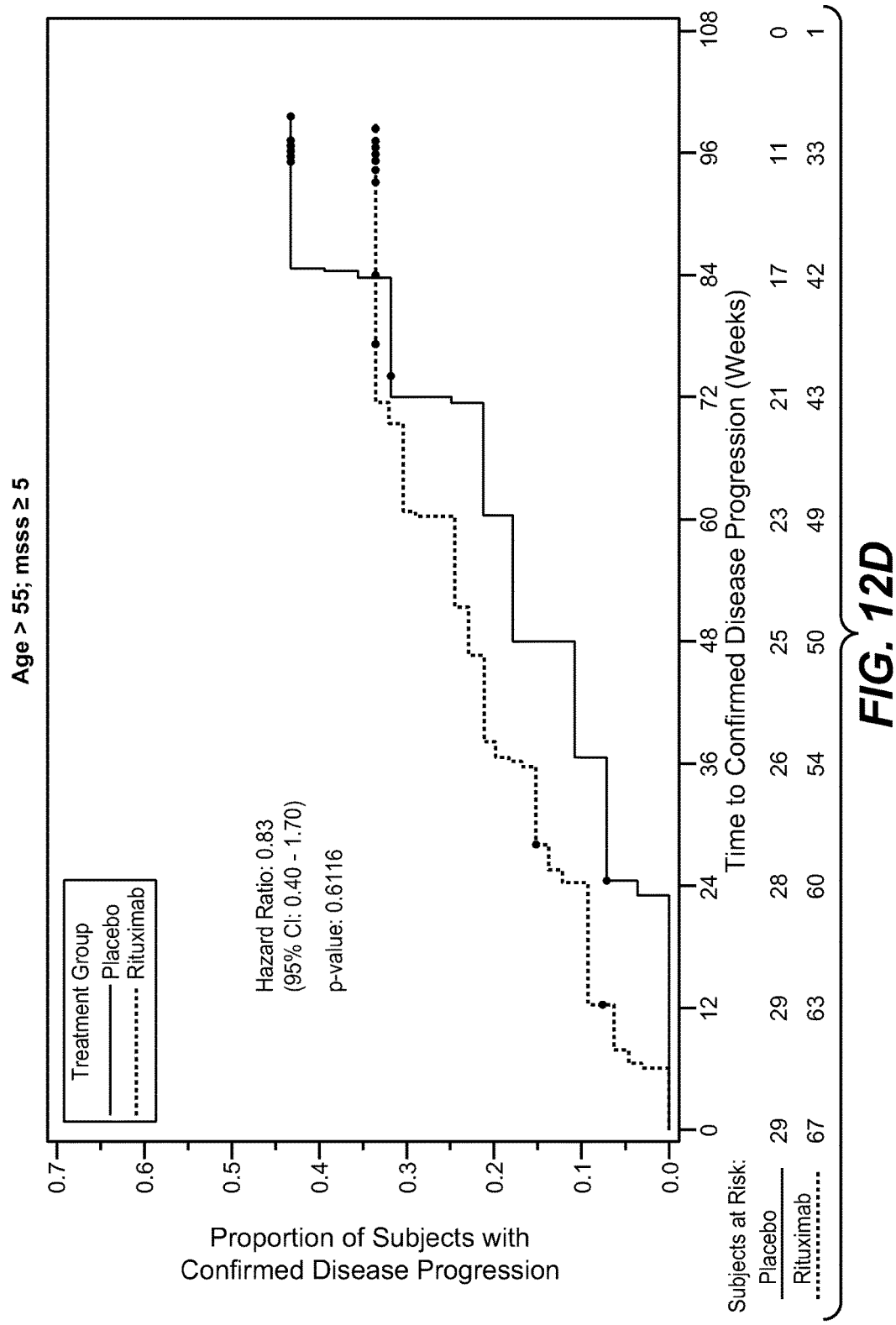
Figure 13:
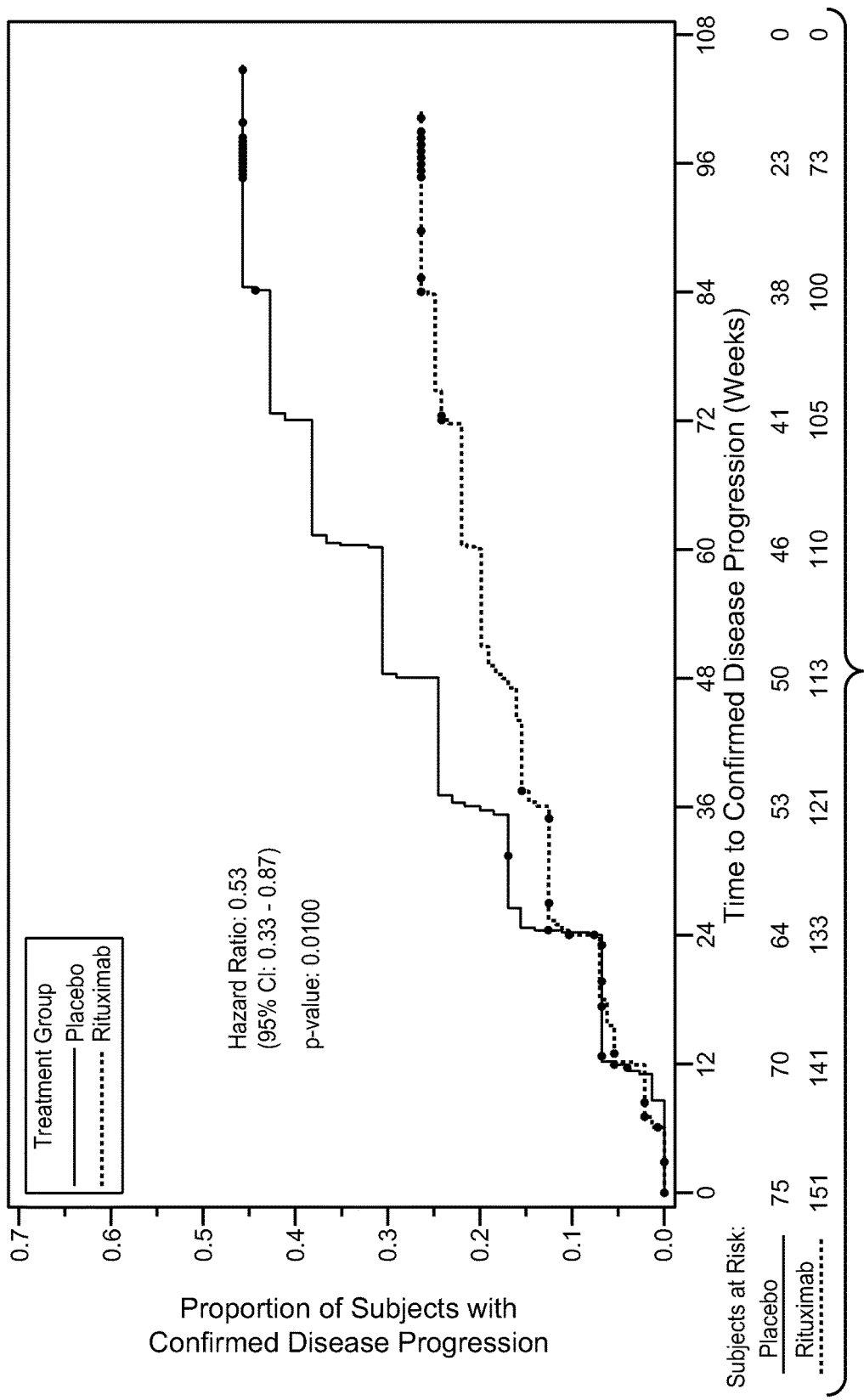
FIG. 13 shows Kaplan Meier plots for the time to confirmed disease progression of subjects in the placebo and rituximab groups with the following characteristics: age ≤55; 3≤baseline EDSS ≤6.5; excluding patients with disease duration >10 years if their baseline EDSS <5 or disease duration >15 if their baseline EDSS ≥5.

The subgroup analysis results suggest a potential treatment effect in patients who are younger, progressed more rapidly (higher MSSS) or with Gd lesions at baseline (FIG. 10). Moreover, additive predictive effects of age, Gd lesion at baseline and MSSS for the treatment effect have been verified using multivariate analysis method (FIG. 11 and FIG. 12). See also Table 9. Based on these findings with MSSS, a subgroup of the study population excluding older patients with longstanding disease and slow progression was selected using modified inclusion/exclusion criteria (age ≤55, 3≤baseline EDSS ≤6.5, excluding patients with disease duration >10 if their baseline EDSS <5 or disease duration >15 if their baseline EDSS ≥5). A significant treatment effect was also shown for this subgroup (stratified log-rank test P-value=0.01; FIG. 13).

TABLE 9

Time to Confirmed Disease Progression Subgroup Result Summary.

| Subgroups | Total N | CDP@wk 96 Placebo | CDP@wk96 Rituximab | HR | HR 95% CI | P-value (Log-rank) |
|---|---|---|---|---|---|---|
| All patients (Primary analysis) | 439 | 38.5% | 30.2% | n/a | n/a | 0.1442 |
| Age <51 | 215 | 44.9% | 27.5% | 0.52 | (0.32, 0.86) | 0.0101 |
| Gd+ | 107 | 52.8% | 27.4% | 0.41 | (0.21, 0.80) | 0.0069 |
| Gd+ and age <51 | 72 | 51.6% | 24.6% | 0.33 | (0.14, 0.79) | 0.0088 |
| Gd+ and age <55 | 93 | 49.5% | 29.1% | 0.40 | (0.19, 0.84) | 0.0126 |
| MSSS >=5 and age <55 | 251 | 46.8% | 29.6% | 0.59 | (0.38, 0.91) | .0163 |

Subgroup analyses suggest that PPMS patients with evidence of active disease show significant clinical signs of treatment related benefit as measured by time to confirmed disease progression, as well as change from baseline in EDSS, MSFC, and T2 lesions on brain MRI (data not shown). Independent factors that appeared prognostic of disease progression in the placebo group and potentially predictive of treatment response in the rituximab group included the following: younger age, particularly age less than 51; presence of contrast enhancing lesions at baseline on brain MRI; and higher MS severity score. These observations serve a hypothesis generating role supporting a potential therapeutic benefit of B-cell depletion on confirmed disease progression in appropriately selected progressive onset MS patients.

While this study failed to demonstrate primary efficacy in the overall PPMS population, subgroup efficacy analyses indicated that patients with contrast enhancing brain MRI lesions at baseline potentially responded to treatment with rituximab, with a 57% relative reduction in the hazard (1-HR) of confirmed disease progression in the treated group versus placebo, which is largely but not entirely driven by a very high placebo Confirmed Disease Progression (CDP) rate of 52.8% at 96 weeks (FIG. 10). PPMS patients aged less than 51 may also have benefited, with a 43% relative reduction in the hazard of confirmed disease progression and a placebo progression rate of 44.9%. While the presence of contrast enhancing lesions and age <51 were correlated, a post-hoc analysis of the 72 patients exhibiting both characteristics revealed a more pronounced apparent effect, with a 77% relative reduction in the hazard of confirmed disease progression (Table 9). In this subgroup the placebo progression rate of 51.6% was not higher than the rate for all patients with enhancing MRI lesions at baseline, but a lower rate of progression in the rituximab group (24.6%) accounts for the potentially greater risk reduction with treatment. These OLYMPUS placebo data corroborate natural history observations on the clinical and MRI heterogeneity of PPMS patients (Sastre-Garriga et al. *Neurology* 65(4):633-5 (2005), Ingle et al. *Brain* 126(Pt 11):2528-36 (2003), Tremlett et al. *Mult Scler.* 14(3):314-24 (2008), Tremlett et al. *Neurology* 65(12):1919-23 (2005), Kremenchutzky et al. *Brain* 129(Pt 3):584-94. (2006)). Furthermore, the MAG-NIMS clinical and MRI cohort study described a subset of PPMS patients with more inflammatory MRI activity early in the disease course and a worse prognosis for disability progression (Ingle et al. *J. Neurol Neurosurg Psychiatry* 76(9): 1255-8 (2005)); the OLYMPUS placebo data appear to confirm these observations for the first time.

Example 3: A Phase III Study of Ocrelizumab in Progressive Multiple Sclerosis

A Phase III, randomized, double-blind, parallel-group, multicenter study to evaluate the safety and efficacy of 600 mg of ocrelizumab as compared with placebo in adults with progressive MS is performed.

A total of 630 progressive MS patients (315 with progressive onset and 315 with relapsing onset MS) are enrolled and assigned (2:1 randomization) to either ocrelizumab arm or placebo arm stratified by site and type of multiple sclerosis. This study consists of the following three periods that apply to all patients: a screening period, a treatment period and a treatment free follow up period. In the first course of study drug treatment (300 mg ocrelizumab or placebo infusion×2) are administered on Days 1 and 15. In subsequent treatment courses, patients are dosed (600 mg ocrelizumab single infusion) every 24 weeks until the last patient enrolled receives his/her last course of treatment to be administered at Week 96.

Prior to each study drug infusion, patients receive treatment with an analgesic/antipyretic such as acetaminophen/paracetamol (1 grams) and an i.v. or oral antihistamine (such as diphenhydramine 50 mg), and 100 mg methylprednisolone intravenously, or equivalents, to reduce the incidence of potential infusion reactions. In patients with Common Terminology for Adverse Events (CTCAE) Grade 3 or higher (severe) infusion reactions with associated respiratory symptoms (stridor, wheeze or bronchospasm), additional treatment with bronchodilators may be indicated.

Routine laboratory studies are obtained throughout the study, with additional tests following courses of study drug treatment. Immune panel, serum human anti-human antibody (HAHA), and thyroid tests are also conducted. Serum samples of all patients are collected for pharmacokinetic analysis and blood samples are collected for B-cell count determination. B-cell counts are followed as a pharmacodynamic marker of ocrelizumab.

Patient Population and Selection Criteria

The target population for this study includes patients with progressive MS with or without a history of superimposed relapses. Patients with progressive MS eligible for this study are characterized by a diagnosis in accordance with the revised McDonald criteria (2005) and a period of 6 months or greater of documented irreversible loss of neurological function in the absence of relapses. Patients are selected with evidence of active disease and higher risk for more rapid disability progression, using criteria identified as potential risk factors in previous clinical trials with progressive MS patients. These factors include younger age, evidence of inflammation in the cerebrospinal fluid (CSF) (oligoclonal bands or elevated IgG index), contrast enhancing lesions on brain MRI, high relapse activity superimposed on non-relapse related progression, and more rapid historical accumulation of disability.

All patients volunteering and eligible for participation in the study are screened for conformance with the following inclusion and exclusion criteria:

Inclusion Criteria Include:
1. Diagnosis of Multiple Sclerosis in accordance with the revised McDonald criteria (2005).
2. Progressive MS, characterized by documented, irreversible loss of neurological function persisting for ≥6 months that cannot be attributed to clinical relapse.
3. Ages 18-55 years inclusive.
4. EDSS at screening from 3.0 to 6.5 points.
5. Score of ≥2.0 on the Functional Systems (FS) scale for the pyramidal system or gait that is due to lower extremity findings.
6. Presence of at least one of the following laboratory findings in a CSF specimen obtained during the screening period or documented within the previous 6 months as indicated by, for example, elevated IgG index and/or IgG oligoclonal bands detected by isoelectric focusing.
7. Presence of at least one of the following criteria:
  Age <50
  Gd+ lesions on brain MRI at screening or within 6 months of screening
  At least 1.5 point increase in EDSS over past 2 yrs not attributable to relapse
  Two relapses in past two years Exclusion Criteria Include:
1. Relapsing remitting multiple sclerosis at screening (Visit 1)
2. Disease duration from the onset of MS symptoms: more than 15 years in patients with an EDSS at screening >5.0 or more than 10 years in patients with an EDSS at screening ≤5.0.

Efficacy Analysis

The primary efficacy endpoint is the time to confirmed disease progression. Disease progression is defined as an increase of ≥1.0 point from baseline EDSS, if the baseline EDSS is between 2.0 and 5.5 points (inclusive), or an increase of ≥0.5 points, if the baseline EDSS is >5.5 points, for which change is not attributable to another etiology (e.g., fever, concurrent illness, MS relapse or exacerbation, or concomitant medication).

The EDSS is based on a standard neurological examination; the seven categories of the EDSS representing functional systems (pyramidal, cerebellar, brainstem, sensory, bowel and bladder, visual, and cerebral and/or mental, plus "other") are rated and scored (collectively, functional system scores or FSS). Each score of the FSS is an ordinal clinical rating scale ranging from 0 to 5 or 6. These ratings are then used in conjunction with observations and information concerning ambulation and use of assistive devices to determine the EDSS score. The EDSS is a disability scale that ranges in 0.5-point steps from 0 (normal) to 10 (death).

The secondary efficacy endpoints in support of the primary efficacy endpoint include: change from baseline to Week 120 in the total volume of T2 lesions on brain MRI scan, change from baseline to Week 120 in the 25-foot timed walk, time to confirmed disease progression, with confirmation occurring at least 24 weeks (≥168 days) after initial disease progression.

Assessment of Relapse

Patients are evaluated for relapses by the treating investigator at each visit throughout the study and, if necessary, at unscheduled visits to confirm relapses occurring between the visits. To meet the criteria for a protocol-defined relapse, the relapse is defined as the occurrence of new or worsening neurological symptoms attributable to MS and immediately preceded by a relatively stable or improving neurological state of least 30 days. Symptoms must persist for >24 hours and should not be attributable to confounding clinical factors (e.g., fever, infection, injury, adverse reactions to concomitant medications). The new or worsening neurological symptoms must be accompanied by objective neurological worsening consistent with an increase of at least half a step on the EDSS, or 2 points on one of the appropriate FSS, or 1 point on two or more of the appropriate FSS. The change must affect the selected FSS (i.e., pyramidal, ambulation, cerebellar, brainstem, sensory, or visual). Episodic spasms, sexual dysfunction, fatigue, mood change or bladder or bowel urgency or incontinence do not suffice to establish a relapse.

Brain MRI Imaging

Magnetic resonance imaging of the brain and cervical spinal cord are obtained at multiple time points during this study, including at baseline. The brain MRI includes the acquisition of the following scans at each time point: T2-weighted MRI scan and T1-weighted MRI scan (without gadolinium-enhancement).

Change from baseline to Week 120 in the total volume of T2 lesions and timed 25 foot walk are compared between ocrelizumab and placebo using ranked analysis of variance. The model includes the two stratification factors noted in the primary analysis.

Example 4: A Phase III Study of Ocrelizumab in Primary Progressive Multiple Sclerosis A Phase III, randomized, double-blind, parallel-group, multicenter study to evaluate the safety and efficacy of one of two dose regimens of ocrelizumab as compared with placebo in adults with primary progressive MS is performed. The two ocrelizumab dose regimens under investigation are as follows: 1) ocrelizumab 1000 mg dose regimen: consisting of a dual infusion of 1000 mg for the first treatment cycle followed by single infusions of 1000 mg for the subsequent treatment cycles and 2) ocrelizumab 600 mg dose regimen: consisting of a dual infusion of 300 mg for the first treatment cycle followed by single infusions of 600 mg for the subsequent treatment cycles.

A total of 630 primary progressive MS patients are enrolled and assigned (2:1 randomization) to either ocrelizumab arm or placebo arm stratified by site and type of multiple sclerosis. This study consists of the following three periods that apply to all patients: a screening period, a treatment period and a safety follow up period. In the first course of study drug treatment (ocrelizumab or placebo infusion×2) are administered on Days 1 and 15. In subsequent treatment courses, patients are dosed (ocrelizumab or placebo single infusion) every 24 weeks until the last patient enrolled receives his/her last course of treatment to be administered at Week 96.

Prior to each study drug infusion, patients receive treatment with an analgesic/antipyretic such as acetaminophen/paracetamol (1 grams) and an i.v. or oral antihistamine (such as diphenhydramine 50 mg), and 100 mg methylprednisolone intravenously, or equivalents, to reduce the incidence of potential infusion reactions. In patients with Common Terminology for Adverse Events (CTCAE) Grade 3 or higher (severe) infusion reactions with associated respiratory symptoms (stridor, wheeze or bronchospasm), additional treatment with bronchodilators may be indicated.

Routine laboratory studies are obtained throughout the study, with additional tests following courses of study drug treatment. Immune panel, serum human anti-human antibody (HAHA), and thyroid tests are also conducted. Serum samples of all patients are collected for pharmacokinetic analysis and blood samples are collected for B-cell count determination. B-cell counts are followed as a pharmacodynamic marker of ocrelizumab.

Patient Population and Selection Criteria

The target population for this study includes patients with primary progressive MS. Patients with primary progressive MS eligible for this study are characterized by a diagnosis in accordance with the revised McDonald criteria (2005). Patients are selected with evidence of active disease and higher risk for more rapid disability progression, using criteria identified as potential risk factors in previous clinical trials with progressive MS patients. These factors include younger age, evidence of inflammation in the cerebrospinal fluid (CSF) (oligoclonal bands or elevated IgG index), and more rapid historical accumulation of disability.

All patients volunteering and eligible for participation in the study are screened for conformance with the following inclusion and exclusion criteria:

Inclusion Criteria Include:

1. Diagnosis of Primary Progressive Multiple Sclerosis in accordance with the revised McDonald criteria (2005).
2. Ages 18-55 years inclusive.
3. EDSS at screening from 3.0 to 6.5 points.
4. Score of ≥2.0 on the Functional Systems (FS) scale for the pyramidal system that is due to lower extremity findings.
5. Documented history or presence at screening of at least one of the following laboratory findings in a CSF specimen as indicated by, elevated IgG index and/or IgG oligoclonal bands detected by isoelectric focusing.

6. Disease duration from the onset of MS symptoms: less than 15 years in patients with an EDSS at screening >5.0 or less than 10 years in patients with an EDSS at screening ≤5.0.

Exclusion Criteria Include:
1. History of relapsing remitting, secondary progressive, or progressive relapsing multiple sclerosis at screening (Visit 1).

Efficacy Analysis

The primary efficacy endpoint is the time to confirmed disease progression. Disease progression is defined as an increase of ≥1.0 point from baseline EDSS, if the baseline EDSS is between 2.0 and 5.5 points (inclusive), or an increase of ≥0.5 points, if the baseline EDSS is >5.5 points, for which change is not attributable to another etiology (e.g., fever, concurrent illness, MS relapse or exacerbation, or concomitant medication).

The EDSS is based on a standard neurological examination; the seven categories of the EDSS representing functional systems (pyramidal, cerebellar, brainstem, sensory, bowel and bladder, visual, and cerebral and/or mental, plus "other") are rated and scored (collectively, functional system scores or FSS). Each score of the FSS is an ordinal clinical rating scale ranging from 0 to 5 or 6. These ratings are then used in conjunction with observations and information concerning ambulation and use of assistive devices to determine the EDSS score. The EDSS is a disability scale that ranges in 0.5-point steps from 0 (normal) to 10 (death).

The secondary efficacy endpoints in support of the primary efficacy endpoint include: change from baseline to Week 120 in the total volume of T2 lesions on brain MRI scan, change from baseline to Week 120 in the 25-foot timed walk, time to confirmed disease progression, with confirmation occurring at least 24 weeks (≥168 days) after initial disease progression.

Assessment of Relapse

Patients are evaluated for relapses by the treating investigator at each visit throughout the study and, if necessary, at unscheduled visits to confirm relapses occurring between the visits. To meet the criteria for a protocol-defined relapse, the relapse is defined as the occurrence of new or worsening neurological symptoms attributable to MS and immediately preceded by a relatively stable or improving neurological state of least 30 days. Symptoms must persist for >24 hours and should not be attributable to confounding clinical factors (e.g., fever, infection, injury, adverse reactions to concomitant medications). The new or worsening neurological symptoms must be accompanied by objective neurological worsening consistent with an increase of at least half a step on the EDSS, or 2 points on one of the appropriate FSS, or 1 point on two or more of the appropriate FSS. The change must affect the selected FSS (i.e., pyramidal, ambulation, cerebellar, brainstem, sensory, or visual). Episodic spasms, sexual dysfunction, fatigue, mood change or bladder or bowel urgency or incontinence do not suffice to establish a relapse.

Brain MRI Imaging

Magnetic resonance imaging of the brain and cervical spinal cord are obtained at multiple time points during this study, including at baseline. The brain MRI includes the acquisition of the following scans at each time point: T2-weighted MRI scan and T1-weighted MRI scan (without gadolinium-enhancement).

Change from baseline to Week 120 in the total volume of T2 lesions and timed 25 foot walk are compared between ocrelizumab and placebo using ranked analysis of variance. The model includes the two stratification factors noted in the primary analysis.

---

What is claimed is:

1. A method of treating multiple sclerosis in a patient comprising administering an effective amount of ocrelizumab to the patient to provide an initial ocrelizumab exposure of between about 0.3 to about 0.6 grams followed by a second ocrelizumab exposure of between about 0.3 to about 0.6 grams, the second exposure not being provided until from about 16 to 60 weeks from the initial exposure, and each of the ocrelizumab exposures is provided to the patient as one or two doses of ocrelizumab.

2. The method of claim 1, wherein the initial ocrelizumab exposure comprises a first dose and a second dose of ocrelizumab, wherein the first dose and second dose of ocrelizumab is about 0.3 grams.

3. The method of claim 2, wherein the second dose is administered from about 3 to 17 days from the time the first dose was administered.

4. The method of claim 2, wherein the second dose is administered from about 6 to 16 days from the time the first dose was administered.

5. The method of claim 2, wherein the second dose is administered from about 13 to 16 days from the time the first dose was administered.

6. The method of claim 2, wherein the second dose is administered 15 days from the time the first dose was administered.

7. The method of claim 2, wherein the second ocrelizumab exposure comprises a single dose of ocrelizumab, wherein the single dose of ocrelizumab is 0.6 grams.

8. The method of claim 7, wherein the second ocrelizumab exposure is provided approximately 24 weeks after the initial ocrelizumab exposure.

9. The method of claim 8, further comprising providing a third ocrelizumab exposure.

10. The method of claim 9, wherein the third ocrelizumab exposure is provided approximately 46 to 60 weeks from the initial exposure.

11. The method of claim 9, wherein the third ocrelizumab exposure is provided approximately 46 to 54 weeks from the initial exposure.

12. The method of claim 9, further comprising providing a fourth ocrelizumab exposure.

13. The method of claim 12, further comprising providing a fifth ocrelizumab exposure.

14. The method of claim 8, further comprising providing between about one to about three subsequent ocrelizumab exposures.

15. The method of claim 1, wherein a second medicament is administered with the initial exposure or later exposures, wherein the ocrelizumab is the first medicament.

16. The method of claim 15, wherein the second medicament is selected from the group consisting of an interferon, glatiramer acetate, a cytotoxic agent, a chemotherapeutic agent, mitoxantrone, methotrexate, cyclophosphamide, chlorambucil, azathioprine, gamma globulin, Campath, anti-CD4, cladribine, corticosteroid, mycophenolate mofetil (MMF), cyclosporine, a cholesterol-lowering drug of the statin class, estradiol, testosterone; a hormone replacement drug, a TNF inhibitor, a disease-modifying anti-rheumatic drug (DMARD), a non-steroidal anti-inflammatory drug (NSAID), levothyroxine, cyclosporin A, a somatastatin analogue, a cytokine or cytokine receptor antagonist, an anti-metabolite, an immunosuppressive agent, an integrin antagonist or antibody, an LFA-1 antibody, efalizumab, an alpha 4 integrin antibody, natalizumab, and another B-cell surface marker antibody.

17. The method of claim 1, wherein the multiple sclerosis is primary progressive multiple sclerosis (PPMS).

18. The method of claim 1, wherein the multiple sclerosis is relapsing remitting multiple sclerosis (RRMS).

19. The method of claim 1, wherein the subject has never been previously treated with an anti-CD20 antibody.

20. The method of claim 1, wherein the ocrelizumab is a naked antibody.

21. The method of claim 1, wherein the ocrelizumab is conjugated to another molecule.

22. The method of claim 21, wherein the other molecule is a cytotoxic agent.

23. The method of claim 1, wherein the ocrelizumab is administered intravenously.

24. The method of claim 1, wherein the ocrelizumab is administered subcutaneously.

25. The method of claim 1, wherein the ocrelizumab is administered intrathecally.

26. The method of claim 1, wherein ocrelizumab is the only medicament administered to the subject to treat multiple sclerosis.

27. The method of claim 1, wherein the subject has elevated anti-myelin basic protein (MBP), anti-myelin oligodendrocytic glycoprotein (MOG), anti-ganglioside and/or anti-neurofilament antibody levels.

28. The method of claim 1, wherein elevated levels of B cells are present in cerebrospinal fluid (CSF), multiple sclerosis lesion, or serum of the subject.

29. An article of manufacture comprising:
(a) a container comprising ocrelizumab; and
(b) a package insert with instructions for treating multiple sclerosis in a patient, wherein the instructions indicate that an amount of ocrelizumab is administered to the patient that is effective to provide an initial ocrelizumab exposure of between about 0.3 to about 0.6 grams followed by a second ocrelizumab exposure of between about 0.3 to about 0.6 grams, the second exposure not being administered until from about 16 to 60 weeks from the initial exposure, and each of the ocrelizumab exposures is provided to the patient as one or two doses of ocrelizumab.

* * * * *